United States Patent
Wang et al.

(10) Patent No.: US 10,844,017 B2
(45) Date of Patent: Nov. 24, 2020

(54) BIARYL COMPOUND, PREPARATION METHOD AND USE THEREOF

(71) Applicant: FUDAN UNIVERSITY, Shanghai (CN)

(72) Inventors: Yonghui Wang, Shanghai (CN); Yafei Huang, Shanghai (CN); Ruomeng Qiu, Shanghai (CN); Ting Tang, Shanghai (CN)

(73) Assignee: FUDAN UNIVERSITY, Shanghai (CN)

( * ) Notice: Subject to any disclaimer, the term of this patent is extended or adjusted under 35 U.S.C. 154(b) by 0 days.

(21) Appl. No.: 16/484,184

(22) PCT Filed: Feb. 9, 2018

(86) PCT No.: PCT/CN2018/075905
§ 371 (c)(1),
(2) Date: Aug. 7, 2019

(87) PCT Pub. No.: WO2018/145653
PCT Pub. Date: Aug. 16, 2018

(65) Prior Publication Data
US 2020/0002280 A1 Jan. 2, 2020

(30) Foreign Application Priority Data

Feb. 9, 2017 (CN) .......................... 2017 1 0071130
May 15, 2017 (CN) .......................... 2017 1 0339397

(51) Int. Cl.
| | | |
|---|---|---|
| *C07D 213/64* | (2006.01) | |
| *C07C 255/60* | (2006.01) | |
| *C07D 231/12* | (2006.01) | |
| *C07D 213/56* | (2006.01) | |
| *C07C 317/32* | (2006.01) | |
| *C07D 213/71* | (2006.01) | |
| *C07F 9/28* | (2006.01) | |
| *C07C 317/40* | (2006.01) | |
| *C07D 205/04* | (2006.01) | |
| *C07D 207/09* | (2006.01) | |
| *A61P 35/00* | (2006.01) | |

(52) U.S. Cl.
CPC ............ *C07D 213/64* (2013.01); *A61P 35/00* (2018.01); *C07C 255/60* (2013.01); *C07C 317/32* (2013.01); *C07C 317/40* (2013.01); *C07D 205/04* (2013.01); *C07D 207/09* (2013.01); *C07D 213/56* (2013.01); *C07D 213/71* (2013.01); *C07D 231/12* (2013.01); *C07F 9/28* (2013.01)

(58) Field of Classification Search
CPC .. C07D 213/64; C07D 205/04; C07D 207/09; C07D 213/56; C07D 231/12; C07D 213/71; A61P 35/00; C07C 255/60; C07C 317/32; C07C 317/40; C07F 9/28
USPC .................................................... 514/210.01
See application file for complete search history.

(56) References Cited

FOREIGN PATENT DOCUMENTS

| | | |
|---|---|---|
| CN | 103998032 A | 8/2014 |
| CN | 105272904 A | 1/2016 |
| JP | 2016108257 A | 6/2016 |
| WO | 2013029338 A1 | 3/2013 |
| WO | 2013171729 A2 | 11/2013 |
| WO | 2015070091 A1 | 5/2015 |
| WO | 2016193470 A1 | 12/2016 |

OTHER PUBLICATIONS

ISA State Intellectual Property Office of the People's Republic of China, International Search Report Issued in Application No. PCT/CN2018/075905, dated Apr. 27, 2018, WIPO, 6 pages.

*Primary Examiner* — Kristin A Vajda
(74) *Attorney, Agent, or Firm* — Alleman Hall Creasman & Tuttle LLP

(57) ABSTRACT

The present invention belongs to the technical field of chemical pharmaceuticals, and relates to a compound represented by general formula (I) or formula (II) and a preparation method thereof. The compounds are biaryl derivatives with RORγt activation activity. The biaryl derivatives disclosed in this invention can effectively activate the RORγt protein receptor, and thereby promote the differentiation of Th17 cells and increasing the production of IL-17, which can be used as an immune modulator for the treatment of various cancers or viral infection-related diseases.

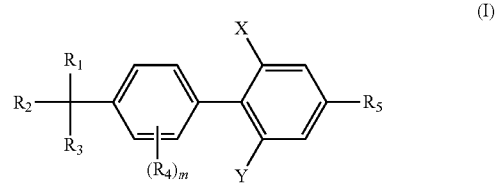

(I)

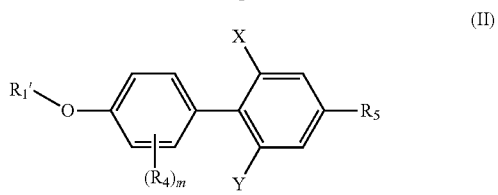

(II)

7 Claims, 2 Drawing Sheets

BIARYL COMPOUND, PREPARATION METHOD AND USE THEREOF

FIELD OF THE INVENTION

The present invention belongs to the technical field of chemical pharmaceuticals, and relates to biaryl derivatives with RORγt activation activity and a preparation process thereof, and the present invention further relates to uses of such biaryl derivatives in preparing drugs for treating RORγt-related diseases.

BACKGROUND

The prior art discloses that tumor immunotherapy controls and attacks tumor cells by mobilizing the body's immune system and enhancing the anti-tumor immunity within tumor microenvironment. The tumor immunotherapy is targeted at the immune system of human body rather than being targeted directly at the tumor. Tumor immunotherapy has attracted much attention in recent years and is the focus of the field of cancer therapy. Cancer immunotherapy has showed strong anti-tumor activity in the treatment of some types of tumor such as melanoma, non-small cell lung cancer (NSCLC) and the like. And some monoclonal antibodies for cancer immunotherapy have been approved by FDA in US. Cancer immunotherapy was named as the most important scientific breakthrough of the year 2013 by the journal Science due to its excellent efficacy and high innovation. Cancer immunotherapy is expected to be an innovation in the field of cancer treatment following after surgery, chemotherapy, radiotherapy and targeted therapy.

T helper 17 cells (Th17) are newly discovered subtype of helper T cells that mainly secrete interleukin-17 (IL-17). Th17 cells were found to play an important role in the development of autoimmunity and inflammation. Current studies have revealed that Th17 cells exist extensively in tumor tissues, however the function of Th17 in tumor tissues is still unknown. In 2009, Professor Chen Dong published an article in Immunity and mainly analyzed that Th17 cells could promote the activation of cytotoxic T cells and thus played a role in the cancer immunotherapeutic. It was found that IL-17A deficient mice are more susceptible to developing lung melanoma (a kind of cancer). If the mice were treated with adoptive T-cell therapy using T cells secreting IL-17A, the occurrence of tumors would be prevented effectively. More importantly, with the help of IL-17A, Th17 cells showed stronger therapeutic effects than Th1 cells. Even more surprisingly, treating with Th17 cells also could effectively activate the tumor-specific CD8+ T cells, which are essential anti-tumor cells. Studies have shown that Th17 cells could recruit dendritic cells into tumor tissues and allow CD8α+ dendritic cells to accumulate in the tumor tissues. In addition, Th17 cells could activate the chemokine CCL20 of tumor tissues. In general, Th17 cells could effectively promote the activity of tumor-specific CD8+ T cells, and these new findings have broadened the horizon of cancer immunotherapy.

The prior art also discloses retinoic acid receptor-related orphan receptors (retinoid-related orphan receptors, RORs), also known as NR1F, which are members of the ligand-dependent transcription factor nuclear receptor (NR) superfamily. The RORs subfamily mainly includes three members: RORα, RORβ and RORγ. There are two different subtypes of RORγ: RORγ1 and RORγt (also known as RORγ2). RORγ1 is distributed in skeletal muscle, thymus, testis, pancreas, prostate, heart, and liver, etc., while RORγ2 (RORγt) is only expressed in some immune cells. RORγt is specifically expressed in Th17 cells and the activation of RORγt could promote the differentiation of Th17 cells to produce the pro-inflammatory cytokine IL-17. Therefore, increase in Th17 cell differentiation through RORγt activation will theoretically produce cancer immunotherapeutic effects by stimulating the activity of tumor-specific CD8+ T cells.

On Jun. 9, 2015, Celgene reached an agreement with Lycera on a T-cell drug against cancer with an advance payment of $82.5 million plus a recent payment of $22.5 million. Lycera is a company derived from the University of Michigan. In February 2015, Lycera announced it had substantial evidence that oral RORγ agonists could improve the efficacy of T cell therapy, by increasing the production of IL-17, promoting the activation of Tc cells, and thereby stimulating the immune response to cancer cells and bringing about a long-lasting cancer cell killing effect. In January 2017, the drug has officially entered phase I clinical trials. This cooperation fully demonstrates the great potential of RORγt agonists for cancer immunotherapy.

Therefore, RORγt can be used as a potential target for cancer immunotherapy. It is of great significance to search for small molecule agonists for RORγt and use them in the treatment of viral infections and cancers.

DETAILED DESCRIPTION OF THE INVENTION

The present invention is directed to provide a class of biaryl compounds represented by general formula (I) or (II) and pharmaceutically acceptable salts thereof:

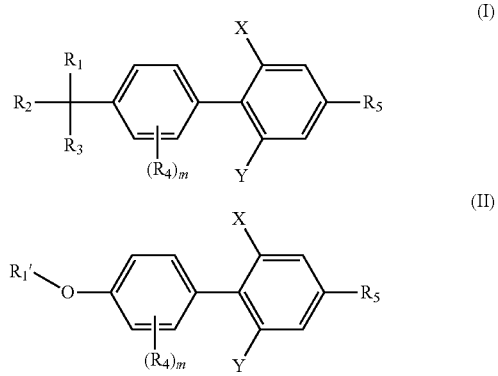

wherein:
$R_1$, $R_2$ and $R_3$ are each independently selected from a group consisting of hydrogen, $R_{11}$-substituted $C_1$-$C_6$ alkyl, $R_{11}$-substituted $C_3$-$C_8$ cycloalkyl, $R_{11}$-substituted $C_3$-$C_8$ heterocycloalkyl, —C(O)$R_9$, —C(O)NR$_9$R$_{10}$, —NR$_9$C(O)R$_{10}$, —OR$_9$ and —NR$_9$R$_{10}$; or any two of $R_1$, $R_2$ and $R_3$ form $C_2$-$C_8$ alkyl alkenyl or $C_3$-$C_7$ cycloalkyl alkenyl, or $R_1$, $R_2$ and $R_3$ form $C_2$-$C_6$ alkyl alkynyl; or any two of $R_1$, $R_2$ and $R_3$ form $C_3$-$C_8$ cycloalkyl or $C_3$-$C_8$ heterocycloalkyl;
$R_1'$ is selected from a group consisting of hydrogen, $C_3$-$C_6$ alkyl, $C_1$-$C_6$ cycloalkyl, $C_3$-$C_6$ heterocycloalkyl and $C_1$-$C_6$ alkyl acyl;
$R_4$ is optionally selected from a group consisting of hydrogen, —OCF$_3$, —OCHF$_2$, —CF$_3$, halogen, —CN, $C_1$-$C_3$ alkyl, $C_1$-$C_3$ alkoxyl, aryl, heteroaryl, and —OR$_9$-substituted heterocycloalkyl;

X, Y are each independently selected from a group consisting of hydrogen, halogen, —CN, —OCF$_3$, —CF$_3$, C$_1$-C$_6$ alkyl, C$_3$-C$_8$ cycloalkyl, C$_3$-C$_8$ heterocycloalkyl, aryl, heteroaryl, C$_1$-C$_3$ alkoxyl, C$_1$-C$_3$ alkyl amino, C$_1$-C$_3$ acyl, C$_1$-C$_3$ acyloxyl and C$_1$-C$_3$ amide;

R$_5$ is optionally selected from

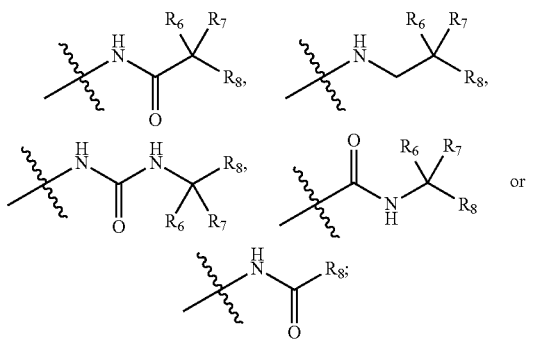

R$_6$ and R$_7$ are each independently selected from a group consisting of hydrogen, hydroxyl, halogen, —CN, —OCF$_3$, —CF$_3$ and C$_1$-C$_3$ alkyl; or R$_6$ and R$_7$ form C$_3$-C$_8$ cycloalkyl or C$_3$-C$_8$ heterocycloalkyl;

R$_8$ is optionally selected from a group consisting of C$_1$-C$_8$ alkyl, C$_3$-C$_8$ cycloalkyl, C$_3$-C$_8$ heterocycloalkyl, phenyl substituted with one or more R$_{31}$, and heteroaryl substituted with one or more R$_{31}$;

R$_9$, R$_{10}$ are each independently selected from a group consisting of hydrogen, C$_1$-C$_6$ alkyl, C$_3$-C$_6$ cycloalkyl and C$_3$-C$_8$ heterocycloalkyl, or R$_9$ and R$_{10}$ form a cyclic group having four to seven ring members together with the nitrogen atom to which they attach; the cyclic group contains or does not contain a second heteroatom selected from oxygen as a ring member;

R$_{11}$ is optionally selected from a group consisting of halogen, —CN, —OCF$_3$, —CF$_3$, C$_1$-C$_4$ alkyl acyl, C$_1$-C$_4$ alkyl amide, C$_1$-C$_4$ alkyl sulfonyl, C$_1$-C$_4$ alkyl sulfonamide, C$_1$-C$_4$ alkyl phosphoryl, C$_1$-C$_4$ alkoxyl and C$_1$-C$_4$ alkyl ester;

R$_{31}$ is optionally selected from a group consisting of hydrogen, C$_1$-C$_8$ alkyl, C$_3$-C$_8$ cycloalkyl, halogenated C$_1$-C$_8$ alkyl, halogen, —CN, —CF$_3$, —OCF$_3$, C$_1$-C$_6$ alkyl sulfonyl, —SO$_2$NR$_9$R$_{10}$, —P(O)R$_9$R$_{10}$, —OR$_9$, —C(O)OR$_9$, —C(O)R$_9$, —C(O)NR$_9$R$_{10}$, NR$_9$R$_{10}$, —NR$_9$SO$_2$R$_{10}$ and —NR$_9$C(O)R$_{10}$; m is selected from 0, 1, 2, 3 or 4.

Preferably, R$_1$, R$_2$ and R$_3$ are each independently selected from a group consisting of hydrogen, C$_3$-C$_5$ alkyl, C$_3$-C$_6$ cycloalkyl, C$_3$-C$_6$ heterocycloalkyl containing one oxygen atom, and —NR$_9$R$_{10}$, or any two of R$_1$, R$_2$ and R$_3$ form C$_2$-C$_6$ alkyl alkenyl or C$_3$-C$_7$ cycloalkyl alkenyl, or R$_1$, R$_2$ and R$_3$ form C$_2$-C$_6$ alkyl alkynyl; wherein, R$_9$, R$_{10}$ are each independently selected from a group consisting of hydrogen, C$_1$-C$_6$ alkyl, C$_3$-C$_6$ cycloalkyl and C$_3$-C$_8$ heterocycloalkyl, or R$_9$ and R$_{10}$ form a cyclic group having four to seven ring members together with the nitrogen atom to which they attach; the cyclic group contains or does not contain a second heteroatom selected from oxygen as a ring member;

Preferably, wherein R$_8$ is selected from a group consisting of C$_1$-C$_8$ alkyl, C$_3$-C$_8$ cycloalkyl, C$_3$-C$_8$ oxoheterocycloalkyl, phenyl substituted with one or more R$_{31}$, pyridyl substituted with one or more R$_{31}$, pyrimidinyl substituted with one or more R$_{31}$, pyridone substituted with one or more R$_{31}$, pyrazolyl substituted with one or more R$_{31}$, pyrrolyl substituted with one or more R$_{31}$, pyrrolidone substituted with one or more R$_{31}$.

Preferably, R$_1$ is selected from a group consisting of hydrogen, C$_3$-C$_5$ alkyl, C$_3$-C$_6$ cycloalkyl, C$_3$-C$_6$ heterocycloalkyl containing one oxygen atom, and —NR$_9$R$_{10}$, meanwhile R$_2$ and R$_3$ are both hydrogens; or any two of R$_1$, R$_2$ and R$_3$ form C$_2$-C$_6$ alkyl alkenyl or C$_3$-C$_7$ cycloalkyl alkenyl, or R$_1$, R$_2$ and R$_3$ form C$_2$-C$_6$ alkyl alkynyl.

Preferably, R$_6$ is hydrogen.

Preferably, X, Y are each independently selected from hydrogen, halogen, —CN, —OCF$_3$, —CF$_3$, or —CH$_3$.

Preferably, m is 1 and R$_4$ is hydrogen, —OCF$_3$, —OCHF$_2$, —CF$_3$, halogen, —CN or —CH$_3$.

Preferably, R$_1$, R$_2$ and R$_3$ are each independently selected from a group consisting of hydrogen, R$_{11}$-substituted C$_1$-C$_6$ alkyl, R$_{11}$-substituted C$_3$-C$_8$ cycloalkyl, R$_{11}$-substituted C$_3$-C$_8$ heterocycloalkyl without nitrogen atom, —C(O)R$_9$, —C(O)NR$_9$R$_{10}$, —NR$_9$C(O)R$_{10}$, —OR$_9$ and —NR$_9$R$_{10}$; or any two of R$_1$, R$_2$ and R$_3$ form C$_2$-C$_8$ alkyl alkenyl or C$_3$-C$_7$ cycloalkyl alkenyl, or R$_1$, R$_2$ and R$_3$ form C$_2$-C$_6$ alkyl alkynyl; or any two of R$_1$, R$_2$ and R$_3$ form C$_3$-C$_8$ cycloalkyl or C$_3$-C$_8$ heterocycloalkyl.

Preferably, the biaryl compounds provided in the present invention include, but are not limited to, the following specific compound examples:

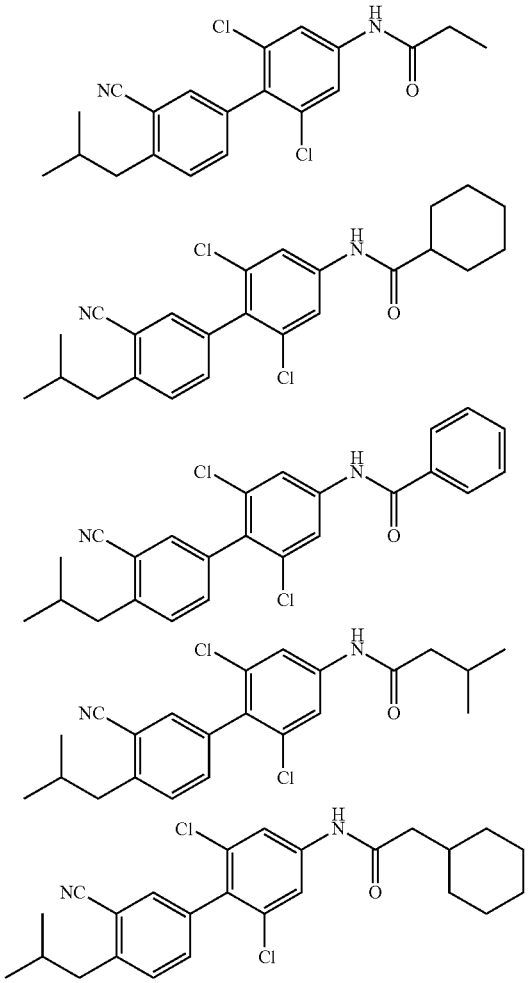

5
-continued
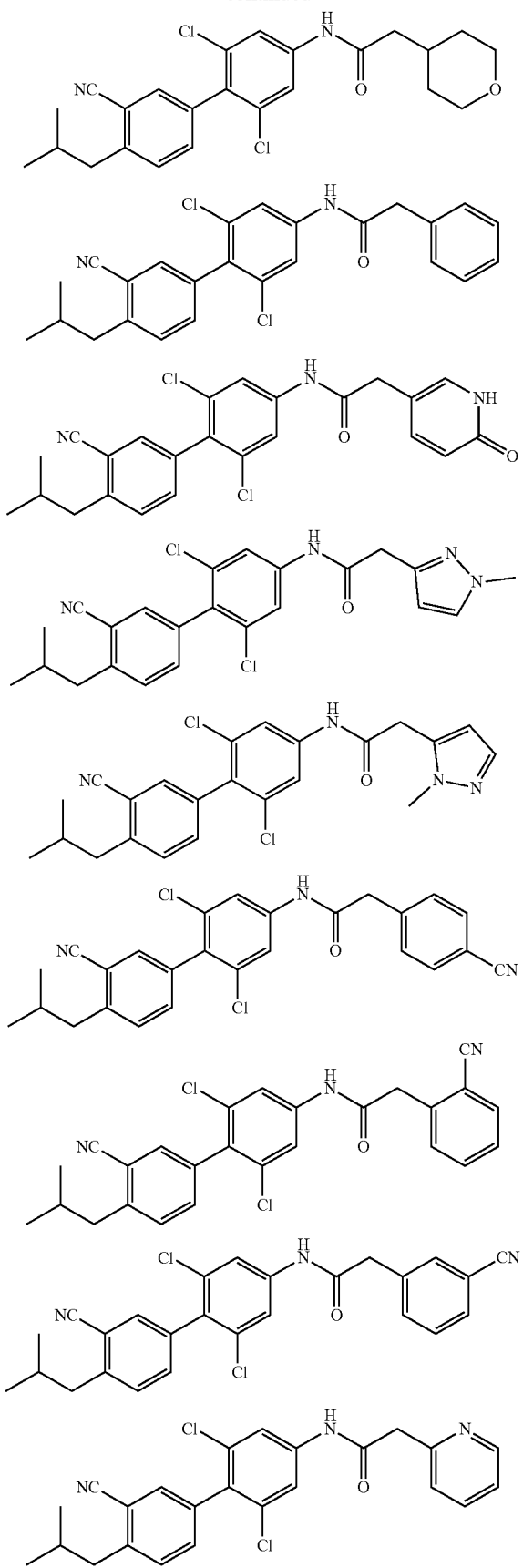
6
-continued
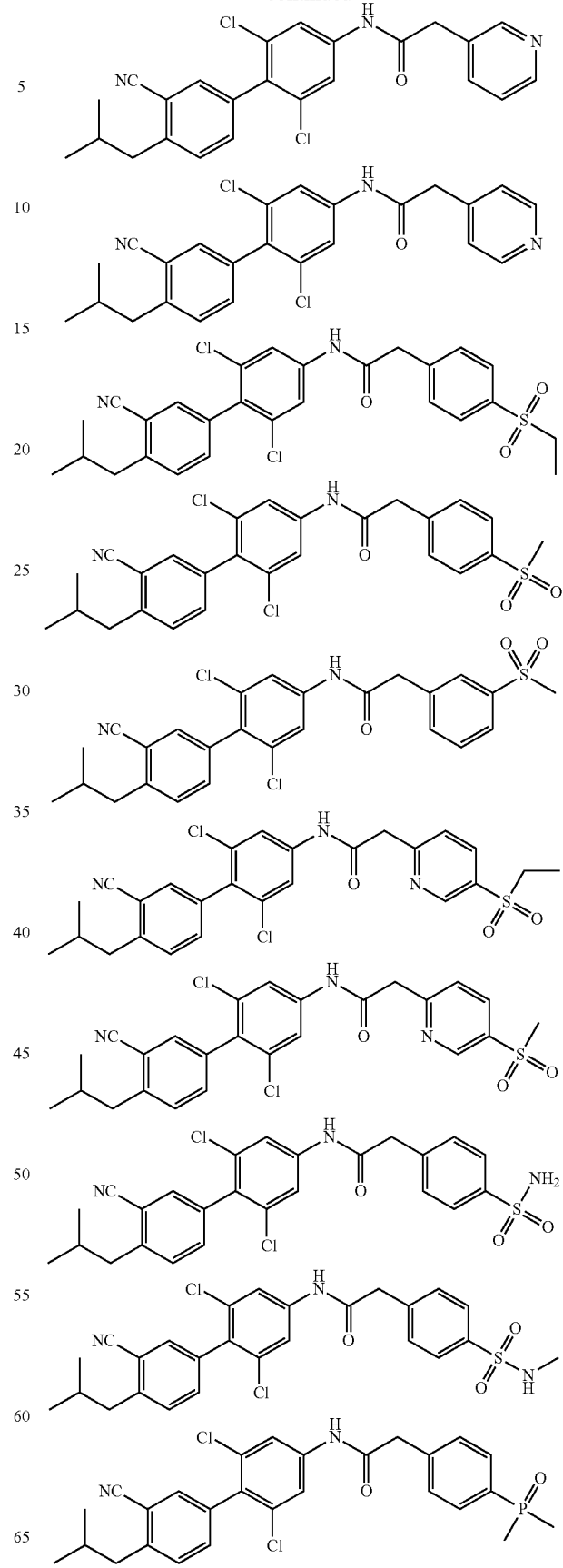

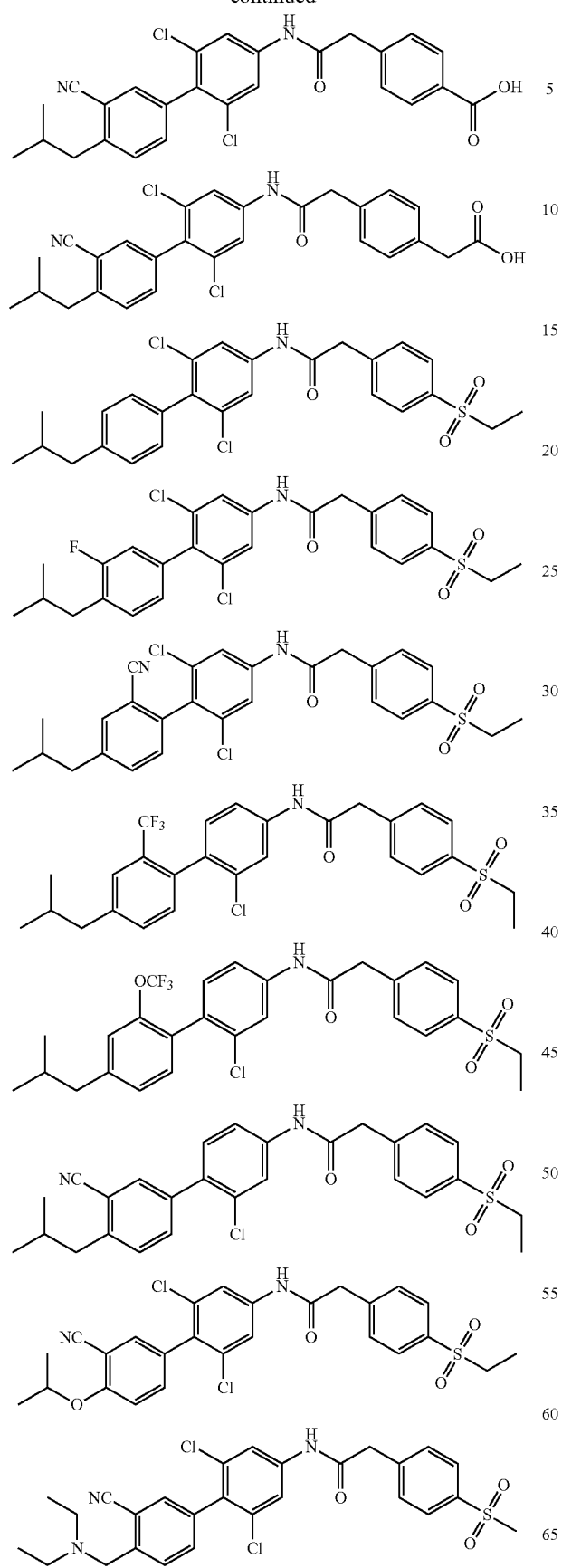
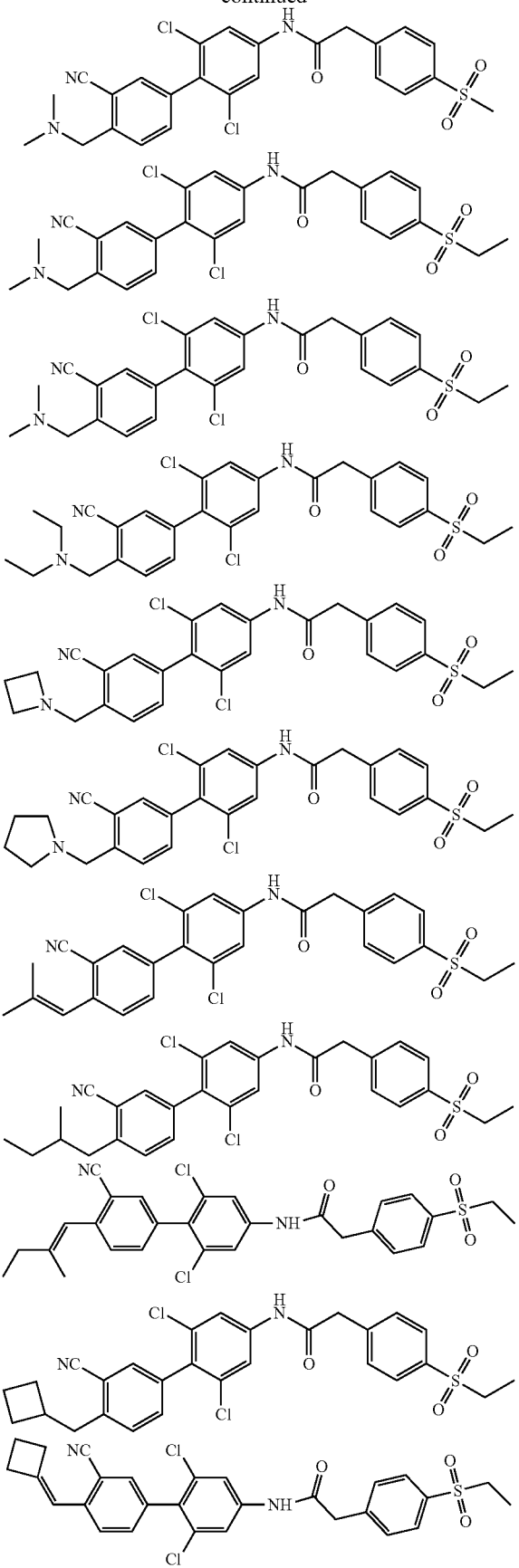

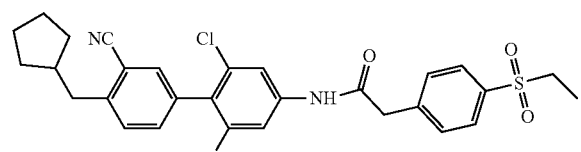
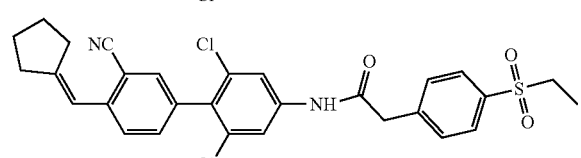
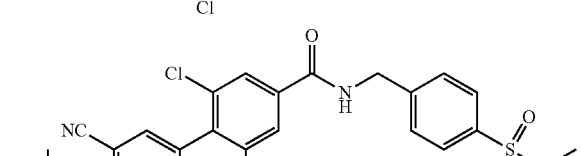
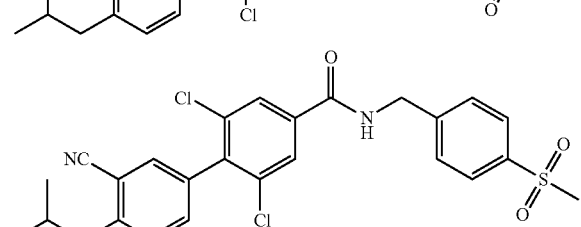
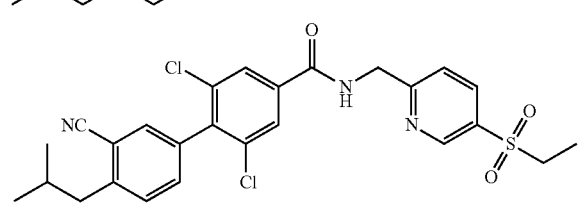
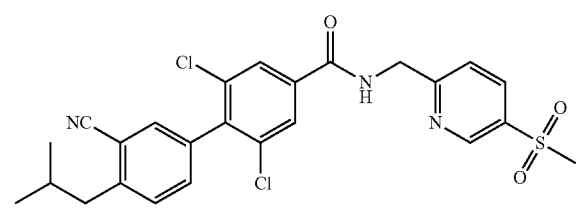
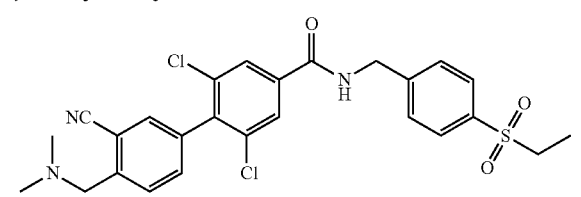
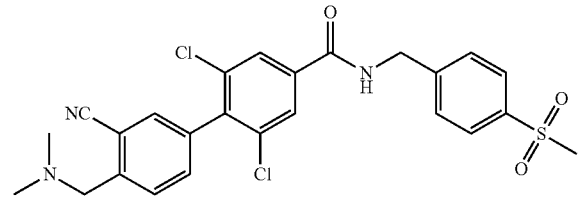
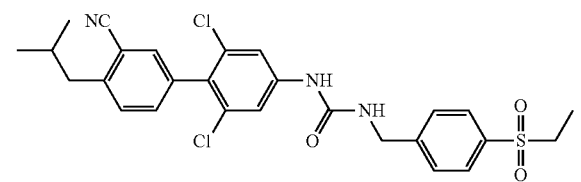
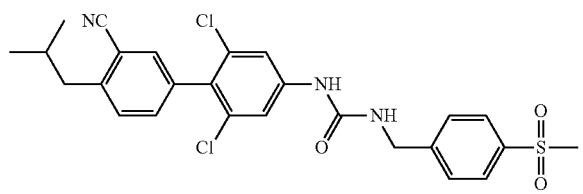
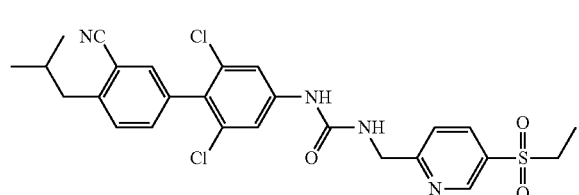
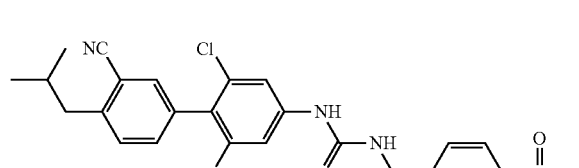
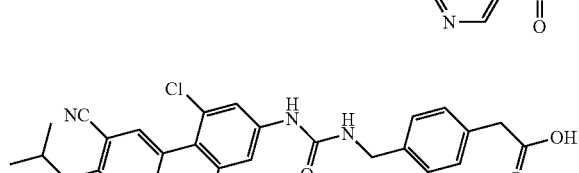
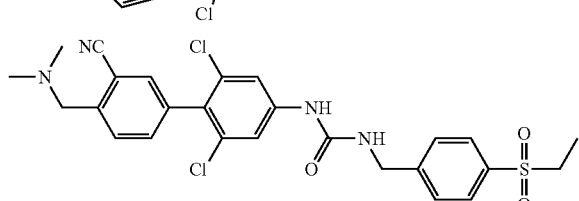
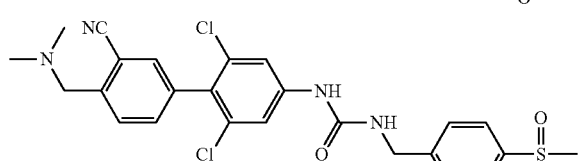
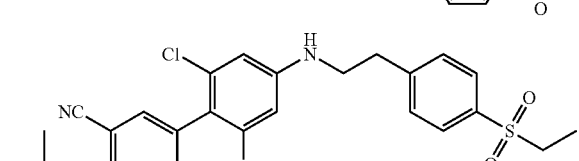
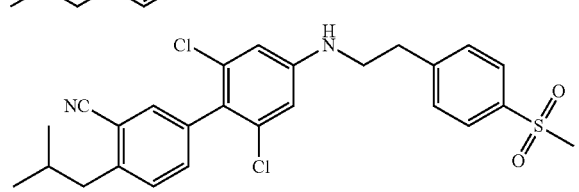
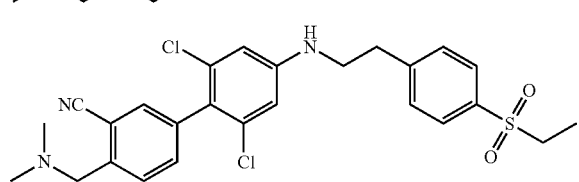

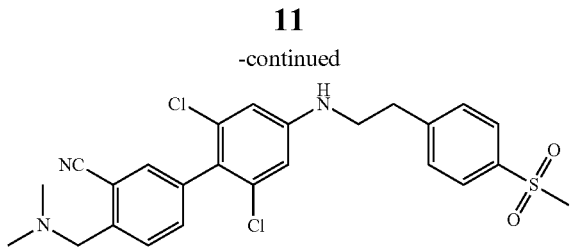

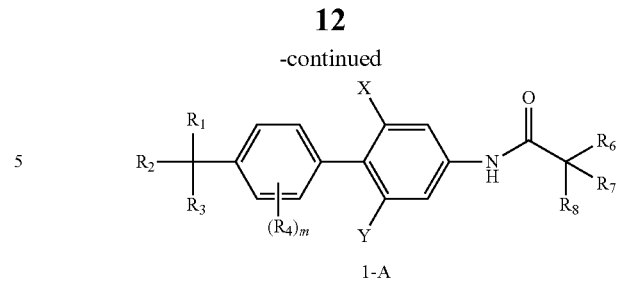

The present invention further provides a pharmaceutical composition comprising the above-mentioned compound or a pharmaceutically acceptable salt thereof.

The present invention further provides a use of the above-mentioned compound or a pharmaceutically acceptable salt thereof in preparing RORγt receptor agonists.

The present invention further provides a use of the above-mentioned compound or a pharmaceutically acceptable salt thereof in preparing drugs for treatment or prevention of RORγt receptor-related diseases. In particular, the diseases are selected from viral infections or cancers.

The present invention further provides a method for preparing biaryl derivatives, including the following synthesis schemes.

Scheme 1:

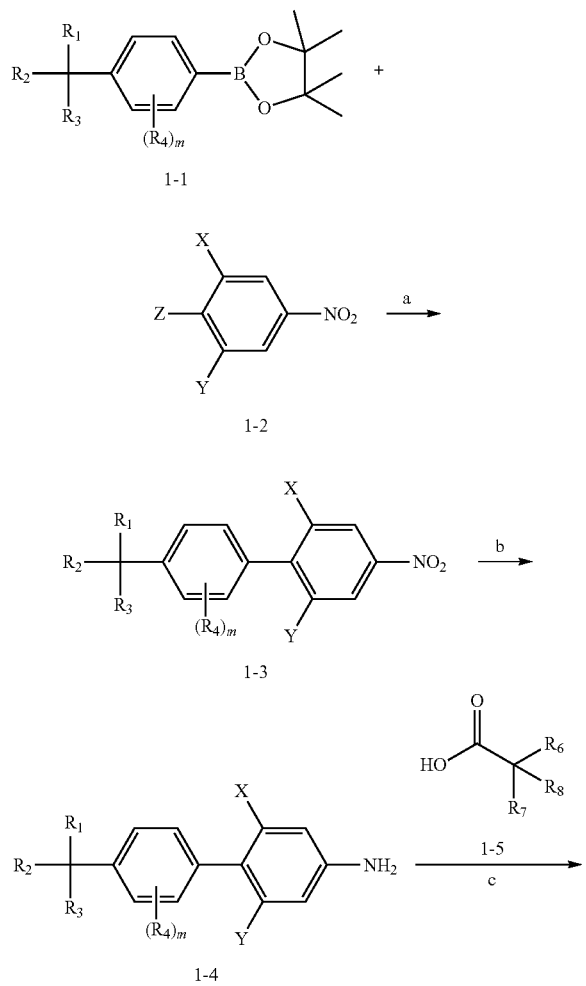

Z = Br or I

Conditions: a) PdCl$_2$(dtbpf), 2 wt % Tween 20/H$_2$O, K$_2$CO$_3$, 50° C.-80° C.; b) Pd/C or platinum dioxide, hydrogen gas, methanol, or ammonium formate, zinc powder, methanol; c) HATU, N,N-diisopropylethylamine, methylene chloride, room temperature;

1) Compounds of formulas 1-1 and 1-2 are subjected to a Suzuki coupling reaction in the presence of PdCl$_2$(dtbpf), 2 wt % Tween 20/H$_2$O, and K$_2$CO$_3$ at 50° C.-80° C. to obtain a product of formula 1-3;

2) The compound of formula 1-3 is reduced by Pd/C and hydrogen gas in methanol at room temperature, or platinum dioxide and hydrogen gas in methanol at room temperature, or ammonium formate and zinc powder in methanol at 60° C., to obtain a product of formula 1-4;

3) The compound of formula 1-4 is condensed with the carboxylic acid of formula 1-5 in the presence of HATU, N,N-diisopropylethylamine in methylene chloride at room temperature to obtain a final product of formula 1-A.

Scheme 2:

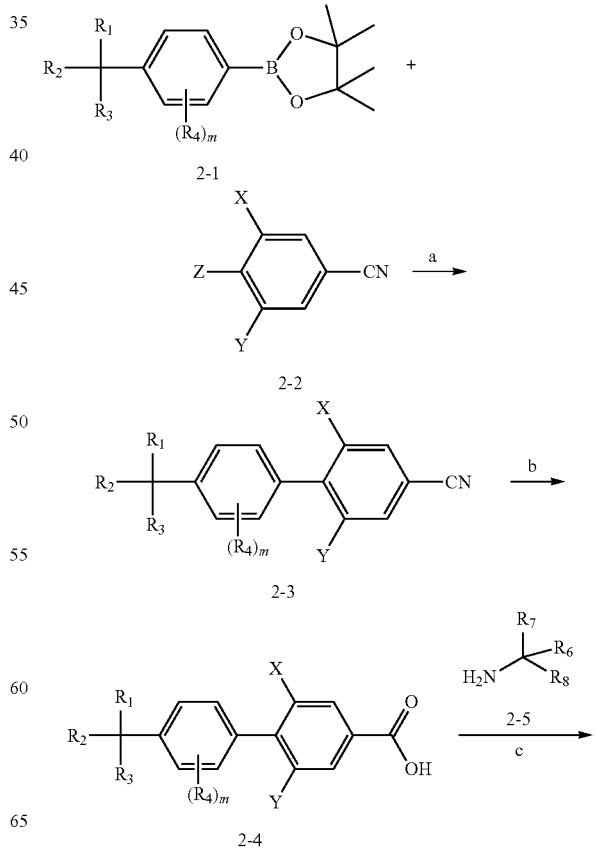

-continued

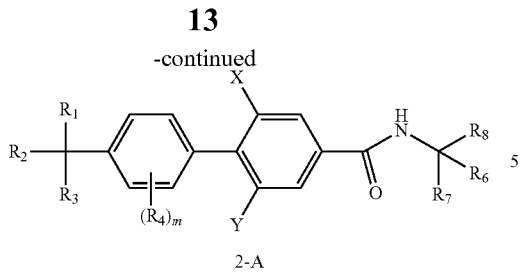

2-A

Z = Br or I

Conditions: a) PdCl$_2$(dtbpf), 2 wt % Tween 20/H$_2$O, K$_2$CO$_3$, 50° C.-80° C.; b) KOH, EtOH/H$_2$O, 50° C;
c) HATU, N,N-diisopropylethylamine, methylene chloride, room temperature;

1) Compounds of formulas 2-1 and 2-2 are subjected to a Suzuki coupling reaction in the presence of PdCl$_2$(dtbpf), 2 wt % Tween 20/H$_2$O, and K$_2$CO$_3$ at 50° C.-80° C. to obtain a product of formula 2-3;
2) The compound of formula 2-3 is hydrolyzed with potassium hydroxide at 50° C. to obtain a product of formula 2-4;
3) The compound of formula 2-4 is condensed with the carboxylic acid of formula 2-5 in the presence of HATU and N,N-diisopropylethylamine in methylene chloride at room temperature to obtain a product of formula 2-A.

Scheme 3:

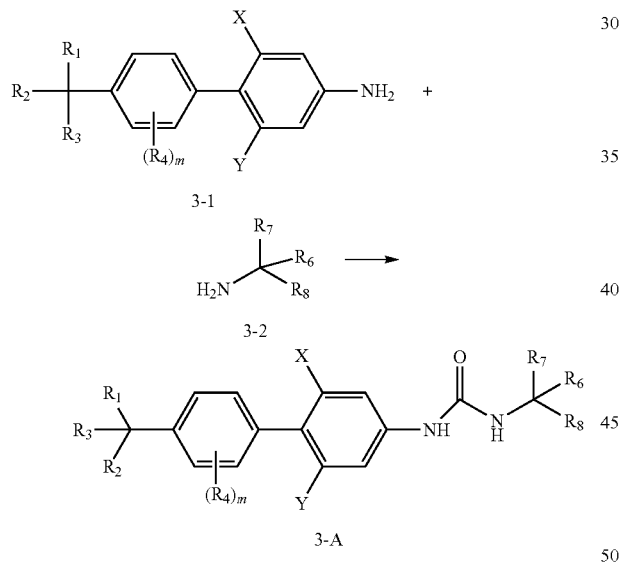

3-A

A compound of formula 3-1 is reacted with a compound of formula 3-2 in the presence of triphosgene and N,N-diisopropylethylamine at a temperature of 0° C. to room temperature to obtain a product of formula 3-A.

Scheme 4:

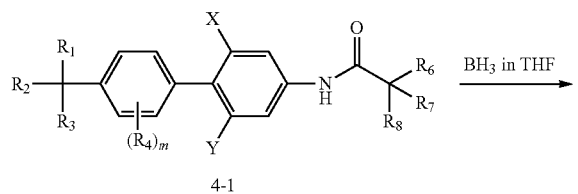

4-1

-continued

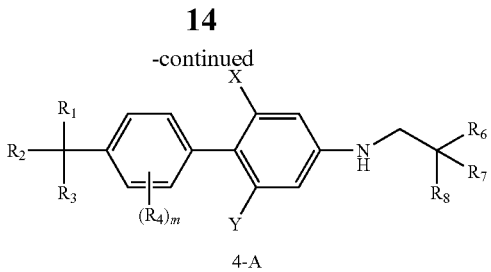

4-A

A compound of formula 4-1 is reduced by borane at room temperature to obtain a product of formula 4-A.

Unless otherwise stated, the groups and terms used in the above synthesis schemes have the same meanings as those in the compounds represented by general formula (I) or (II).

The above synthesis schemes are merely illustrative of the preparation methods for some of the compounds in the present invention. For those skilled in the art, with the common knowledge in the art, and based on the above synthesis schemes, the compounds of the present invention can be synthesized by a similar method.

The "compound", as used herein, includes all stereoisomers, geometric isomers, tautomers and isotopes.

The "compound", as used herein, may be asymmetric, for example, having one or more stereoisomers. Unless otherwise stated, all stereoisomers include, for example, enantiomers and diastereomers. The compound containing an asymmetric carbon atom herein can be separated in an optically active pure form or in a racemic form. The optically active pure form can be resolved from racemic mixtures or can be synthesized with chiral materials or chiral reagents.

The "compound", as used herein, further includes tautomeric forms. The tautomeric form is derived from the exchange of a single bond with an adjacent double bond, accompanying with transfer of a proton.

The invention also includes atoms of all isotopes, whether in an intermediate or a final compound. The atoms of an isotope include those having the same number of atoms but different mass numbers. For example, isotopes of hydrogen include deuterium and tritium.

In the present invention, the terms used have the following meanings unless otherwise specified.

The term "halogen" means fluoro, chloro, bromo or iodo, preferably fluoro or chloro.

The term "hydroxyl" means —OH.

The term "alkyl" means a straight or branched saturated hydrocarbon group consisting of carbon atoms and hydrogen atoms, such as a $C_1$-$C_{20}$ alkyl group, preferably a $C_1$-$C_6$ alkyl, for example, methyl, ethyl, propyl (including n-propyl and isopropyl), butyl (including n-butyl, isobutyl, sec-butyl or tert-butyl), pentyl (including n-pentyl, isopentyl, neopentyl), n-hexyl, and 2-methylhexyl, etc. The alkyl group may be unsubstituted, or substituted by one or more substituents including, but not limited to, alkyl, alkoxyl, cyano, hydroxyl, carbonyl, carboxyl, aryl, heteroaryl, amino, halogen, sulfonyl, sulfinyl, and phosphoryl.

The term "cycloalkyl" means a monocyclic, fused, spiro or bridged ring which solely consists of carbon atoms, such as cyclopropyl, cyclobutyl, cyclopentyl, cyclopentenyl, cyclohexyl, spiro[3.4]octyl, and bicyclic [3.1.1] hexyl. The cycloalkyl group may be unsubstituted, or substituted by one or more substituents including, but not limited to, alkyl, alkoxyl, cyano, hydroxyl, carbonyl, carboxyl, aryl, heteroaryl, amino, halogen, sulfonyl, sulfinyl, and phosphoryl.

The term "heterocycloalkyl" means a monocyclic or fused ring containing one or more heteroatoms selected from the group consisting of nitrogen, oxygen and sulfur, typically, a five to six membered heterocyclyl containing one or more heteroatoms selected from the group consisting of nitrogen, oxygen and sulfur, such as piperazino, morpholino, piperidino, pyrrolidinyl and derivatives thereof. The heterocycloalkyl group may be unsubstituted, or substituted by one or more substituents including, but not limited to, alkyl, alkoxyl, cyano, hydroxyl, carbonyl, carboxyl, aryl, heteroaryl, amino, halogen, sulfonyl, sulfinyl, and phosphoryl.

The term "aryl" means an all-carbon monocyclic or fused ring having a fully conjugated π-electron system, generally having six to fourteen carbon atoms, preferably having six to twelve carbon atoms, and most preferably having six carbon atoms. The aryl group may be unsubstituted, or substituted by one or more substituents including, but not limited to, alkyl, alkoxyl, cyano, hydroxyl, carbonyl, carboxyl, aryl, aralkyl, amino, halogen, sulfonyl, sulfinyl, and phosphoryl. The examples of unsubstituted aryl groups include, but are not limited to, phenyl, naphthyl, and anthracenyl.

The term "heteroaryl" means a monocyclic or fused ring of five to twelve ring atoms, which contains one to four ring atoms selected from the group consisting of nitrogen, oxygen and sulfur, the remaining ring atoms being carbon atoms, and has a fully conjugated π-electron system, including but not limited to, pyrrolyl, furyl, thienyl, imidazolyl, oxazolyl, isoxazolyl, pyrazolyl, pyridyl, pyrimidinyl, pyrazinyl, pyridazinyl, quinolinyl, isoquinolyl, triazolyl, and tetrahydropyrrolyl. The heteroaryl may be unsubstituted, or substituted, the substituents including but not limited to alkyl, alkoxyl, aryl, aralkyl, amino, halogen, hydroxyl, cyano, nitro, carbonyl and heteroalicyclic group. The heteroaryl group may be unsubstituted, or substituted by one or more substituents including, but not limited to, alkyl, alkoxyl, cyano, hydroxyl, carbonyl, carboxyl, aryl, aralkyl, amino, halogen, sulfonyl, sulfinyl, and phosphoryl The term "treatment" means any treatment of diseases in mammals, including: (1) preventing diseases, that is, causing the symptoms of clinical diseases not to develop; (2) inhibiting diseases, that is, arresting the development of clinical symptoms; (3) relieving diseases, that is, causing regression of clinical symptoms.

The present invention further provides a pharmaceutical composition, comprising the compound as described above or a pharmaceutically acceptable salt thereof as an active ingredient, and one or more pharmaceutically acceptable carriers.

A "pharmaceutical composition", as used herein, means a formulation of one or more compounds of the present invention or salt thereof and a carrier generally accepted in the art for delivering a biologically active compound to an organism (for example, a human). The purpose of the pharmaceutical composition is to facilitate administering and delivering a drug to the organism.

The term "pharmaceutically acceptable carrier" means a substance which is co-administered with an active ingredient and facilitates the administration of the active ingredient, including but not limited to any of acceptable glidants, sweeteners, diluents, preservatives, dyes/colorants, flavor enhancers, surfactants, wetting agents, dispersing agents, disintegrating agents, suspending agents, stabilizers, isotonic agents, solvents or emulsifiers which can be used in human or animals (for example, livestock), for example, including but not limited to calcium carbonate, calcium phosphate, various sugars and various types of starch, cellulose derivatives, gelatin, vegetable oils, and polyethylene glycols.

The pharmaceutical composition of the present invention can be formulated into solid, semi-solid, liquid or gaseous preparations, such as tablets, pills, capsules, powders, granules, ointments, emulsions, suspensions, solutions, suppositories, injections, inhalants, gels, microspheres and aerosols, etc.

The pharmaceutical composition of the present invention can be produced by a method known in the art, such as a conventional mixing method, a dissolution method, a granulation method, a sugar coating pill method, a grinding method, an emulsification method, a freeze drying method, etc.

The route of administration of a compound or a pharmaceutically acceptable salt thereof or a pharmaceutical composition thereof in the present invention includes but not limited to oral, rectal, transmucosal, enteral, or topical, transdermal, inhalation, parenteral, sublingual, intravaginal, intranasal, intraocular, intraperitoneal, intramuscular, subcutaneous, or intravenous administration. Preferably, the route of administration is oral administration.

For oral administration, the pharmaceutical composition can be formulated by mixing the active compound with a pharmaceutically acceptable carrier which is known in the art. With these carriers, the compounds can be formulated into tablets, pills, troches, dragees, capsules, liquids, gels, slurries, suspensions or the like for oral administration to a patient. For example, for a pharmaceutical composition for oral administration, a tablet can be obtained by the following way: combining the active ingredient with one or more solid carriers, granulating the resulting mixture if necessary, and adding a small amount of an excipient if necessary to from a mixture or granule, to form a tablet or a tablet core. The tablet core may be combined with an optional enteric coating material, and processed into a form of a coating formulation that is more advantageous for absorption by an organism such as a human.

The present invention further provides an application of the foregoing described compound, or a pharmaceutically acceptable salt thereof in preparing RORγt receptor agonists.

The present invention further provides use of the foregoing described compound, or a pharmaceutically acceptable salt thereof or their pharmaceutical compositions as RORγt receptor agonists in preparing drugs for treatment or prevention of RORγt-related diseases.

Preferably, the aforementioned RORγt receptor-related diseases are selected from viral infections and cancers. The present invention provides a class of biaryl compounds having structural characteristics of general formula (I) or (II). Studies have shown that, this class of compounds can effectively activate the RORγt protein receptor, thereby regulating the differentiation of Th17 cells and increasing the production of IL-17, and can be used as immunomodulators for the treatment of Th17 cell differentiation related diseases.

DETAILED DESCRIPTION

Figure 1:
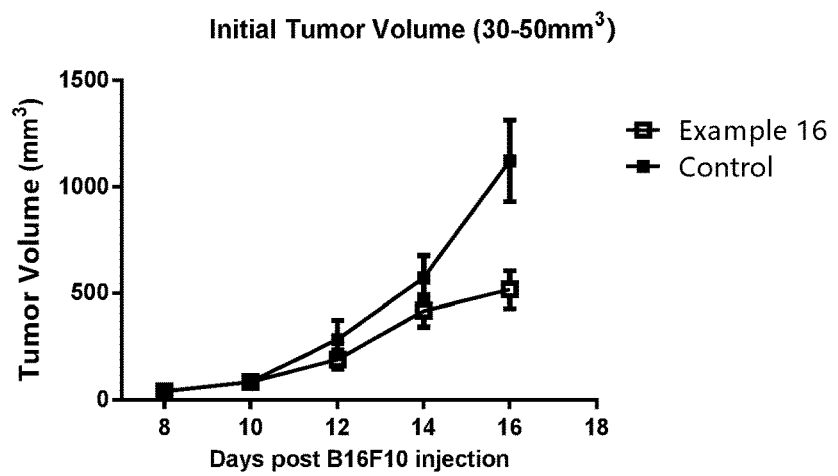
FIG. 1 shows an experimental curve of the compound prepared in example 16 in inhibiting B16F10 murine melanoma cells.

The following embodiments further describe the technical solutions of the present invention, while the protection scope of the present invention is not limited to these embodiments. All modifications or equivalents that do not depart from the inventive concept of the present invention are intended to fall within the scope of protection of the present invention.

In the process for preparing the target compounds provided in the present invention, the column chromatography adopts the silica gels (300-400 mesh) produced by Rushan Sun Desiccant Co., Ltd.; the thin layer chromatography adopts GF254 (0.25 mm); the nuclear magnetic resonance chromatography (NMR) adopts Varian-400 nuclear magnetic resonance spectrometer; and the LC/MS adopts an Agilent Technologi ESI 6120 LC/MS system.

In addition, all operations involving materials that are susceptible to oxidation or hydrolysis are carried out under the protection of nitrogen gas. Unless otherwise stated, the starting materials used herein are commercially available materials that can be used directly without further purification.

Example 1

N-(2,6-Dichloro-3'-cyano-4'-isobutyl-[1,1'-biphenyl]-4-yl)propionamide

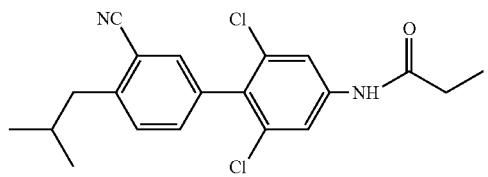 [SMILES: CCC(=O)Nc1cc(Cl)c(-c2ccc(CC(C)C)c(C#N)c2)c(Cl)c1]

Synthesis of Intermediate 1a: 4'-amino-2',6'-dichloro-4-isobutyl-[1,1'-biphenyl]-3-carbonitrile Step 1: Synthesis of 5-bromo-2-(bromomethyl)benzonitrile 5-Bromo-2-methylbenzonitrile (30 g, 153 mmol), N-bromosuccinimide (28.6 g, 161 mmol), benzoyl peroxide (1.85 g, 7.6 mmol) and carbon tetrachloride (300 mL) were added in a 500 mL single-neck flask, and the mixture was heated to react at 90° C. for 4 hours. After completion of the reaction according to TLC, the mixture was cooled, and filtered, and the filtrate was concentrated in vacuo to remove the solvent. The residue was separated by a silica gel column (petroleum ether:ethyl acetate=300:1) to give a product (white solid, 30 g), with a yield of 71.4%. $^1$H NMR (400 MHz, CDCl$_3$) δ 7.79 (s, 1H), 7.71 (dd, J=8.4, 1.9 Hz, 1H), 7.43 (d, J=8.4 Hz, 1H), 4.58 (s, 2H).

Step 2: Synthesis of diethyl (4-bromo-2-cyanobenzyl)phosphonate

5-Bromo-2-(bromomethyl)benzonitrile (36 g, 131 mmol) and triethyl phosphite (33.6 mL, 261 mmol) were added to a 500 mL single-neck flask, and the mixture was heated to react at 155° C. for 2 hours. After completion of the reaction, the mixture was cooled, mixed directly with silica gel, and then was separated by a silica gel column (petroleum ether:ethyl acetate=10:1-1:2) to give a product (yellow liquid, 28.4 g), with a yield of 77.8%. $^1$H NMR (400 MHz, CDCl$_3$) δ 7.76 (s, 1H), 7.67 (dd, J=8.3, 1.5 Hz, 1H), 7.41 (dd, J=8.4, 2.6 Hz, 1H), 4.12-4.06 (m, 4H), 3.36 (s, 1H), 3.31 (s, 1H), 1.28 (t, J=7.1 Hz, 6H).

Step 3: Synthesis of 5-bromo-2-(2-methylprop-1-en-1-yl)benzonitrile

Diethyl (4-bromo-2-cyanobenzyl)phosphonate (8 g, 24 mmol) and anhydrous tetrahydrofuran (80 mL) were added in a 150 mL single-neck flask, and stirred for 5 minutes under an ice bath, and then NaH (1.15 g, 28.8 mmol) was added in portions, and the mixture was reacted in an ice bath for 30 minutes. Acetone (2.78 g, 48 mmol) diluted in anhydrous tetrahydrofuran (5 mL) was dropped into the reaction mixture, then the ice bath was removed. The reaction was continued at room temperature overnight under nitrogen atmosphere. After completion of the reaction, water was added to quench the reaction, and the solution was extracted with ethyl acetate (3*100 mL) and the extract was concentrated in vacuo to remove the solvent. The residue was separated by a silica gel column (petroleum ether:ethyl acetate=100:1) to give a product (white solid, 3.9 g), with a yield of 68.7%. $^1$H NMR (400 MHz, CDCl$_3$) δ 7.74 (d, J=2.0 Hz, 1H), 7.63 (dd, J=8.4, 2.0 Hz, 1H), 7.22 (d, J=8.4 Hz, 1H), 6.35 (s, 1H), 1.95 (d, J=0.9 Hz, 3H), 1.79 (s, 3H).

Step 4: Synthesis of 2-(2-methylprop-1-en-1-yl)-5-(4,4,5,5-tetramethyl-1,3,2-dioxaborolan-2-yl)benzonitrile 5-Bromo-2-(2-methylprop-1-en-1-yl)benzonitrile (3.9 g, 16.5 mmol), bis(pinacolato)diboron (4.48 g, 19.8 mmol), Pd(dppf)Cl$_2$ (603 mg, 0.83 mmol), potassium acetate (4.85 g, 49.5 mmol), and 1,4-dioxane (50 mL) were added to a microwave tube, then nitrogen gas was bubbled through the mixture for 5 minutes, and the mixture was reacted for 1 hour under microwave at 110° C. After completion of the reaction, the mixture was cooled and extracted with ethyl acetate (3*50 mL). The organic layers were combined, washed once with saturated sodium chloride, and concentrated in vacuo to remove the solvent. The residue was separated by a silica gel column (ethyl acetate:petroleum ether=10:1) to give a product (white solid, 3.6 g), with a yield of 77.1%. $^1$H NMR (400 MHz, CDCl$_3$) δ 8.06 (s, 1H), 7.91 (d, J=7.8 Hz, 1H), 7.35 (d, J=7.8 Hz, 1H), 6.45 (s, 1H), 1.96 (s, 3H), 1.81 (s, 3H), 1.34 (s, 12H).

Step 5: Synthesis of 2',6'-dichloro-4-(2-methylprop-1-en-1-yl)-4'-nitro-[1,1'-biphenyl]-3-carbonitrile 2-(2-Methylprop-1-en-1-yl)-5-(4,4,5,5-tetramethyl-1,3,2-dioxaborolan-2-yl) benzonitrile (2 g, 7.1 mmol), 1,3-dichloro-2-iodo-5-nitrobenzene (2.69 g, 8.5 mmol), sodium carbonate (2.36 g, 21.3 mmol), PdCl$_2$(dtbpf) (231 mg, 0.36 mmol) and 2 wt % Tween 20 in H$_2$O (30 mL) were added in a 100 mL single-neck flask, then nitrogen gas was bubbled through the mixture for 5 minutes, and the mixture was reacted for 0.5 hour under microwave at 80° C. After completion of the reaction, the mixture was extracted with ethyl acetate (5*20 mL). The organic layers were combined, washed with saturated sodium chloride, and concentrated in vacuo to remove the solvent. The residue was separated by a silica gel column (petroleum ether:ethyl acetate=100:1-50:1) to give a product (white solid, 2.1 g), with a yield of 85.7%. ¹H NMR (400 MHz, CDCl₃) δ 8.30 (s, 2H), 7.54 (d, J=1.5 Hz, 1H), 7.52 (d, J=8.2 Hz, 1H), 7.41 (dd, J=8.1, 1.6 Hz, 1H), 6.50 (s, 1H), 2.02 (d, J=0.9 Hz, 3H), 1.90 (d, J=0.9 Hz, 3H).

Step 6: 4'-Amino-2',6'-dichloro-4-isobutyl-[1,1'-biphenyl]-3-carbonitrile

2',6'-Dichloro-4-(2-methylprop-1-en-1-yl)-4'-nitro-[1,1'-biphenyl]-3-carbonitrile (1.4 g, 4 mmol), platinum dioxide (100 mg), and methanol (10 mL) were added in a 50 mL single-neck flask, and the mixture was stirred at room temperature under hydrogen atmosphere for 30 minutes, and then additional platinum dioxide (50 mg) was added. The reaction was monitored by LC-MS, and was stopped immediately when it was completed. The mixture was filtered through Celite, and the filtrate was concentrated in vacuo. The residue was separated by a silica gel column (petroleum ether:ethyl acetate=20:1-10:1) to give a product (white solid, 850 mg), with a yield of 56.7%. ¹H NMR (400 MHz, CDCl₃) δ 7.50 (d, J=1.6 Hz, 1H), 7.38 (dd, J=8.0, 1.8 Hz, 1H), 7.32 (d, J=8.0 Hz, 1H), 6.74 (s, 2H), 2.76 (d, J=7.3 Hz, 2H), 2.10-2.00 (m, 1H), 0.99 (d, J=6.6 Hz, 6H).

Synthesis of N-(2,6-dichloro-3'-cyano-4'-isobutyl-[1,1'-biphenyl]-4-yl)propionamide 4'-Amino-2',6'-dichloro-4-isobutyl-[1,1'-biphenyl]-3-carbonitrile (40 mg, 0.13 mmol), propanoic acid (19 mg, 0.26 mmol), HATU (99 mg, 0.26 mmol), N,N-diisopropylethylamine (50 mg, 0.39 mmol) and dichloromethane (2 mL) were added in a 25 mL single-neck flask, and the mixture was reacted at room temperature overnight. After the materials had all reacted when being determined by TLC, dichloromethane (20 mL) was added, and the mixture was washed with saturated ammonium chloride (30 mL), and then the organic layer was concentrated in vacuo to remove the solvent. The resulting crude product was separated by preparative thin layer chromatography (petroleum ether:ethyl acetate=10:1) to give the product (white solid, 43 mg), with a yield of 67.6%. ¹H NMR (400 MHz, CDCl₃) δ 7.90 (s, 1H), 7.69 (s, 2H), 7.48 (s, 1H), 7.35 (q, J=8.0 Hz, 2H), 2.75 (d, J=7.3 Hz, 2H), 2.42 (q, J=7.5 Hz, 2H), 1.85 (m, 1H), 1.24 (t, J=7.3, 3H), 0.97 (d, J=6.6 Hz, 6H). MS (ESI) m/z: 375.0 (M+1).

Example 2

N-(2,6-Dichloro-3'-cyano-4'-isobutyl-[1,1'-biphenyl]-4-yl)cyclohexanecarboxamide

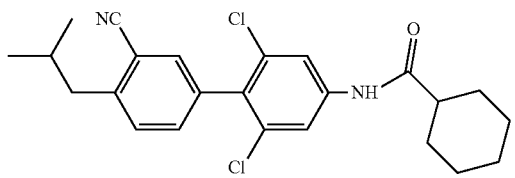 [SMILES: CC(C)Cc1ccc(-c2c(Cl)cc(NC(=O)C3CCCCC3)cc2Cl)cc1C#N]

The method is the same as in Example 1. 4'-Amino-2',6'-dichloro-4-isobutyl-[1,1'-biphenyl]-3-carbonitrile (40 mg, 0.13 mmol), cyclohexanecarboxylic acid (19 mg, 0.15 mmol), HATU (57 mg, 0.15 mmol), N,N-diisopropylethylamine (50 mg, 0.39 mmol) and dichloromethane (2 mL) were reacted at room temperature overnight to give a product (white solid, 50 mg), with a yield of 94.3%. ¹H NMR (400 MHz, CDCl₃) δ 8.01 (s, 1H), 7.71 (s, 2H), 7.49 (s, 1H), 7.40-7.33 (m, 2H), 2.77 (d, J=7.3 Hz, 2H), 2.34-2.24 (m, 1H), 1.94 (d, J=13.0 Hz, 2H), 1.85 (d, J=11.9 Hz, 2H), 1.80-1.67 (m, 3H), 1.62-1.49 (m, 2H), 1.36-1.29 (m, 2H), 0.99 (d, J=6.6 Hz, 6H). MS (ESI) m/z: 426.9 (M−1).

Example 3

N-(2,6-Dichloro-3'-cyano-4'-isobutyl-[1,1'-biphenyl]-4-yl)benzamide

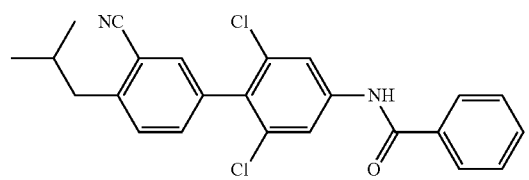 [SMILES: CC(C)Cc1ccc(-c2c(Cl)cc(NC(=O)c3ccccc3)cc2Cl)cc1C#N]

The method is the same as in Example 1. 4'-Amino-2',6'-dichloro-4-isobutyl-[1,1'-biphenyl]-3-carbonitrile (50 mg, 0.16 mmol), benzoic acid (23 mg, 0.19 mmol), HATU (72 mg, 0.19 mmol), N,N-diisopropylethylamine (62 mg, 0.48 mmol) and dichloromethane (2 mL) were reacted at room temperature overnight to give a product (white solid, 10 mg), with a yield of 14.7%. ¹H NMR (400 MHz, CDCl₃) δ 7.81 (s, 1H), 7.67 (d, J=7.4 Hz, 2H), 7.64-7.58 (m, 2H), 7.39 (t, J=7.2 Hz, 1H), 7.30 (d, J=10.0 Hz, 3H), 7.18 (dd, J=17.7, 7.9 Hz, 2H), 2.57 (d, J=7.3 Hz, 2H), 1.85 (m, 1H), 0.79 (d, J=6.5 Hz, 6H). MS (ESI) m/z: 422.9 (M+1).

Example 4

N-(2,6-dichloro-3'-cyano-4'-isobutyl-[1,1'-biphenyl]-4-yl)-3-methylbutanamide

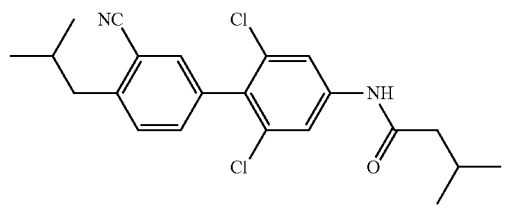 [SMILES: CC(C)CC(=O)Nc1cc(Cl)c(-c2ccc(CC(C)C)c(C#N)c2)c(Cl)c1]

The method is the same as in Example 1. 4'-Amino-2',6'-dichloro-4-isobutyl-[1,1'-biphenyl]-3-carbonitrile (50 mg, 0.16 mmol), 3-methylbutanoic acid (27 mg, 0.26 mmol), HATU (99 mg, 0.26 mmol), N,N-diisopropylethylamine (50 mg, 0.39 mmol) and dichloromethane (2 mL) were reacted at room temperature overnight to give a product (white solid, 35 mg), with a yield of 67.3%. ¹H NMR (400 MHz, CDCl₃) δ 7.68 (s, 2H), 7.48 (d, J=10.3 Hz, 2H), 7.35 (q, J=8.1 Hz, 2H), 2.76 (d, J=7.3 Hz, 2H), 2.29-2.16 (m, 3H), 1.52-1.39 (m, 1H), 1.02 (d, J=6.1 Hz, 6H), 0.98 (d, J=6.6 Hz, 6H). MS (ESI) m/z: 403.0 (M+1).

Example 5

(2-Cyclohexyl-N-(2,6-dichloro-3'-cyano-4'-isobutyl-[1,1'-biphenyl]-4-yl)acetamide)

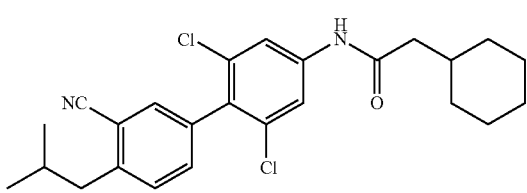 [SMILES: CC(C)Cc1ccc(-c2c(Cl)cc(NC(=O)CC3CCCCC3)cc2Cl)cc1C#N]

The method is the same as in Example 1. 4'-Amino-2',6'-dichloro-4-isobutyl-[1,1'-biphenyl]-3-carbonitrile (40 mg, 0.13 mmol), 2-cyclohexylacetic acid (21 mg, 0.16 mmol), HATU (60 mg, 0.16 mmol), N,N-diisopropylethylamine (50 mg, 0.39 mmol) and dichloromethane (2 mL) were reacted at room temperature overnight to give a product (white solid, 10 mg), with a yield of 22.2%. $^1$H NMR (400 MHz, CDCl$_3$) δ 7.69 (s, 2H), 7.63 (s, 1H), 7.50 (s, 1H), 7.42-7.32 (m, 2H), 2.77 (d, J=7.3 Hz, 2H), 2.26 (d, J=7.0 Hz, 2H), 2.12-2.02 (m, 1H), 1.95-1.84 (m, 1H), 1.80 (d, J=12.7 Hz, 2H), 1.72 (d, J=15.0 Hz, 3H), 1.36-1.24 (m, 3H), 1.21-1.14 (m, 1H), 1.04 (d, J=11.9 Hz, 1H), 0.99 (d, J=6.5 Hz, 6H). MS (ESI) m/z: 443.0 (M+1).

Example 6

N-(2,6-Dichloro-3'-cyano-4'-isobutyl-[1,1'-biphenyl]-4-yl)-2-(tetrahydro-2H-pyran-4-yl) acetamide

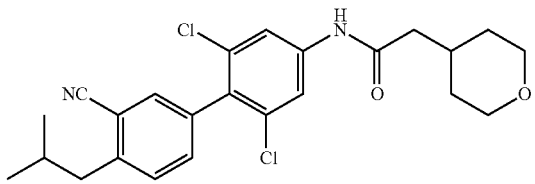 [SMILES: CC(C)Cc1ccc(-c2c(Cl)cc(NC(=O)CC3CCOCC3)cc2Cl)cc1C#N]

The method is the same as in Example 1. 4'-Amino-2',6'-dichloro-4-isobutyl-[1,1'-biphenyl]-3-carbonitrile (40 mg, 0.13 mmol), 2-(tetrahydro-2H-pyran-4-yl)acetic acid (37 mg, 0.26 mmol), HATU (99 mg, 0.26 mmol), N,N-diisopropylethylamine (50 mg, 0.39 mmol) and dichloromethane (2 mL) were reacted at room temperature overnight to give a product (white solid, 20 mg), with a yield of 33.9%. $^1$H NMR (400 MHz, CDCl$_3$) δ 9.10 (s, 1H), 7.77 (s, 2H), 7.50 (s, 1H), 7.42-7.33 (m, 2H), 3.97 (dd, J=11.2, 3.6 Hz, 2H), 3.43 (t, J=11.7 Hz, 2H), 2.77 (d, J=7.2 Hz, 2H), 2.35 (d, J=7.1 Hz, 2H), 2.17 (dd, J=9.2, 5.5 Hz, 1H), 2.12-1.99 (m, 1H), 1.71 (d, J=12.5 Hz, 2H), 1.45-1.34 (m, 2H), 1.00 (d, J=6.6 Hz, 6H). MS (ESI) m/z: 444.9 (M+1).

Example 7

N-(2,6-Dichloro-3'-cyano-4'-isobutyl-[1,1'-biphenyl]-4-yl)-2-phenylacetamide

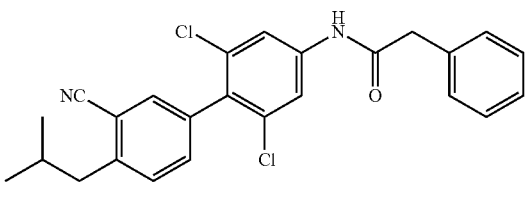 [SMILES: CC(C)Cc1ccc(-c2c(Cl)cc(NC(=O)Cc3ccccc3)cc2Cl)cc1C#N]

The method is the same as in Example 1. 4'-Amino-2',6'-dichloro-4-isobutyl-[1,1'-biphenyl]-3-carbonitrile (50 mg, 0.16 mmol), 2-phenylacetic acid (26 mg, 0.19 mmol), HATU (72 mg, 0.19 mmol), N,N-diisopropylethylamine (62 mg, 0.48 mmol) and dichloromethane (2 mL) were reacted at room temperature for 2 hours to give a product (white solid, 40 mg), with a yield of 58.8%. $^1$H NMR (400 MHz, CDCl$_3$) δ 8.06 (s, 1H), 7.50 (s, 2H), 7.35 (s, 1H), 7.26-7.24 (m, 1H), 7.22-7.20 (m, 3H), 7.19-7.15 (m, 4H), 3.60 (s, 2H), 2.66 (d, J=7.3 Hz, 2H), 2.01-1.85 (m, 1H), 0.88 (d, J=6.6 Hz, 6H). MS (ESI) m/z: 437.2 (M+1).

Example 8

N-(2,6-Dichloro-3'-cyano-4'-isobutyl-[1,1'-biphenyl]-4-yl)-2-(6-oxo-1,6-dihydropyridin-3-yl)acetamide

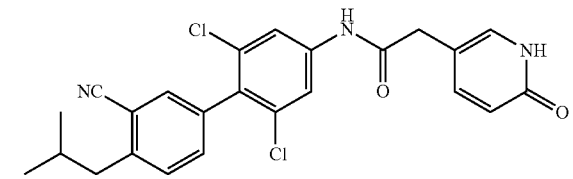 [SMILES: CC(C)Cc1ccc(-c2c(Cl)cc(NC(=O)Cc3ccc(=O)[nH]c3)cc2Cl)cc1C#N]

Step 1: Synthesis of 2-(6-oxo-1,6-dihydropyridin-3-yl)acetic acid 2-(6-Chloropyridin-3-yl)acetic acid (220 mg, 1.3 mmol), H$_2$O (0.6 mL) and acetic acid (2.2 mL) were added in a microwave tube, and the mixture was reacted under microwave at 160° C. for 1 hour. After completion of the reaction, solvent was removed in vacuo to afford a product as white solid, which was used for the next step directly. MS (ESI) m/z: 229.0 (M+1).

Step 2: Synthesis of N-(2,6-dichloro-3'-cyano-4'-isobutyl-[1,1'-biphenyl]-4-yl)-2-(6-oxo-1,6-dihydropyridin-3-yl)acetamide The method is the same as in Example 1. 4'-Amino-2',6'-dichloro-4-isobutyl-[1,1'-biphenyl]-3-carbonitrile (50 mg, 0.16 mmol), 2-(6-oxo-1,6-dihydropyridin-3-yl)acetic acid (41 mg, 0.19 mmol), HATU (72 mg, 0.19 mmol), N,N-diisopropylethylamine (62 mg, 0.48 mmol) and dichloromethane (3 mL) were reacted at room temperature for 3 hours to give a product (white solid, 32 mg), with a yield of 42.2%. $^1$H NMR (400 MHz, CDCl$_3$) δ 9.49 (s, 1H), 7.65 (s, 2H), 7.49 (d, J=8.3 Hz, 1H), 7.41 (s, 2H), 7.33-7.28 (m, 2H), 7.25 (s, 1H), 6.51 (d, J=8.0 Hz, 1H), 3.49 (s, 2H), 2.73 (d, J=6.6 Hz, 2H), 2.04-1.94 (m, 1H), 0.95 (d, J=6.5 Hz, 6H). MS (ESI) m/z: 453.9 (M+1).

Example 9

N-(2,6-Dichloro-3'-cyano-4'-isobutyl-[1,1'-biphenyl]-4-yl)-2-(1-methyl-1H-pyrazol-3-yl)acetamide (9A) and N-(2,6-dichloro-3'-cyano-4'-isobutyl-[1,1'-biphenyl]-4-yl)-2-(1-methyl-1H-pyrazol-5-yl)acetamide (9B)

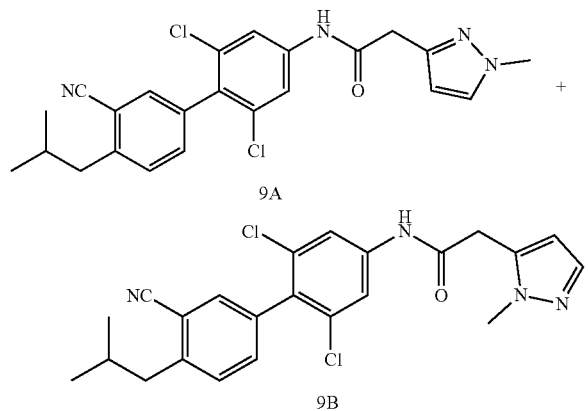

Synthesis of the Intermediates 2-(1-methyl-1H-pyrazol-5-yl)acetic acid (9a) and 2-(1-methyl-1H-pyrazol-3-yl)acetic acid (9b)

Step 1: Synthesis of 2-(1H-pyrazol-3-yl)acetohydrazide

5-Nitropyridin-2-ol (2 g, 14.3 mmol) and hydrazine hydrate (5 mL) were added in a 25 mL single-neck flask, and the mixture was heated to react at 100° C. for 3 hours. After completion of the reaction, solvent was removed in vacuo to afford a product (red oil, 2 g), which was used for the next step directly.

Step 2: Synthesis of 2-(1H-pyrazol-3-yl)acetic acid 2-(1H-Pyrazol-3-yl)acetohydrazide (2 g, 14.2 mmol) and concentrated hydrochloric acid (50 mL) were added in a 25 mL single-neck flask, and the mixture was heated to react at 100° C. for 3 hours. After completion of the reaction, insoluble solids were removed by filtration and the filtrate was concentrated in vacuo to obtain a product as yellow solid, which was used for the next step directly.

Step 3: Synthesis of ethyl 2-(1H-pyrazol-3-yl)acetate 2-(1H-Pyrazol-3-yl)acetic acid (200 mg, 1.59 mmol), anhydrous ethyl alcohol (20 mL) and concentrated sulfuric acid (0.5 mL) were added in a 25 mL single-neck flask, and the mixture was heated to react at 80° C. overnight. After completion of the reaction, the solution was cooled to room temperature, neutralized with saturated sodium bicarbonate, extracted with ethyl acetate (3*20 mL), and purified by a silica gel column to afford a product (orange oil, 180 mg), with a yield of 73.7%. $^1$H NMR (400 MHz, CDCl$_3$) δ 7.54 (s, 1H), 6.25 (s, 1H), 4.18 (q, J=7.1 Hz, 2H), 3.74 (s, 2H), 1.26 (t, J=7.1 Hz, 3H). MS (ESI) m/z: 155.1 (M+1).

Step 4: Synthesis of ethyl 2-(1-methyl-1H-pyrazol-3-yl)acetate and ethyl 2-(1-methyl-1H-pyrazol-5-yl)acetate Ethyl 2-(1H-pyrazol-3-yl)acetate (180 mg, 1.17 mmol), caesium carbonate (762 mg, 2.34 mmol) and N,N-dimethylformamide (2 mL) were added in a 25 mL single-neck flask. After cooling in an ice bath, methyl iodide (332 mg, 2.34 mmol) was added dropwise, and the reaction was continued for 2 hours in an ice bath. After completion of the reaction monitored by TLC, water (20 mL) was added. Then mixture was extracted with ethyl acetate (3*10 mL), and the organic layers were combined and dried over anhydrous sodium sulfate. Solvent was removed in vacuo to afford a mixture of ethyl 2-(1-methyl-1H-pyrazol-3-yl)acetate and ethyl 2-(1-methyl-1H-pyrazol-5-yl)acetate (yellow oil, 136 mg).

Step 5: 2-(1-Methyl-1H-pyrazol-5-yl)acetic acid and 2-(1-methyl-1H-pyrazol-3-yl)acetic acid The mixture of ethyl 2-(1-methyl-1H-pyrazol-3-yl)acetate and ethyl 2-(1-methyl-1H-pyrazol-5-yl)acetate (136 mg, 0.81 mmol), lithium hydroxide monohydrate (102 mg, 2.43 mmol) and ethanol/H$_2$O (2 mL/0.5 mL) were added in a 25 mL single-neck flask, and the mixture was reacted at room temperature for 0.5 hour. After completion of the reaction, ethanol was removed under reduced pressure, then water (2 mL) was added. The mixture was adjusted to pH 3 with 1N hydrochloric acid and extracted with ethyl acetate (3*10 mL). The organic layers were combined, dried over anhydrous sodium sulfate, and concentrated in vacuo to remove the solvent to give a product (yellow oil, 100 mg).

Step 6: Synthesis of N-(2,6-dichloro-3'-cyano-4'-isobutyl-[1,1'-biphenyl]-4-yl)-2-(1-methyl-1H-pyrazol-3-yl)acetamide (9A) and N-(2,6-dichloro-3'-cyano-4'-isobutyl-[1,1'-biphenyl]-4-yl)-2-(1-methyl-1H-pyrazol-5-yl)acetamide (9B)

4'-Amino-2',6'-dichloro-4-isobutyl-[1,1'-biphenyl]-3-carbonitrile (40 mg, 0.13 mmol), the mixture of 2-(1-methyl-1H-pyrazol-5-yl)acetic acid and 2-(1-methyl-1H-pyrazol-3-yl)acetic acid (44 mg, 0.32 mmol), HATU (118 mg, 0.38 mmol), N,N-diisopropylethylamine (50 mg, 0.39 mmol) and dichloromethane (2 mL) were added in a 25 mL single-neck flask, and the mixture was reacted at room temperature for 4 hours. The resulting crude product was separated by preparative thin layer chromatography (petroleum ether: ethyl acetate=1:1) to give N-(2,6-dichloro-3'-cyano-4'-isobutyl-[1,1'-biphenyl]-4-yl)-2-(1-methyl-1H-pyrazol-3-yl)acetamide (white solid, 26 mg), $^1$H NMR (400 MHz, CDCl$_3$) δ 9.23 (s, 1H), 7.66 (s, 2H), 7.47 (s, 1H), 7.33 (t, J=7.4 Hz, 4H), 6.19 (s, 1H), 3.93 (s, 3H), 3.75 (s, 2H), 2.75 (d, J=7.3 Hz, 2H), 2.02-1.97 (m, 1H), 0.97 (d, J=6.6 Hz, 6H). MS (ESI) m/z: 441.0 (M+1) and N-(2,6-dichloro-3'-cyano-4'-isobutyl-[1,1'-biphenyl]-4-yl)-2-(1-methyl-1H-pyrazol-5-yl)acetamide (white solid, 27 mg), $^1$H NMR (400 MHz, CDCl$_3$) δ 8.26 (s, 1H), 7.63 (s, 2H), 7.47 (d, J=3.3 Hz, 2H), 7.34 (s, 2H), 6.26 (s, 1H), 3.87 (s, 3H), 3.80 (s, 2H), 2.75 (d, J=7.3 Hz, 2H), 1.97-1.88 (m, 1H), 0.97 (d, J=6.6 Hz, 6H). MS (ESI) m/z: 440.9 (M+1).

Example 10

2-(4-Cyanophenyl)-N-(2,6-dichloro-3'-cyano-4'-isobutyl-[1,1'-biphenyl]-4-yl)acetamide

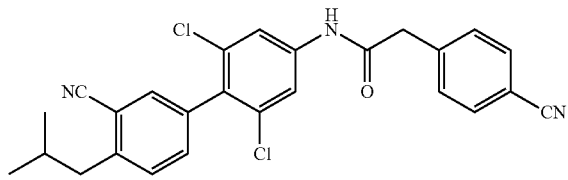 [SMILES: CC(C)Cc1ccc(-c2c(Cl)cc(NC(=O)Cc3ccc(C#N)cc3)cc2Cl)cc1C#N]

4'-Amino-2',6'-dichloro-4-isobutyl-[1,1'-biphenyl]-3-carbonitrile (30 mg, 0.09 mmol), 2-(4-cyanophenyl)acetic acid (18 mg, 0.11 mmol), HATU (43 mg, 0.11 mmol), N,N-diisopropylethylamine (47 μL, 0.28 mmol) and dichloromethane (5 mL) were added in a single-neck flask, and the mixture was reacted at room temperature overnight. After the materials had all reacted when being determined by TLC, dichloromethane (20 mL) was added, and the mixture was washed with saturated ammonium chloride (30 mL), and the organic layer was concentrated in vacuo to remove the solvent. The resulting crude product was separated by a silica gel column (petroleum ether:ethyl acetate=2:1) to give a product (white solid, 20 mg), with a yield of 48.1%. $^1$H NMR (400 MHz, CDCl$_3$) δ 7.93 (s, 1H), 7.69-7.57 (m, 5H), 7.47 (s, 1H), 7.42-7.37 (m, 2H), 7.35 (s, 1H), 3.79 (s, 2H), 2.76 (d, J=7.2 Hz, 2H), 2.04 (q, J=13.6, 6.6 Hz, 1H), 0.98 (d, J=6.6 Hz, 6H). MS (ESI) m/z: 462.1 (MH+)

Example 11

2-(2-Cyanophenyl)-N-(2,6-dichloro-3'-cyano-4'-isobutyl-[1,1'-biphenyl]-4-yl)acetamide

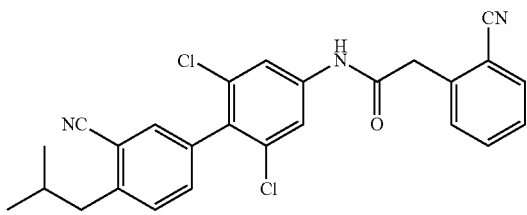 [SMILES: CC(C)Cc1ccc(-c2c(Cl)cc(NC(=O)Cc3ccccc3C#N)cc2Cl)cc1C#N]

The method is the same as in Example 1. 4'-Amino-2',6'-dichloro-4-isobutyl-[1,1'-biphenyl]-3-carbonitrile (50 mg, 0.16 mmol), 2-(2-cyanophenyl)acetic acid (30 mg, 0.19 mmol), HATU (72 mg, 0.19 mmol), N,N-diisopropylethylamine (62 mg, 0.48 mmol) and dichloromethane (2 mL) were reacted at room temperature overnight, and the crude product was separated by a silica gel column (petroleum ether:ethyl acetate=1:1) to give a product (white solid, 60 mg), with a yield of 83.3%. $^1$H NMR (400 MHz, CDCl$_3$) δ 7.86 (d, J=54.7 Hz, 1H), 7.71 (d, J=7.7 Hz, 1H), 7.68 (s, 2H), 7.64 (d, J=7.4 Hz, 1H), 7.60 (d, J=7.7 Hz, 1H), 7.51-7.41 (m, 2H), 7.35 (s, 2H), 3.96 (s, 2H), 2.77 (d, J=7.3 Hz, 2H), 2.11-1.99 (m, 1H), 0.99 (d, J=6.5 Hz, 6H). MS (ESI) m/z: 462.0 (M+1).

Example 12

2-(3-cyanophenyl)-N-(2,6-dichloro-3'-cyano-4'-isobutyl-[1,1'-biphenyl]-4-yl)acetamide

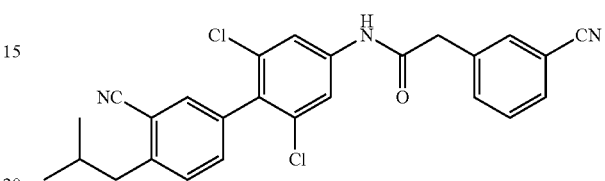

The method is the same as in Example 1. 4'-Amino-2',6'-dichloro-4-isobutyl-[1,1'-biphenyl]-3-carbonitrile (50 mg, 0.16 mmol), 2-(3-cyanophenyl)acetic acid (30 mg, 0.19 mmol), HATU (72 mg, 0.19 mmol), N,N-diisopropylethylamine (62 mg, 0.48 mmol) and dichloromethane (2 mL) were reacted at room temperature overnight, and the crude product was separated by a silica gel column (petroleum ether:ethyl acetate=1:1) to give a product (white solid, 64 mg), with a yield of 88.9%. $^1$H NMR (400 MHz, CDCl$_3$) δ 7.69-7.60 (m, 5H), 7.52 (t, J=7.0 Hz, 2H), 7.49 (s, 1H), 7.36 (s, 2H), 3.78 (s, 2H), 2.77 (d, J=7.1 Hz, 2H), 2.10-2.01 (m, 1H), 0.99 (d, J=6.4 Hz, 6H). MS (ESI) m/z: 462.0 (M+1).

Example 13

N-(2,6-Dichloro-3'-cyano-4'-isobutyl-[1,1'-biphenyl]-4-yl)-2-(pyridin-2-yl)acetamide

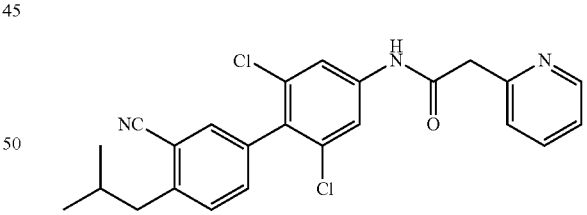

The method is the same as in Example 1. 4'-Amino-2',6'-dichloro-4-isobutyl-[1,1'-biphenyl]-3-carbonitrile (50 mg, 0.16 mmol), 2-(pyridin-2-yl)acetic acid (33 mg, 0.19 mmol), HATU (72 mg, 0.19 mmol), N,N-diisopropylethylamine (62 mg, 0.48 mmol), dichloromethane (2 mL) were reacted at room temperature for 3 hours, and the crude product was separated by a silica gel column (petroleum ether:ethyl acetate=2:1-1:1) to give a product (white solid, 17 mg), with a yield of 25%. $^1$H NMR (400 MHz, CDCl$_3$) δ 10.51 (s, 1H), 8.64 (d, J=4.7 Hz, 1H), 7.76 (d, J=7.7 Hz, 1H), 7.72 (s, 2H), 7.50 (s, 1H), 7.42-7.27 (m, 4H), 3.90 (s, 2H), 2.77 (d, J=7.3 Hz, 2H), 2.11-2.01 (m, 1H), 0.99 (d, J=6.6 Hz, 6H). MS (ESI) m/z: 438.0 (M+1).

Example 14

N-(2,6-Dichloro-3'-cyano-4'-isobutyl-[1,1'-biphenyl]-4-yl)-2-(pyridin-3-yl)acetamide

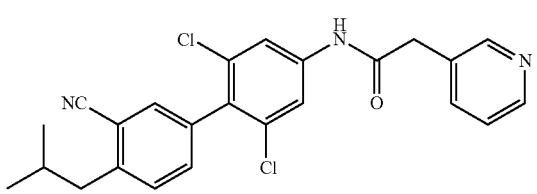 [SMILES: CC(C)Cc1ccc(-c2c(Cl)cc(NC(=O)Cc3cccnc3)cc2Cl)cc1C#N]

The method is the same as in Example 1. 4'-Amino-2',6'-dichloro-4-isobutyl-[1,1'-biphenyl]-3-carbonitrile (50 mg, 0.16 mmol), 2-(pyridin-3-yl)acetic acid (33 mg, 0.19 mmol), HATU (72 mg, 0.19 mmol), N,N-diisopropylethylamine (62 mg, 0.48 mmol) and dichloromethane (2 mL) were reacted at room temperature for 3 hours, and the crude product was separated by a silica gel column (petroleum ether:ethyl acetate=2:1-1:1) to give a product (white solid, 44 mg), with a yield of 64.7%. $^1$H NMR (400 MHz, CDCl$_3$) δ 9.16 (s, 1H), 8.51 (d, J=17.2 Hz, 2H), 7.82 (d, J=7.5 Hz, 1H), 7.70 (s, 2H), 7.47 (s, 1H), 7.41-7.31 (m, 3H), 3.73 (s, 2H), 2.76 (d, J=7.1 Hz, 2H), 2.11-1.96 (m, 1H), 0.98 (d, J=6.3 Hz, 6H). MS (ESI) m/z: 438.0 (M+1).

Example 15

N-(2,6-Dichloro-3'-cyano-4'-isobutyl-[1,1'-biphenyl]-4-yl)-2-(pyridin-4-yl)acetamide

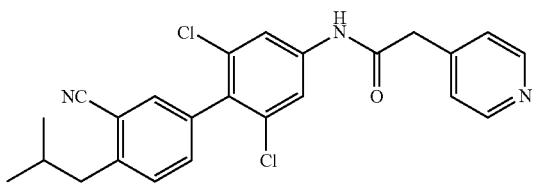 [SMILES: CC(C)Cc1ccc(-c2c(Cl)cc(NC(=O)Cc3ccncc3)cc2Cl)cc1C#N]

The method is the same as in Example 1. 4'-Amino-2',6'-dichloro-4-isobutyl-[1,1'-biphenyl]-3-carbonitrile (50 mg, 0.16 mmol), 2-(pyridin-4-yl)acetic acid (33 mg, 0.19 mmol), HATU (72 mg, 0.19 mmol), N,N-diisopropylethylamine (62 mg, 0.48 mmol) and dichloromethane (2 mL) were reacted at room temperature for 3 hours, and the crude product was separated by a silica gel column (petroleum ether:ethyl acetate=1:1-1:2) to give a product (white solid, 35 mg), with a yield of 51.5%. $^1$H NMR (400 MHz, CDCl$_3$) δ 8.99 (s, 1H), 8.58 (d, J=5.0 Hz, 2H), 7.71 (s, 2H), 7.50 (s, 1H), 7.38 (s, 2H), 7.33 (d, J=5.0 Hz, 2H), 3.77 (s, 2H), 2.79 (d, J=7.3 Hz, 2H), 2.12-1.99 (m, 1H), 1.01 (d, J=6.6 Hz, 6H). MS (ESI) m/z: 438.0 (M+1).

Example 16

N-(2,6-Dichloro-3'-cyano-4'-isobutyl-[1,1'-biphenyl]-4-yl)-2-(4-(ethylsulfonyl)phenyl)acetamide

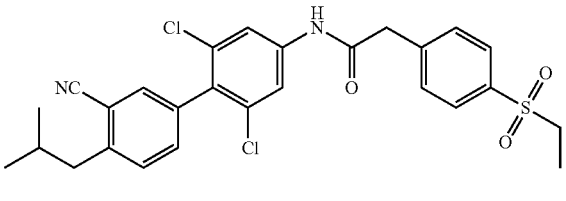 [SMILES: CCS(=O)(=O)c1ccc(CC(=O)Nc2cc(Cl)c(-c3ccc(CC(C)C)c(C#N)c3)c(Cl)c2)cc1]

Intermediate 16a: 2-(4-(ethylsulfonyl)phenyl)acetic acid

Step 1: Synthesis of 2-(4-(ethylthio)phenyl)acetic acid 2-(4-Bromophenyl)acetic acid (8.22 g, 38.2 mmol), Xantphos (1.17 g, 2.0 mmol), N,N-diisopropylethylamine (13.4 mL, 76.4 mmol) in 1,4-dioxane (100 mL) were adde to a 250 mL single-neck flask in sequence, and then Pd$_2$(dba)$_3$ (887 mg, 0.96 mmol) and ethyl mercaptan (3.45 mL, 45.9 mmol) were added under nitrogen atomosphere. The mixture was heated and reacted at reflux overnight. After the materials had all reacted when being determined by TLC, solvent was removed in vacuo, and the resulting crude product was separated by a silica gel column (petroleum ether:ethyl acetate=1:1) to give a product (yellow solid, 5.95 g), with a yield of 80.0%. MS (ESI) m/z: 195.1 (M−1).

Step 2: Synthesis of ethyl 2-(4-(ethylthio)phenyl)acetate 2-(4-(Ethylthio)phenyl)acetic acid (5.99 g, 30.5 mmol), anhydrous ethanol (100 mL), and concentrated sulfuric acid (2 mL) were added in a 250 mL single-neck flask. The mixture was heated in an oil bath to react at 90° C. for 2 hours. After the materials had all reacted when being determined by TLC, solvent was removed in vacuo, and ethyl acetate (30 mL) was added. The mixture was washed with saturated sodium carbonate (50 mL) and dried over anhydrous sodium sulfate. The filtrate was concentrated in vacuo to remove the solvent to givea product (yellow oil, 6.8 g), with a yield of 99.5%.

Step 3: Synthesis of ethyl 2-(4-(ethylsulfonyl)phenyl)acetate

Ethyl 2-(4-(ethylthio)phenyl)acetate (6.8 g, 30.4 mmol) and dichloromethane (100 mL) were added in a 250 mL single-neck flask, m-chloroperoxybenzoic acid (5.23 g, 30.4 mmol) was added slowly under an ice bath. The reaction solution was gradually warmed to room temperature, and stirred overnight. After the materials had all reacted when being determined by TLC, the reaction mixture was washed with saturated sodium carbonate (50 mL), extracted repeatedly with dichloromethane (20 mL), and the extract was dried over anhydrous sodium sulfate. The organic layers were concentrated in vacuo to remove the solvent to obtain a crude product. The crude product was separated by a silica gel column to give a product (yellow solid, 5.3 g), with a yield of 68.2%. MS (ESI) m/z: 257.1 (M+1).

Step 4: Synthesis of 2-(4-(ethylsulfonyl)phenyl)acetic acid

Ethyl 2-(4-(ethylsulfonyl)phenyl)acetate (5.3 g, 20.7 mmol), ethanol (20 mL) and H$_2$O (20 mL) were added in a 100 mL single-neck flask, and then sodium hydroxide (200 mg, 5.0 mmol) was added slowly, and the mixture was stirred for 4 hours. After the materials had all reacted when being determined by TLC, the organic solvent was removed in vacuo, then the solution was adjusted to pH 2-3 using diluted hydrochloric acid. White solids were precipitated, filtered and dried in vacuo overnight to give a product (white solid, 4.5 g), with a yield of 95.6%. $^1$H NMR (400 MHz, DMSO) δ 12.56 (s, 1H), 7.88 (d, J=8.3 Hz, 2H), 7.61 (d, J=8.3 Hz, 2H), 3.80 (s, 2H), 3.34 (dd, J=7.4 Hz, 2H), 1.15 (t, J=7.4 Hz, 2H).

Synthesis of N-(2,6-dichloro-3'-cyano-4'-isobutyl-[1,1'-biphenyl]-4-yl)-2-(4-(ethylsulfonyl)phenyl)acetamide 4'-Amino-2',6'-dichloro-4-isobutyl-[1,1'-biphenyl]-3-carbonitrile (100 mg, 0.31 mmol), 2-(4-(ethylsulfonyl)phenyl)acetic acid (79 mg, 0.34 mmol), HATU (141 mg, 0.37 mmol), N,N-diisopropylethylamine (120 mg, 0.93 mmol) and dichloromethane (5 mL) were reacted at room temperature overnight. After the materials had all reacted when being determined by TLC, dichloromethane (20 mL) was added, and the mixture was washed with saturated ammonium chloride (30 mL). The organic layer was concentrated in vacuo to obtain a crude product, and the crude product was separated by a silica gel column (petroleum ether:ethyl acetate=2:1-1:1) to give a product (white solid, 40 mg), with a yield of 24.5%. $^1$H NMR (400 MHz, CD$_3$OD) δ 7.87 (d, J=8.1 Hz, 2H), 7.77 (s, 2H), 7.61 (d, J=8.1 Hz, 2H), 7.53 (s, 1H), 7.44 (q, J=8.1 Hz, 2H), 3.84 (s, 2H), 3.18 (q, J=7.4 Hz, 2H), 2.75 (d, J=7.3 Hz, 2H), 2.02-1.95 (m, 1H), 1.20 (t, J=7.4 Hz, 3H), 0.97 (d, J=6.6 Hz, 6H). MS (ESI) m/z: 529.0 (M+1).

Example 17

N-(2,6-Dichloro-3'-cyano-4'-isobutyl-[1,1'-biphenyl]-4-yl)-2-(4-(methyl sulfonyl)phenyl)acetamide

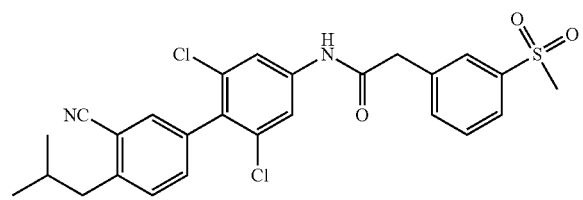 [SMILES: CC(C)Cc1ccc(-c2c(Cl)cc(NC(=O)Cc3cccc(S(C)(=O)=O)c3)cc2Cl)cc1C#N]

4'-Amino-2',6'-dichloro-4-isobutyl-[1,1'-biphenyl]-3-carbonitrile (30 mg, 0.09 mmol), 2-(4-(methylsulfonyl)phenyl) acetic acid (40 mg, 0.19 mmol), HATU (72 mg, 0.19 mmol), N,N-diisopropylethylamine (47 μL, 0.28 mmol) and dichloromethane (5 mL) were added in a 25 mL single-neck flask, and the mixture was reacted at room temperature overnight. After the materials had all reacted when being determined by TLC, dichloromethane (20 mL) was added, and the mixture was washed with saturated ammonium chloride (30 mL). The organic layer was concentrated in vacuo to obtain a crude product, and the crude product was separated by a silica gel column (petroleum ether:ethyl acetate=1:1) to give the product (white solid, 25 mg), with a yield of 45.6%. $^1$H NMR (400 MHz, CDCl$_3$) δ 7.92 (d, J=8.2 Hz, 2H), 7.88 (s, 1H), 7.67 (s, 2H), 7.54 (d, J=8.1 Hz, 2H), 7.49 (d, J=8.1 Hz, 2H), 2.76 (d, J=7.3 Hz, 2H), 2.10-1.99 (m, 1H), 0.99 (d, J=6.6 Hz, 6H). MS (ESI) m/z: 515.1 (MH+).

Example 18

N-(2,6-Dichloro-3'-cyano-4'-isobutyl-[1,1'-biphenyl]-4-yl)-2-(3-(methyl sulfonyl)phenyl)acetamide

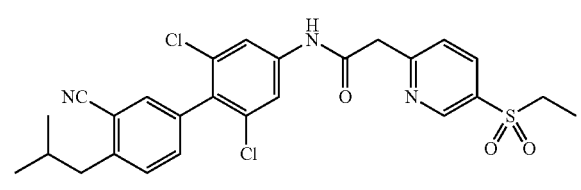 [SMILES: CCS(=O)(=O)c1ccc(CC(=O)Nc2cc(Cl)c(-c3ccc(CC(C)C)c(C#N)c3)c(Cl)c2)nc1]

The method is the same as in example 1. 4'-Amino-2',6'-dichloro-4-isobutyl-[1,1'-biphenyl]-3-carbonitrile (50 mg, 0.16 mmol), 2-(3-(methylsulfonyl)phenyl)acetic acid (41 mg, 0.19 mmol), HATU (72 mg, 0.19 mmol), N,N-diisopropylethylamine (62 mg, 0.48 mmol) and dichloromethane (3 mL) were reacted at room temperature for 3 hours. The crude product was separated by a silica gel column (petroleum ether:ethyl acetate=1:1-1:2) to give a product (white solid, 82 mg), with a yield of 99.0%. $^1$H NMR (400 MHz, CDCl$_3$) δ 8.92 (s, 1H), 7.96 (s, 1H), 7.87 (d, J=7.8 Hz, 1H), 7.75-7.65 (m, 3H), 7.56 (t, J=7.7 Hz, 1H), 7.47 (s, 1H), 7.35 (s, 2H), 3.82 (s, 2H), 3.11 (s, 3H), 2.76 (d, J=7.2 Hz, 2H), 2.15-1.97 (m, 1H), 0.99 (d, J=6.5 Hz, 6H). MS (ESI) m/z: 512.8 (M−1).

Example 19

N-(2,6-Dichloro-3'-cyano-4'-isobutyl-[1,1'-biphenyl]-4-yl)-2-(5-(ethylsulfonyl)pyridin-2-yl)acetamide Step 1: Synthesis of 2-(5-bromopyridin-2-yl)-N-(2,6-dichloro-3'-cyano-4'-isobutyl-[1,1'-biphenyl]-4-yl)acetamide 4'-Amino-2',6'-dichloro-4-isobutyl-[1,1'-biphenyl]-3-carbonitrile (100 mg, 0.31 mmol), 2-(5-bromopyridin-2-yl) acetic acid (80 mg, 0.37 mmol), HATU (141 mg, 0.37 mmol), N,N-diisopropylethylamine (120 mg, 0.93 mmol) and dichloromethane (5 mL) were added in a 25 mL single-neck flask, and the mixture was reacted at room temperature for 3 hours. Then dichloromethane (10 mL) was added, and the mixture was washed with saturated ammonium chloride, and then with saturated sodium chloride solution. The organic layer was dried over anhydrous sodium sulfate and concentrated in vacuo to remove the solvent to obtain a crude product (200 mg), which was used for the next step directly.

Step 2: Synthesis of N-(2,6-dichloro-3'-cyano-4'-isobutyl-[1,1'-biphenyl]-4-yl)-2-(5-(ethylthio)pyridin-2-yl)acetamide 2-(5-Bromopyridin-2-yl)-N-(2,6-dichloro-3'-cyano-4'-isobutyl-[1,1'-biphenyl]-4-yl)acetamide (200 mg, 0.39 mmol), N,N-diisopropylethylamine (101 mg, 0.78 mmol), Xantphos (11 mg, 0.02 mmol), Pd$_2$(dba)$_3$ (16 mg, 0.02 mmol), ethyl mercaptan (36 mg) and 1,4-dioxane (5 mL) were added in a microwave tube, and the mixture was reacted for 2 hours under microwave at 120° C. The mixture was separated by a silica gel column (petroleum ether:ethyl acetate=5:1) to give a product (yellow oil, 150 mg), with a total yield of 96.1% for these two steps. $^1$H NMR (400 MHz, CDCl$_3$) δ 10.47 (s, 1H), 8.72 (s, 1H), 7.91-7.85 (m, 3H), 7.66 (s, 1H), 7.53 (q, J=8.0 Hz, 2H), 7.46 (d, J=7.9 Hz, 1H), 7.42 (d, J=1.0 Hz, 1H), 4.07 (s, 2H), 3.17 (q, J=7.4 Hz, 2H), 2.93 (d, J=7.2 Hz, 2H), 2.26-2.22 (m, 1H), 1.52 (t, J=7.4 Hz, 3H), 1.16 (d, J=6.5 Hz, 6H). MS (ESI) m/z: 498.0 (M+1).

Step 3: Synthesis of N-(2,6-dichloro-3'-cyano-4'-isobutyl-[1,1'-biphenyl]-4-yl)-2-(5-(ethylsulfonyl)pyridin-2-yl)acetamide N-(2,6-Dichloro-3'-cyano-4'-isobutyl-[1,1'-biphenyl]-4-yl)-2-(5-(ethylthio)pyridin-2-yl)acetamide (50 mg, 0.1 mmol) and dichloromethane (2 mL) were added in a 25 mL single-neck flask, then mCPBA (35 mg, 0.2 mmol) was added under an ice bath. The reaction was continued for 2 hours at room temperature under nitrogen atmosphere. After completion of the reaction, the mixture was washed with 2N sodium carbonate solution, and then with saturated sodium chloride solution. Solvent was removed in vacuo, and the residue was separated by preparative thin layer chromatography (petroleum ether:ethyl acetate=1:2) to give a product (white solid, 20 mg), with a yield of 37.8%. $^1$H NMR (400 MHz, CDCl$_3$) δ 9.60 (s, 1H), 9.03 (s, 1H), 8.15 (d, J=8.1 Hz, 1H), 7.63 (s, 2H), 7.53 (d, J=8.1 Hz, 1H), 7.42 (s, 1H), 7.33-7.24 (m, 2H), 3.96 (s, 2H), 3.13 (q, J=7.4 Hz, 2H), 2.70 (d, J=7.2 Hz, 2H), 1.97-1.91 (m, 1H), 1.31-1.26 (m, 3H), 0.92 (d, J=6.5 Hz, 7H). MS (ESI) m/z: 530.0 (M+1).

Example 20

N-(2,6-dichloro-3'-cyano-4'-isobutyl-[1,1'-biphenyl]-4-yl)-2-(5-(methylsulfonyl)pyridin-2-yl)acetamide

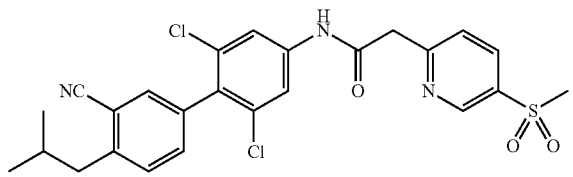 [SMILES: CC(C)Cc1ccc(-c2c(Cl)cc(NC(=O)Cc3ccc(S(C)(=O)=O)cn3)cc2Cl)cc1C#N]

Step 1: Synthesis of N-(2,6-dichloro-3'-cyano-4'-isobutyl-[1,1'-biphenyl]-4-yl)-2-(5-(methylthio)pyridin-2-yl)acetamide 2-(5-Bromopyridin-2-yl)-N-(2,6-dichloro-3'-cyano-4'-isobutyl-[1,1'-biphenyl]-4-yl)acetamide (300 mg, 0.6 mmol), N,N-diisopropylethylamine (156 mg, 1.2 mmol), Xantphos (18 mg, 0.03 mmol), Pd$_2$(dba)$_3$ (24 mg, 0.03 mmol), methyl mercaptan propylene glycol solution (10%, 0.5 mL) and 1,4-dioxane (5 mL) were added in a microwave tube, and the mixture was reacted for 2 hours under microwave at 100° C. The mixture was separated by a silica gel column (petroleum ether:ethyl acetate=2:1-1:2) to give a product (yellow oil, 220 mg), with a yield of 75.9%. $^1$H NMR (400 MHz, CDCl$_3$) δ 10.20 (s, 1H), 8.50 (d, J=2.1 Hz, 1H), 7.69 (s, 2H), 7.60 (dd, J=8.2, 2.4 Hz, 1H), 7.49 (d, J=1.3 Hz, 1H), 7.38-7.31 (m, 2H), 7.23 (d, J=8.2 Hz, 1H), 3.84 (s, 2H), 2.75 (d, J=7.3 Hz, 2H), 2.53 (s, 3H), 2.03-1.98 (m, 1H), 0.98 (d, J=6.6 Hz, 6H). MS (ESI) m/z: 484.0 (M+1).

Step 2: Synthesis of N-(2,6-dichloro-3'-cyano-4'-isobutyl-[1,1'-biphenyl]-4-yl)-2-(5-(methylsulfonyl)pyridin-2-yl)acetamide N-(2,6-Dichloro-3'-cyano-4'-isobutyl-[1,1'-biphenyl]-4-yl)-2-(5-(ethylthio)pyridin-2-yl)acetamide (48 mg, 0.1 mmol) and dichloromethane (2 mL) were added in a 25 mL single-neck flask, then mCPBA (35 mg, 0.2 mmol) was added under an ice bath. The mixture was reacted for 2 hours at room temperature under nitrogen atmosphere. After completion of the reaction, the mixture was washed with 2N sodium carbonate solution, and then with saturated sodium chloride solution. Solvent was removed in vacuo, and the residue was separated by preparative thin layer chromatography (petroleum ether:ethyl acetate=1:1) to give a product (white solid, 18 mg), with a yield of 34.6%. $^1$H NMR (400 MHz, CDCl$_3$) δ 9.60 (s, 1H), 9.15 (d, J=2.1 Hz, 1H), 8.26 (dd, J=8.2, 2.3 Hz, 1H), 7.69 (s, 2H), 7.59 (d, J=8.2 Hz, 1H), 7.48 (s, 1H), 7.39-7.30 (m, 2H), 4.02 (s, 2H), 3.14 (s, 3H), 2.75 (d, J=7.3 Hz, 2H), 2.03-1.97 (m, 1H), 0.97 (d, J=6.6 Hz, 6H). MS (ESI) m/z: 515.8 (M+1).

Example 21

N-(2,6-Dichloro-3'-cyano-4'-isobutyl-[1,1'-biphenyl]-4-yl)-2-(4-sulfamoylphenyl)acetamide

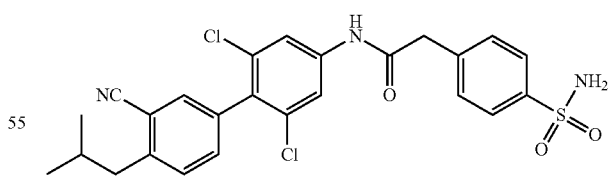

Step 1: Synthesis of 2-(4-(benzylthio)phenyl)acetic acid 2-(4-Bromophenyl)acetic acid (1 g, 4.65 mmol), N,N-diisopropylethylamine (960 mg, 7.44 mmol), Xantphos (135 mg, 0.23 mmol), Pd$_2$(dba)$_3$ (95 mg, 0.12 mmol), phenylmethanethiol (577 mg, 4.65 mmol) and 1,4-dioxane (50 mL) were added in a 100 mL single-neck flask, and the mixture was heated to react at 100° C. for 6 hours. After completion of the reaction, solvent was removed directly in vacuo, and the residue was mixed with silica gel and separated by a silica gel column (dichloromethane:methanol=20:1) to give a product (yellow solid, 1.5 g), with a yield of 62.5%. $^1$H NMR (400 MHz, DMSO-$d_6$) δ 12.30 (s, 1H), 7.32 (d, J=7.6 Hz, 2H), 7.29-7.21 (m, 4H), 7.20 (d, J=7.2 Hz, 1H), 7.14 (d, J=8.1 Hz, 2H), 4.18 (s, 2H), 3.48 (s, 2H).

Step 2: Synthesis of methyl 2-(4-(benzylthio)phenyl)acetate 2-(4-(Benzylthio)phenyl)acetic acid (1 g, 3.87 mmol), methanol (10 mL) and sulfuryl chloride (0.5 mL) were added in a 25 mL single-neck flask, and the mixture was heated to react at 60° C. for 3 hours. After completion of the reaction, solvent was removed in vacuo, and water (20 mL) was added, then the mixture was extracted with ethyl acetate (3*10 mL). The combined organic layers were dried over anhydrous sodium sulfate, and concentrated in vacuo to remove the solvent to obtain a product (yellow solid, 1 g), with a yield 95.2%. MS (ESI) m/z: 273.0 (M+1).

Step 3: Synthesis of methyl 2-(4-(chlorosulfonyl)phenyl)acetate

Methyl 2-(4-(benzylthio)phenyl)acetate (544 mg, 2 mmol), tetrahydrofuran (5 mL), acetic acid (0.58 mL) and $H_2O$ (0.14 mmol) were added in a 25 mL single-neck flask. The mixture was stirred under an ice bath for 5 minutes, then thionyl chloride (0.64 mmol) was added dropwise slowly. After completion of addition, the mixture was kept in an ice bath for 5 minutes and then reacted at room temperature for 2 hours. After completion of the reaction, the mixture was extracted with ethyl acetate (3*20 mL), and separated by a silica gel column (petroleum ether:ethyl acetate=20:1) to give a product (orange oil, 330 mg). $^1$H NMR (400 MHz, CDCl$_3$) δ 8.00 (d, J=8.5 Hz, 2H), 7.54 (d, J=8.4 Hz, 2H), 3.75 (s, 2H), 3.73 (s, 3H).

Step 4: Synthesis of methyl 2-(4-sulfamoylphenyl)acetate

Methyl 2-(4-(chlorosulfonyl)phenyl)acetate (330 mg, 1.33 mmol), tetrahydrofuran (5 mL) and triethylamine (267 mg, 2.66 mmol) were added in a 25 mL single-neck flask, then ammonia water (150 mg, 2.66 mmol) was added under stirring, and the mixture was reacted at room temperature for 10 minutes. After completion of the reaction according to TLC, water (10 mL) was added, and the mixture was extracted with ethyl acetate (3*10 mL), and the extract was washed once with saturated sodium chloride, dried over anhydrous sodium sulfate, and concentrated in vacuo to obtain a product (white solid, 300 mg), with a yield of 98.7%. $^1$H NMR (400 MHz, DMSO-$d_6$) δ 7.78 (d, J=6.6 Hz, 2H), 7.47 (d, J=7.6 Hz, 2H), 3.81 (s, 2H), 3.64 (s, 3H). MS (ESI) m/z: 230.0 (M+1).

Step 5: Synthesis of 2-(4-sulfamoylphenyl)acetic acid

Methyl 2-(4-sulfamoylphenyl)acetate (50 mg, 0.22 mmol), lithium hydroxide monohydrate (28 mg, 0.66 mmol) and ethanol/$H_2O$ (1 mL/0.2 mL) were added in a 25 mL single-neck flask, and the mixture was reacted at room temperature for 30 minutes. After completion of the reaction according to TLC, the mixture was concentrated in vacuo to remove ethanol, and water (10 mL) was added. Then the solution was adjusted to acidic with 1N hydrochloric acid, extracted with ethyl acetate (3*10 mL), washed with saturated sodium chloride, and concentrated in vacuo to remove the solvent to afford a product (white solid, 35 mg), with a yield of 74.5%. $^1$H NMR (400 MHz, DMSO-$d_6$) δ 12.44 (s, 1H), 7.72 (d, J=8.2 Hz, 2H), 7.41 (d, J=8.2 Hz, 2H), 7.29 (s, 2H), 3.65 (s, 2H).

Step 6: Synthesis of N-(2,6-dichloro-3'-cyano-4'-isobutyl-[1,1'-biphenyl]-4-yl)-2-(4-sulfamoylphenyl) acetamide The method is the same as in example 1. 4'-Amino-2',6'-dichloro-4-isobutyl-[1,1'-biphenyl]-3-carbonitrile (53 mg, 0.17 mmol), 2-(4-sulfamoylphenyl)acetic acid (30 mg, 0.14 mmol), HATU (65 mg, 0.17 mmol), N,N-diisopropylethylamine (54 mg, 0.42 mmol) and dichloromethane (2 mL) were reacted at room temperature for 3 hours, and the crude product was separated by a silica gel column (petroleum ether:ethyl acetate=1:2) to give a product (white solid, 58 mg), with a yield of 80.5%. $^1$H NMR (400 MHz, DMSO-$d_6$) δ 10.67 (s, 1H), 7.82 (s, 2H), 7.79 (d, J=8.2 Hz, 2H), 7.75 (s, 1H), 7.54 (s, 2H), 7.51 (d, J=8.1 Hz, 3H), 7.35 (s, 2H), 3.81 (s, 2H), 2.73 (d, J=7.3 Hz, 2H), 2.03-1.93 (m, 1H), 0.93 (d, J=6.6 Hz, 6H). MS (ESI) m/z: 513.8 (M−1).

Example 22

N-(2,6-Dichloro-3'-cyano-4'-isobutyl-[1,1'-biphenyl]-4-yl)-2-(4-(N-methyl sulfamoyl)phenyl)acetamide

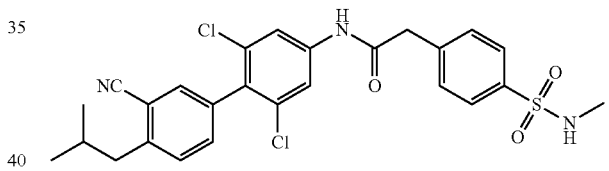

Intermediate 22a: Synthesis of 2-(4-(N-methyl sulfonamido)phenyl)acetic acid

Step 1: Synthesis of 2-(4-(benzylthio)phenyl)acetic acid 2-(4-Bromophenyl)acetic acid (500 mg, 2.3 mmol), Xantphos (266 mg, 0.46 mmol) and N,N-diisopropylethylamine (0.9 mL, 4.66 mmol) in 1,4-dioxane (10 mL) were added to a 50 mL single-neck flask in sequence, and then Pd$_2$(dba)$_3$ (210 mg, 0.23 mmol) and phenylmethanethiol (0.33 mL, 2.8 mmol) were added under argon atmosphere. The mixture was heated to reflux for 8 hours. After the materials had all reacted when being determined by TLC, solvent was removed in vacuo to obtain a crude product, and saturated brine (20 mL) was added, then the mixture was washed with ethyl acetate (10 mL). The combined organic layers were concentrated in vacuo to give a product (yellow green solid, 400 mg), with a yield of 66.5%. MS (ESI) m/z: 257.1 (M−1).

Step 2: Synthesis of 2-(4-(chlorosulfonyl)phenyl)acetic acid 2-(4-(Benzylthio)phenyl)acetic acid (400 mg, 1.6 mmol), dichloromethane (10 mL), $H_2O$ (86 μL, 6.2 mmol), acetic acid (341 μL, 7.8 mmol) and thionyl chloride (387 μL, 6.2 mmol) were added to a 50 mL single-neck flask under an ice bath. The mixture was stirred under an ice bath for 5 minutes, then warmed to room temperature and reacted for 20 minutes. After the materials had all reacted when being determined by TLC, water (1 mL) was added to quench the reaction, and the mixture was extracted with ethyl acetate. The combined organic layers were concentrated in vacuo to obtain a crude product, which was used for next step directly. MS (ESI) m/z: 233.0 (M−1).

Step 3: 2-(4-(N-Methylsulfamoyl)phenyl)acetic acid 2-(4-(Chlorosulfonyl)phenyl)acetic acid (1.6 mmol) and methylamino alcohol solution (1 mL) were added to a 50 mL single-neck flask under an ice bath, and the mixture was reacted for 1 hour. After completion of the reaction according to TLC, water (10 mL) was added and the mixture was extracted with dichloromethane (5 mL). The organic layers were combined and concentrated in vacuo. The crude product was separated by a silica gel column (petroleum ether:ethyl acetate=4:1) to give a product (90 mg), with a yield of 24.5%. MS (ESI) m/z: 230.0 (MH+)

Synthesis of N-(2,6-dichloro-3'-cyano-4'-isobutyl-[1,1'-biphenyl]-4-yl)-2-(4-(N-methylsulfamoyl)phenyl)acetamide 4'-Amino-2',6'-dichloro-4-isobutyl-[1,1'-biphenyl]-3-carbonitrile (125 mg, 0.39 mmol), 2-(4-(N-methylsulfamoyl)phenyl)acetic acid (90 mg, 0.39 mmol), HATU (180 mg, 0.47 mmol), N,N-diisopropylethylamine (135 μL, 0.79 mmol) and dichloromethane (5 mL) were added in a 25 mL single-neck flask. The mixture was reacted at room temperature for 4 hours. After the materials had all reacted when being determined by TLC, dichloromethane (20 mL) was added, and the mixture was washed with saturated ammonium chloride (30 mL). The organic layer was concentrated in vacuo to remove the solvent, and the resulting crude product was separated by a silica gel column (petroleum ether:ethyl acetate=1:1.5) to give a product (white solid, 18 mg), with a yield of 8.7%. $^1$H NMR (400 MHz, CDCl$_3$) δ 8.36 (s, 1H), 7.83 (d, J=7.9 Hz, 2H), 7.69 (s, 2H), 7.50 (d, J=8.0 Hz, 2H), 7.47 (s, 1H), 7.35 (s, 2H), 3.81 (s, 2H), 2.76 (d, J=7.3 Hz, 2H), 2.67 (s, 3H), 2.09-2.00 (m, 1H), 0.98 (d, J=6.6 Hz, 6H). MS (ESI) m/z: 530.1 (M+1).

Example 23

N-(2,6-Dichloro-3'-cyano-4'-isobutyl-[1,1'-biphenyl]-4-yl)-2-(4-(dimethylphosphoryl)phenyl)acetamide

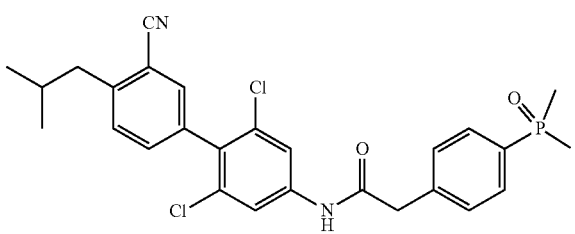 [SMILES: CC(C)Cc1ccc(-c2c(Cl)cc(NC(=O)Cc3ccc(P(C)(C)=O)cc3)cc2Cl)cc1C#N]

Step 1: Synthesis of ethyl 2-(4-iodophenyl)acetate

Ethyl 2-(4-aminophenyl)acetate (895 mg, 5 mmol), water (8 mL) and concentrated sulfuric acid (1.2 mL) were added in a 50 mL single-neck flask, and the mixture was cooled to 0° C., then a solution of sodium nitrite (414 mg, 6 mmol) in water (2 mL) was added slowly. The reaction mixture was kept at 0° C. for 0.5 hours, then a cooled solution of potassium iodide (1.66 g, 10 mmol) in water (6 mL) was added, and the reaction was continued at 0° C. for 2.5 hours. The reaction mixture was extracted with ethyl acetate (3*50 mL), and the organic layers were combined, washed with 5% aqueous HCl (2*20 mL) and then with saturated sodium bisulfite (2*50 mL), dried over anhydrous sodium sulfate, and filtered. The filtrate was concentrated in vacuo to remove the solvent, and the residue was separated by a silica gel column (petroleum ether:ethyl acetate=10:1-1:1) to give a product (white solid, 942 mg), with a yield of 65%, which was used for the next step directly.

Step 2: Synthesis of ethyl 2-(4-(dimethylphosphoryl)phenyl)acetate

Ethyl 2-(4-iodophenyl)acetate (290 mg, 1 mmol), dimethylphosphine oxide (156 mg, 2 mmol), Pd$_2$(dba)$_3$ (4.5 mg, 0.005 mmol), Xantphos (5.8 mg, 0.01 mmol), triethylamine (303 mg, 3 mmol) and 1,4-dioxane (5 mL) were added in a 25 mL single-neck flask, and the mixture was reacted at room temperature for 2 hours. Then solvent was removed in vacuo, and the crude product was separated by a silica gel column (petroleum ether:ethyl acetate=10:1-1:1) to give a product (oil, 200 mg), with a yield of 83.3. MS (ESI) m/z: 241 (M+1).

Step 3: Synthesis of 2-(4-(dimethylphosphoryl)phenyl)acetic acid

Ethyl 2-(4-(dimethylphosphoryl)phenyl)acetate (0.72 g, 3 mmol) and methanol/H$_2$O (4:1, 10 mL) were added in a 25 mL single-neck flask, then 3N aqueous sodium hydroxide solution (5 mL, 15 mmol) was added slowly at room temperature. The reaction was continued at room temperature for 4 hours, and the mixture was filtered to afford a crude product (whild solid, 450 mg), with a yield of 70.7%. The product was not further purified but used for the next step directly. MS (ESI) m/z: 235 (M+Na).

Step 4: Synthesis of N-(2,6-dichloro-3'-cyano-4'-isobutyl-[1,1'-biphenyl]-4-yl)-2-(4-(dimethylphosphoryl)phenyl)acetamide The method is the same as in example 1. 4'-Amino-2',6'-dichloro-4-isobutyl-[1,1'-biphenyl]-3-carbonitrile (60 mg, 0.19 mmol), 2-(4-(dimethylphosphoryl)phenyl)acetic acid (60 mg, 0.28 mmol), HATU (144 mg, 0.38 mmol), N,N-diisopropylethylamine (74 mg, 0.57 mmol) and dichloromethane (5 mL) were reacted at room temperature for 3 hours. The crude product was separated by silico gel column and preparative thin layer chromatography to give a product (white solid, 60 mg), with a yield of 61.8%. $^1$H NMR (400 MHz, CDCl$_3$) δ 9.14 (s, 1H), 7.78 (s, 2H), 7.66 (dd, J=11.5, 8.0 Hz, 2H), 7.50 (d, J=7.0 Hz, 2H), 7.47 (s, 1H), 7.35 (s, 2H), 3.81 (s, 2H), 3.74-3.64 (m, 1H), 3.16 (d, J=7.4 Hz, 1H), 2.76 (d, J=7.3 Hz, 2H), 1.79 (d, J=13.1 Hz, 7H), 0.99 (d, J=6.6 Hz, 6H). MS (ESI) m/z: 510.9 (M−1).

Example 24

4-(2-((2,6-Dichloro-3'-cyano-4'-isobutyl-[1,1'-biphenyl]-4-yl)amino)-2-oxoethyl)benzoic acid

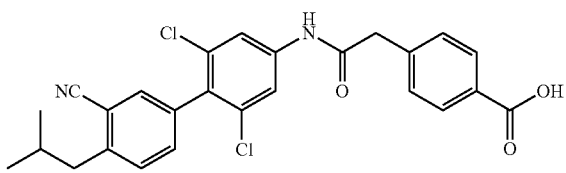 [SMILES: CC(C)Cc1ccc(-c2c(Cl)cc(NC(=O)Cc3ccc(C(=O)O)cc3)cc2Cl)cc1C#N]

Synthesis of intermediate 5a: 2-(4-((methoxy) carbonyl) phenyl) acetic acid Step 1: Synthesis of methyl 4-(2-methoxy-2-oxoethyl)benzoate 4-(Carboxymethyl)benzoic acid (200 mg, 1.1 mmol), methanol (10 mL) and concentrated sulfuric acid (1 mL) were added in a 25 mL single-neck flask, and the mixture was heated to reflux overnight. After the materials had all reacted when being determined by TLC, saturated sodium carbonate aqueous solution was added to neutralize the acid and the solution was extracted with ethyl acetate to obtain a crude product (white solid, 210 mg), with a yield 91.0%. $^1$H NMR (400 MHz, CDCl$_3$) δ 7.98 (d, J=8.2 Hz, 2H), 7.34 (d, J=8.1 Hz, 2H), 3.89 (s, 3H), 3.68 (s, 3H).

Step 2: Synthesis of 2-(4-(methoxycarbonyl)phenyl)acetic acid

Methyl 4-(2-methoxy-2-oxoethyl)benzoate (100 mg, 0.48 mmol), methanol (1.5 mL), water (1.5 mL) and anhydrous potassium carbonate (116 mg, 0.72 mmol) were added in a 10 mL single-neck flask, and the mixture was stirred at room temperature for 1.5 hours. After the materials had all reacted when being determined by TLC, solvent was removed in vacuo, and the residue was redissolved in ethyl acetate (1 mL) and separated by preparative thin layer chromatography (petroleum ether:ethyl acetate=1:1) to give a product (white solid, 60 mg), with a yield of 64.4%. $^1$H NMR (400 MHz, CDCl$_3$) δ 8.00 (d, J=8.1 Hz, 2H), 7.35 (d, J=8.0 Hz, 2H), 3.91 (s, 3H), 3.70 (s, 2H).

Synthesis of 4-(2-((2,6-dichloro-3'-cyano-4'-isobutyl-[1,1'-biphenyl]-4-yl)amino)-2-oxoethyl)benzoic acid Step 1: Synthesis of methyl 4-(2-((2,6-dichloro-3'-cyano-4'-isobutyl-[1,1'-biphenyl]-4-yl)amino)-2-oxoethyl)benzoate 4'-Amino-2',6'-dichloro-4-isobutyl-[1,1'-biphenyl]-3-carbonitrile (20 mg, 0.06 mmol), 2-(4-(methoxycarbonyl)phenyl)acetic acid (14.6 mg, 0.08 mmol), HATU (29 mg, 0.08 mmol), N,N-diisopropylethylamine (22 μL, 0.13 mmol) and dichloromethane (2 mL) were added into a 25 mL microwave tube, and the mixture was reacted at 80° C. for 1 hour under microwave. After the materials had all reacted when being determined by TLC, dichloromethane (20 mL) was added, and the mixture was washed with saturated ammonium chloride (30 mL). The organic layer was concentrated in vacuo to remove the solvent. The resulting crude product was separated by preparative thin layer chromatography (petroleum ether:ethyl acetate=4:1) to give a product (white solid, 17 mg), with a yield of 57.2%. MS (ESI) m/z: 495.1 (M+1).

Step 2: Synthesis of 4-(2-((2,6-dichloro-3'-cyano-4'-isobutyl-[1,1'-biphenyl]-4-yl)amino)-2-oxoethyl) benzoic acid Methyl 4-(2-((2,6-dichloro-3'-cyano-4'-isobutyl-[1,1'-biphenyl]-4-yl)amino)-2-oxoethyl)benzoate (17 mg, 0.03 mmol), lithium hydroxide monohydrate (20 mg), ethanol (4 mL), H$_2$O (2 mL) and tetrahydrofuran (0.5 mL) were added in a 25 mL single-neck flask. The reaction mixture was stirred at room temperature overnight. After the materials had all reacted when being determined by TLC, dilute hydrochloric acid was added to acidify the solution to pH 2-3, and solids were precipitated from the solution, filtered and dried in vacuo overnight to afford a product (white solid, 7.4 mg), with a yield of 51.4%. $^1$H NMR (400 MHz, CDCl$_3$) δ 8.15 (d, J=8.0 Hz, 2H), 7.60 (s, 2H), 7.50-7.41 (m, 3H), 7.35 (s, 2H), 7.14 (s, 1H), 3.84 (s, 2H), 2.77 (d, J=7.2 Hz, 2H), 2.27-2.19 (m, 1H), 0.99 (d, J=6.5 Hz, 6H). MS (ESI) m/z: 479.1 (M−1).

Example 25

2-(4-(2-((2,6-Dichloro-3'-cyano-4'-isobutyl-[1,1'-biphenyl]-4-yl)amino)-2-oxoethyl)phenyl)acetic acid

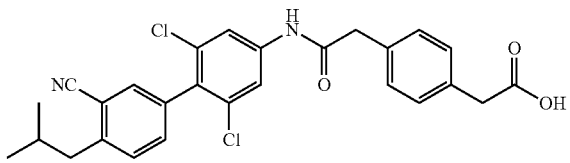 [SMILES: CC(C)Cc1ccc(-c2c(Cl)cc(NC(=O)Cc3ccc(CC(=O)O)cc3)cc2Cl)cc1C#N]

Synthesis of intermediate 25a: 2-(4-(2-methoxy-2-ethoxy) phenyl) acetic acid

Step 1: Synthesis of dimethyl 2,2'-(1,4-phenylene)diacetate 2,2'-(1,4-Phenylene)diacetic acid (200 mg, 1.0 mmol), methanol (10 mL), concentrated sulfuric acid (1 mL) were added in a 25 mL single-neck flask, and the mixture was heated to reflux overnight. After the materials had all reacted when being determined by TLC, saturated aqueous solution of sodium carbonate was added to neutralize the solution, and the mixture was extracted with ethyl acetate to obtain a crude product (white solid, 230 mg), with a yield of 100%.

Step 2: Synthesis of 2-(4-(2-methoxy-2-oxoethyl)phenyl)acetic acid

Dimethyl 2,2'-(1,4-phenylene)diacetate (230 mg, 1.0 mmol), methanol (1 mL), water (1 mL), tetrahydrofuran (1 mL) and lithium hydroxide monohydrate (20 mg) were added to a 10 mL single-neck flask, and the mixture was stirred at room temperature for 1 hour. After the materials had all reacted when being determined by TLC, solvent was removed in vacuo, and the residue was redissolved in ethyl acetate (1 mL) and separated by preparative thin layer chromatography (petroleum ether:ethyl acetate=1:1) to give a product (white solid, 100 mg), with a yield of 48.0%. MS (ESI) m/z: 207.1 (M−1).

Synthesis of 2-(4-(2-((2,6-dichloro-3'-cyano-4'-isobutyl-[1,1'-biphenyl]-4-yl)amino)-2-oxoethyl)phenyl)acetic acid Step 1: Synthesis of methyl 2-(4-(2-((2,6-dichloro-3'-cyano-4'-isobutyl-[1,1'-biphenyl]-4-yl)amino)-2-oxoethyl)phenyl)acetate 4'-Amino-2',6'-dichloro-4-isobutyl-[1,1'-biphenyl]-3-carbonitrile (70 mg, 0.22 mmol), 2-(4-(methoxy)carbonyl)phenyl)acetic acid (59 mg, 0.28 mmol), HATU (106 mg, 0.28 mmol), N,N-diisopropylethylamine (98 μL, 0.56 mmol) and dichloromethane (2 mL) were added into a 25 mL microwave tube, and the mixture was reacted at 80° C. for 1 hour under microwave. After the materials had all reacted when being determined by TLC, dichloromethane (20 mL) was added, and the mixture was washed with saturated ammonium chloride (30 mL). The organic layer was concentrated in vacuo to remove the solvent. The resulting crude product was separated by preparative thin layer chromatography (petroleum ether:ethyl acetate=4:1) to give a product (white solid, 32 mg), with a yield of 28.6%. MS (ESI) m/z: 509.1 (MH+).

Step 2: Synthesis of 2-(4-(2-((2,6-dichloro-3'-cyano-4'-isobutyl-[1,1'-biphenyl]-4-yl)amino)-2-oxoethyl)phenyl)acetic acid Methyl 2-(4-(2-((2,6-dichloro-3'-cyano-4'-isobutyl-[1,1'-biphenyl]-4-yl)amino)-2-oxoethyl)phenyl)acetate (32 mg, 0.06 mmol), lithium hydroxide monohydrate (20 mg), ethanol (4 mL), water (2 mL) and tetrahydrofuran (0.5 mL) were added in a 25 mL single-neck flask, and the mixture was stirred at room temperature overnight. After the materials had all reacted when being determined by TLC, dilute hydrochloric acid was added to acidify the solution to pH 2-3, and solids were precipitated from the solution, filtered and dried in vacuo overnight to afford a product (white solid, 11 mg), with a yield of 37.1%. $^1$H NMR (400 MHz, CDCl$_3$) δ 7.57 (s, 2H), 7.47 (s, 1H), 7.39-7.33 (m, 4H), 7.33-7.28 (m, 2H), 3.75 (s, 2H), 3.70 (s, 2H), 2.76 (d, J=7.4 Hz, 2H), 2.08-1.98 (m, 1H), 0.98 (d, J=6.6 Hz, 6H). MS (ESI) m/z: 493.1 (M−1).

Example 26

N-(2,6-Dichloro-4'-isobutyl-[1,1'-biphenyl]-4-yl)-2-(4-(ethylsulfonyl)phenyl)acetamide

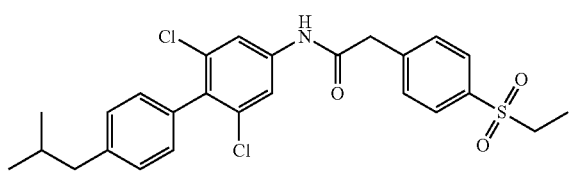 [SMILES: CCS(=O)(=O)c1ccc(CC(=O)Nc2cc(Cl)c(-c3ccc(CC(C)C)cc3)c(Cl)c2)cc1]

Step 1: Synthesis of 2,6-dichloro-4'-isobutyl-4-nitro-1,1'-biphenyl (4-Isobutylphenyl)boronic acid (300 mg, 1.68 mmol), 1,3-dichloro-2-iodo-5-nitrobenzene (636 mg, 2 mmol), potassium carbonate (680 mg, 5 mmol), PdCl$_2$(dtbpf) (55 mg, 0.08 mmol) and 2 wt % Tween 20 in water (10 mL) were added in a 20 mL single-neck flask, and the mixture was heated to react at 80° C. for 1 hour. After completion of the reaction, the mixture was extracted with ethyl acetate (3*10 mL). The combined organic layers were concentrated in vacuo to remove the solvent, and the residue was separated by a silica gel column (elutent:petroleum ether) to give a product (colorless oil, 300 mg), with a yield of 54.9%.

Step 2: 2,6-Dichloro-4'-isobutyl-[1,1'-biphenyl]-4-amine 2,6-Dichloro-4'-isobutyl-4-nitro-1,1'-biphenyl (265 mg, 0.82 mmol), ammonium formate (515 mg, 8.2 mmol) and methanol/H$_2$O (10 mL/2 mL) were added in a 25 mL single-neck flask, and zinc powder (266 mg, 4.1 mmol) was added under stirring, then the mixture was heated to react at 80° C. for 2 hours. After completion of the reaction, the mixture was cooled to room temperature and extracted with ethyl acetate (3*30 mL) to afford a product (colorless oil, 260 mg), with a yield of 94.9%.

Step 3: N-(2,6-Dichloro-4'-isobutyl-[1,1'-biphenyl]-4-yl)-2-(4-(ethylsulfonyl)phenyl)acetamide The method is the same as in example 1. 2,6-Dichloro-4'-isobutyl-[1,1'-biphenyl]-4-amine (100 mg, 0.34 mmol), 2-(4-(ethylsulfonyl)phenyl)acetic acid (93 mg, 0.41 mmol), HATU (156 mg, 0.41 mmol), N,N-diisopropylethylamine (144 mg, 1.12 mmol) and dichloromethane (5 mL) were reacted at room temperature for 3 hours. The crude product was separated by a silica gel column (petroleum ether:ethyl acetate=1:2) to give a product (white solid, 46 mg), with a yield of 26.9%. $^1$H NMR (400 MHz, CDCl$_3$) δ 8.67 (s, 1H), 7.81 (d, J=8.2 Hz, 2H), 7.66 (s, 2H), 7.51 (d, J=8.2 Hz, 2H), 7.20 (d, J=8.0 Hz, 2H), 7.10 (d, J=8.0 Hz, 2H), 3.80 (s, 2H), 3.12 (q, J=7.4 Hz, 2H), 2.84 (s, 3H), 2.52 (d, J=7.2 Hz, 2H), 1.91 (dt, J=13.5, 6.8 Hz, 1H), 0.93 (d, J=6.6 Hz, 6H). MS (ESI) m/z: 504.0 (M+1).

Example 27

N-(2,6-Dichloro-3'-fluoro-4'-isobutyl-[1,1'-biphenyl]-4-yl)-2-(4-(ethylsulfonyl)phenyl)acetamide

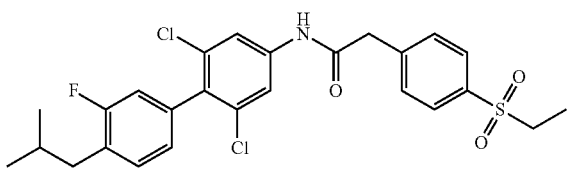 [SMILES: CCS(=O)(=O)c1ccc(CC(=O)Nc2cc(Cl)c(-c3ccc(CC(C)C)c(F)c3)c(Cl)c2)cc1]

Step 1: Synthesis of 2-fluoro-1-isobutyl-4-nitrobenzene

1-Bromo-2-fluoro-4-nitrobenzene (1.1 g, 5 mmol), isobutylboronic acid (0.61 g, 6 mmol), caesium carbonate (4.1 g, 12.5 mmol), Pd(dppf)Cl$_2$ (370 mg, 0.5 mmol) and toluene/water (30 mL/3 mL) were added to a 50 mL single-neck flask, and the mixture was heated to react at 100° C. for 1 hour. After completion of the reaction, water (50 mL) was added, and the mixture was extracted with ethyl acetate (3*30 mL). The organic layers were concentrated in vacuo, and the residue was separated by a silica gel column (petroleum ether:ethyl acetate=20:1-10:1) to give a product (yellow oil, 1.05 g), with a yield of 99%. $^1$H NMR (400 MHz, CDCl$_3$) δ 7.96 (d, J=8.4 Hz, 1H), 7.88 (dd, J=9.4, 1.8 Hz, 1H), 7.33 (t, J=7.8 Hz, 1H), 2.61 (d, J=7.2 Hz, 2H), 1.94 (m, 1H), 0.95 (s, 3H), 0.93 (s, 3H).

Step 2: Synthesis of 3-fluoro-4-isobutylaniline

1-Isobutyl-2-fluoro-4-nitrobenzene (1.05 g, 5.3 mmol), Pd/C (5%) and methanol/H$_2$O (15 mL/5 mL) were added in a 50 mL single-neck flask, and the mixture was stirred overnight under hydrogen atmosphere. After completion of the reaction, the mixture was cooled and filtered to afford a product (yellow solid, 806 mg), with a yield of 66%. $^1$H NMR (400 MHz, CDCl$_3$) δ 6.91 (t, J=7.8 Hz, 1H), 6.39 (t, J=9.4 Hz, 2H), 3.59 (s, 2H), 2.41 (d, J=6.2 Hz, 2H), 1.96-1.70 (m, 1H), 0.92 (s, 3H), 0.91 (s, 3H).

Step 3: Synthesis of 4-bromo-2-fluoro-1-isobutylbenzene

To a solution of 3-fluoro-4-isobutylaniline (806 mg, 4.8 mmol) in acetonitrile/dimethylformamide (10 mL/5 mL) in a 50 mL single-neck flask was added a solution of tert-butyl nitrite (0.68 g, 5.8 mmol) in acetonitrile (2 mL) after cooled in an ice bath. The mixture was reacted in the ice bath for 20 minutes, then cuprous bromide (1.29 g, 5.8 mmol) was added, and the reaction was continued at room temperature overnight. After completion of the reaction, water (20 mL) was added, and the mixture was extracted with ethyl acetate (3*20 mL). The organic layers were concentrated in vacuo to remove the solvent to afford a crude product, which was used for the next step directly.

Step 4: Synthesis of 1-(4,4,5,5-tetramethyl-1,3,2-dioxaborolan-2-yl)-3-fluoro-4-isobutylbenzene 4-Bromo-2-fluoro-1-isobutylbenzene (806 mg, 3.49 mmol), bis(pinacolato)diboron (1.2 g, 4.76 mmol), potassium acetate (1.02 g, 10.5 mmol), PdCl$_2$(dppf) (255 mg, 0.35 mmol) and 1,4-dioxane (10 mL) were added in a microwave tube, and the mixture was reacted at 110° C. under microwave for 2 hours. After completion of the reaction, water (20 mL) was added, and the mixture was extracted with ethyl acetate (3*20 mL). The organic layers were concentrated in vacuo, combined, and separated by a silica gel column to give a product (yellow oil, 834.5 mg), with a yield of 86.0%.

Step 5: Synthesis of 2',6'-dichloro-3-fluoro-4-isobutyl-4'-nitro-1,1'-biphenyl 1-(4,4,5,5-Tetramethyl-1,3,2-dioxaborolan-2-yl)-3-fluoro-4-isobutylbenzene (834.5 mg, 3.0 mmol), 1,3-dichloro-2-iodo-5-nitrobenzene (1.14 g, 3.6 mmol), potassium carbonate (1.24 g, 9 mmol), PdCl$_2$(dtbpf) (98 mg, 0.15 mmol) and 2 wt % Tween 20 in water (5 mL) were added in a 20 mL single-neck flask, and the mixture was heated to react at 80° C. for 3 hours. After completion of the reaction, the mixture was extracted with ethyl acetate (3*10 mL), and the organic layers were combined and concentrated in vacuo to remove the solvent. The residue was separated by a silica gel column (petroleum ether:ethyl acetate=50:1-20:1) to give a product (orange solid, 822.3 mg), with a yield of 80.1%. $^1$H NMR (400 MHz, CDCl$_3$) δ 8.24 (s, 2H), 8.09 (s, 1H), 7.27-7.23 (m, 1H), 6.89 (d, J=7.6 Hz, 1H), 2.55 (d, J=7.1 Hz, 2H), 1.97-1.90 (m, 1H), 0.94 (s, 3H), 0.92 (s, 3H).

Step 6: Synthesis of 4'-amino-2',6'-dichloro-3-fluoro-4-isobutyl-1,1'-biphenyl

2',6'-Dichloro-3-fluoro-4-isobutyl-4'-nitro-1,1'-biphenyl (822.3 mg), methanol (5 mL) and platinum dioxide (82 mg) were added in a 25 mL single-neck flask, and the mixture was reacted at room temperature for 2 hours under hydrogen atmosphere. After completion of the reaction according to TLC, the mixture was filtered through Celite, and the filtrate was concentrated in vacuo to afford a crude product 608 mg, which was used in the next step directly.

Step 7: Synthesis of N-(2,6-dichloro-3'-fluoro-4'-isobutyl-[1,1'-biphenyl]-4-yl)-2-(4-(ethylsulfonyl)phenyl)acetamide The method is the same as in example 1. 4'-Amino-2',6'-dichloro-3-fluoro-4-isobutyl-1,1'-biphenyl (100 mg, 0.32 mmol), 2-(4-(ethylsulfonyl)phenyl)acetic acid (77 mg, 0.34 mmol), HATU (146 mg, 0.38 mmol), N,N-diisopropylethylamine (120 mg, 0.93 mmol) and dichloromethane (5 mL) were reacted at room temperature for 3 hours. The crude product was separated by a silica gel column (petroleum ether:ethyl acetate=2:1-1:1) to give a product (white solid, 70 mg), with a yield of 41.8%. $^1$H NMR (400 MHz, CDCl$_3$) δ 8.04 (s, 1H), 7.81 (d, J=8.1 Hz, 2H), 7.64 (s, 2H), 7.49 (d, J=8.0 Hz, 2H), 7.19 (t, J=8.0 Hz, 1H), 6.88 (t, J=8.4 Hz, 1H), 3.80 (s, 2H), 3.12 (t, J=7.4 Hz, 2H), 2.54 (d, J=7.2 Hz, 2H), 1.94 (dt, J=13.5, 6.8 Hz, 1H), 1.27 (d, J=7.4 Hz, 3H), 0.94 (d, J=6.6 Hz, 6H). MS (ESI) m/z: 522.0 (M+1).

Example 28

N-(2,6-dichloro-2'-cyano-4'-isobutyl-[1,1'-biphenyl]-4-yl)-2-(4-(ethylsulfonyl)phenyl)acetamide

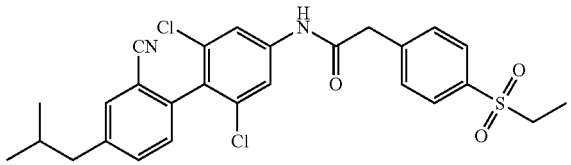 [SMILES: CCS(=O)(=O)c1ccc(CC(=O)Nc2cc(Cl)c(-c3ccc(CC(C)C)cc3C#N)c(Cl)c2)cc1]

Step 1: Synthesis of 5-isobutyl-2-nitrobenzonitrile

5-Bromo-2-nitrobenzonitrile (2.27 g, 10 mmol), isobutylboronic acid (1.53 g, 15 mmol), caesium carbonate (9.78 g, 30 mmol), Pd(dppf)Cl$_2$ (370 mg, 0.5 mmol) and toluene/water (100 mL/10 mL) were added in a 100 mL single-neck flask, and the mixture was heated to react at 110° C. for 1 hour. After completion of the reaction, water (50 mL) was added, and the mixture was extracted with ethyl acetate (3*30 mL). The organic layers were concentrated in vacuo and the residue was separated by a silica gel column (petroleum ether:ethyl acetate=20:1-10:1) to give a product (yellow oil, 1.5 g), with a yield of 75.0%. $^1$H NMR (400 MHz, CDCl$_3$) δ 8.22 (d, J=8.5 Hz, 1H), 7.64 (d, J=1.2 Hz, 1H), 7.61-7.52 (m, 1H), 2.61 (d, J=7.2 Hz, 2H), 1.97-1.85 (m, 1H), 0.90 (d, J=6.6 Hz, 6H).

Step 2: Synthesis of 2-amino-5-isobutylbenzonitrile

5-Isobutyl-2-nitrobenzonitrile (1.5 g, 7.35 mmol), ammonium formate (4.63 g, 73.5 mmol) and methanol/$H_2O$ (20 mL/2 mL) were added in a 25 mL single-neck flask, then zinc powder (2.38 g, 36.7 mmol) was added under stirring. The reaction mixture was heated to react at 80° C. for 1 hour. After completion of the reaction, the mixture was cooled to room temperature, and extracted with ethyl acetate (3*30 mL) to give a crude product (yellow solid, 1.3 g), with a yield of 100.0%. $^1$H NMR (400 MHz, $CDCl_3$) δ 7.13 (s, 1H), 7.10 (dd, J=8.4, 1.7 Hz, 1H), 6.66 (d, J=8.4 Hz, 1H), 4.27 (s, 2H), 2.33 (d, J=7.2 Hz, 2H), 1.83-1.66 (m, 1H), 0.86 (d, J=6.6 Hz, 6H). MS (ESI) m/z: 176.1 (M+1).

Step 3: Synthesis of 2-bromo-5-isobutylbenzonitrile

To a solution of 2-amino-5-isobutylbenzonitrile (1.3 g, 7.4 mmol) in acetonitrile/dimethylformamide (10 mL/5 mL) in a 50 mL single-neck flask was added a solution of tert-butyl nitrite (1.04 g, 8.88 mmol) in acetonitrile (2 mL) after cooled in an ice bath. The mixture was reacted in the ice bath for 20 minutes, then cuprous bromide (1.98 g, 8.88 mmol) was added, and the reaction was continued at room temperature overnight. After completion of the reaction, water (20 mL) was added, and the mixture was extracted with ethyl acetate (3*20 mL) and concentrated in vacuo to remove the solvent. The crude product was separated by a silica gel column (petroleum ether:ethyl acetate=10:1-5:1) to give a product (yellow solid, 500 mg), with a yield of 82.4%. $^1$H NMR (400 MHz, $CDCl_3$) δ 7.56 (d, J=8.3 Hz, 1H), 7.42 (d, J=1.8 Hz, 1H), 7.22 (dd, J=8.3, 2.1 Hz, 1H), 2.45 (d, J=7.2 Hz, 2H), 1.91-1.77 (m, 1H), 0.89 (d, J=6.6 Hz, 6H).

Step 4: Synthesis of 5-isobutyl-2-(4,4,5,5-tetramethyl-1,3,2-dioxaborolan-2-yl)benzonitrile 2-Bromo-5-isobutylbenzonitrile (450 mg, 1.89 mmol), bis(pinacolato)diboron (855 mg, 3.78 mmol), potassium acetate (556 mg, 5.67 mmol), $PdCl_2$(dppf) (70 mg, 0.095 mmol) and 1,4-dioxane (10 mL) were added in a microwave tube, and the mixture was reacted at 110° C. under microwave for 2 hours. After completion of the reaction, water (20 mL) was added, and the mixture was extracted with ethyl acetate (3*20 mL). The combined organic layers were concentrated in vacuo to remove the solvent, and the residue was separated by a silica gel column to give a product (yellow oil, 420 mg), with a yield of 83.6%. $^1$H NMR (400 MHz, $CDCl_3$) δ 7.77 (d, J=7.7 Hz, 1H), 7.46 (s, 1H), 7.33 (dd, J=7.7, 1.3 Hz, 1H), 2.49 (d, J=7.2 Hz, 2H), 1.36 (s, 12H), 1.26-1.23 (m, 1H), 0.87 (d, J=6.6 Hz, 6H).

Step 5: Synthesis of 2',6'-dichloro-4-isobutyl-4'-nitro-[1,1'-biphenyl]-2-carbonitrile 5-Isobutyl-2-(4,4,5,5-tetramethyl-1,3,2-dioxaborolan-2-yl)benzonitrile (100 mg, 0.35 mmol), 1,3-dichloro-2-iodo-5-nitrobenzene (133 mg, 1.2 mmol), potassium carbonate (143 mg, 1.05 mmol), $PdCl_2$(dtbpf) (11 mg, 0.02 mmol) and 2 wt % Tween 20 in water (3 mL) were added in a 20 mL single-neck flask, and the mixture was heated to react at 80° C. for 3 hours. After completion of the reaction, the mixture was extracted with ethyl acetate (3*10 mL), and the organic layers were combined and concentrated in vacuo to remove the solvent. The residue was separated by a silica gel column (petroleum ether:ethyl acetate=50:1-20:1) to give a product (orange solid, 110 mg), with a yield of 90.1%. $^1$H NMR (400 MHz, $CDCl_3$) δ 8.32 (s, 2H), 7.60 (s, 1H), 7.52 (d, J=7.9 Hz, 1H), 7.24 (d, J=9.0 Hz, 1H), 2.59 (d, J=7.2 Hz, 2H), 2.00-1.88 (m, 1H), 0.95 (d, J=6.6 Hz, 6H).

Step 6: Synthesis of 4'-amino-2',6'-dichloro-4-isobutyl-[1,1'-biphenyl]-2-carbonitrile 2',6'-Dichloro-4-isobutyl-4'-nitro-[1,1'-biphenyl]-2-carbonitrile (110 mg), methanol (2 mL) and platinum dioxide (11 mg) were added in a 25 mL single-neck flask with a hydrogen balloon equipped. The mixture was reacted at room temperature for 2 hours. After completion of the reaction according to TLC, the mixture was filtered through Celite, and the filtrate was concentrated in vacuo to afford a crude product (100 mg), which was used in the next step directly. MS (ESI) m/z: 319.0 (M+1).

Step 7: Synthesis of N-(2,6-dichloro-2'-cyano-4'-isobutyl-[1,1'-biphenyl]-4-yl)-2-(4-(ethylsulfonyl)phenyl)acetamide The method is the same as in example 1. 4'-Amino-2',6'-dichloro-4-isobutyl-[1,1'-biphenyl]-2-carbonitrile (100 mg, 0.31 mmol), 2-(4-(ethylsulfonyl)phenyl)acetic acid (93 mg, 0.41 mmol), HATU (156 mg, 0.41 mmol), N,N-diisopropylethylamine (120 mg, 0.93 mmol) and dichloromethane (5 mL) were reacted at room temperature for 3 hours. The crude product was separated by a silica gel column (petroleum ether:ethyl acetate=2:1-1:1) to give a product (white solid, 73 mg), with a yield of 44.8%. $^1$H NMR (400 MHz, DMSO-$d_6$) δ 10.72 (s, 1H), 7.83 (d, J=6.6 Hz, 4H), 7.77 (s, 1H), 7.59 (d, J=8.1 Hz, 3H), 7.36 (d, J=7.9 Hz, 1H), 3.84 (s, 2H), 3.25 (q, J=7.4 Hz, 2H), 2.54 (d, J=7.2 Hz, 2H), 1.96-1.83 (m, 1H), 1.07 (t, J=7.3 Hz, 3H), 0.85 (d, J=6.6 Hz, 6H). MS (ESI) m/z: 526.9 (M−1).

Example 29

N-(2-chloro-4'-isobutyl-2'-(trifluoromethyl)-[1,1'-biphenyl]-4-yl)-2-(4-(ethylsulfonyl)phenyl)acetamide

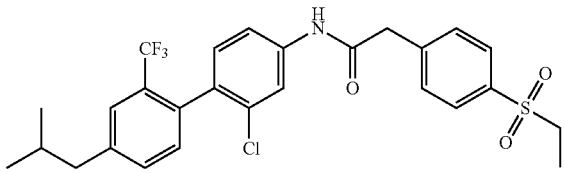 [SMILES: CCS(=O)(=O)c1ccc(CC(=O)Nc2ccc(-c3ccc(CC(C)C)cc3C(F)(F)F)c(Cl)c2)cc1]

Step 1: Synthesis of 4-isobutyl-2-(trifluoromethyl)aniline

To a mixture of 4-bromo-2-(trifluoromethyl)aniline (960 mg, 4 mmol), isobutylboronic acid (612 mg, 6 mmol), caesium carbonate (612 mg, 6 mmol) and toluene/water (10:1, 10 mL) in a microwave tube was added Pd(dppf)$Cl_2$ (146 mg, 5% eq) under argon atmosphere. The reaction mixture was heated to react at 120° C. for 1 hour under microwave. After completion of the reaction, the mixture was filtered through Celite and washed with dichloromethane. The filtrate was concentrated in vacuo to remove the solvent, and the residue was purified by a silica gel column to give a product 4-isobutyl-2-(trifluoromethyl)aniline (583.9 mg), with a yield of 67.2%. MS (ESI) m/z: 218 (M+1).

Step 2: Synthesis of 1-bromo-4-isobutyl-2-(trifluoromethyl)benzene

To a solution of 4-isobutyl-2-(trifluoromethyl)aniline (545 mg, 2.5 mmol) in acetonitrile (10 mL) in an ice bath was added cuprous bromide (640 mg, 2.85 mmol) slowly, and the mixture was kept in the ice bath for 20 minutes. Then a solution of tert-butyl nitrite (375 mg, 3.65 mmol) in acetonitrile (10 mL) was added under nitrogen atmosphere, and the mixture was stirred at room temperature for 5 hours. After completion of the reaction, the reaction mixture was poured into saturated sodium bicarbonate solution (40 mL) and extracted with ethyl acetate (3*20 mL). The combined organic layers were concentrated in vacuo and purified by a silica gel column to afford 1-bromo-4-isobutyl-2-(trifluoromethyl)benzene (450 mg), with a yield of 63.8%. $^1$H NMR (400 MHz, CD$_3$OD) δ 7.68 (d, 1H), 7.53 (s, 1H), 7.30 (d, 1H), 2.54-2.52 (d, 2H), 1.89-1.85 (m, 1H), 0.91-0.90 (d, 6H). MS (ESI) m/z: 282 (M+1).

Step 3: Synthesis of 3-chloro-4-(4,4,5,5-tetramethyl-1,3,2-dioxaborolan-2-yl)aniline To a mixture of 4-bromo-3-chloroaniline (413 mg, 2 mmol), bis(pinacolato)diboron (762 mg, 3 mmol), potassium acetate (762 mg, 3 mmol) and 1,4-dioxane (10 mL) in a microwave tube was added Pd(dppf) Cl$_2$ (80 mg, 5% eq) under argon atmosphere. The mixture was heated to react at 100° C. under microwave for 1 hour. After completion of the reaction, the mixture was filtered through Celite and washed with dichloromethane. The organic layer was concentrated in vacuo, and the residue was purified by a silica gel column to give 3-chloro-4-(4,4,5,5-tetramethyl-1,3,2-dioxaborolan-2-yl)aniline (230 mg), with a yield of 46%. MS (ESI) m/z: 254 (M+1).

Step 4: Synthesis of 2-chloro-4'-isobutyl-2'-(trifluoromethyl)-[1,1'-biphenyl]-4-amine To a mixture of 3-chloro-4-(4,4,5,5-tetramethyl-1,3,2-dioxaborolan-2-yl)aniline (127 mg, 0.5 mmol), 1-bromo-4-isobutyl-2-(trifluoromethyl)benzene (223 mg, 0.75 mmol), sodium carbonate (106 mg, 1 mmol) and anhydrous 1,4-dioxane/water (10:1, 8 mL) in a microwave tube was added Pd(PPh$_3$)$_4$ (5.8 mg, 1% eq) under argon atmosphere. The mixture was heated to react at 100° C. for 1 hour under microwave. After completion of the reaction, the mixture was filtered through Celite and washed with dichloromethane. The organic layer was concentrated in vacuo, and the residue was purified by a silica gel column to give 2-chloro-4'-isobutyl-2'-(trifluoromethyl)-[1,1'-biphenyl]-4-amine (80 mg), with a yield of 48%. MS (ESI) m/z: 328 (M+1).

Step 5: Synthesis of N-(2-chloro-4'-isobutyl-2'-(trifluoromethyl)-[1,1'-biphenyl]-4-yl)-2-(4-(ethyl sulfonyl)phenyl)acetamide 2-(4-(Ethylsulfonyl)phenyl)acetic acid (61.3 mg, 0.27 mmol), HATU (140 mg, 0.37 mmol), DIPEA (47.3 mg, 0.37 mmol) and DCM (5 mL) were added in an pear flask, and the mixture was stirred for 10 minutes. Then 2-chloro-4'-isobutyl-2'-(trifluoromethyl)-[1,1'-biphenyl]-4-aniline (80 mg, 0.24 mmol) was added. The mixture was stirred at room temperature for 8 hours. After completion of the reaction, the reaction mixture was diluted with ethyl acetate (25 mL), and washed with water and then with saturated brine. The organic layer was concentrated in vacuo, and the residue was purified by a silica gel column to give N-(2-chloro-4'-isobutyl-2'-(trifluoromethyl)-[1,1'-biphenyl]-4-yl)-2-(4-(ethylsulfonyl)phenyl)acetamide (90 mg), with a yield of 68.6%. $^1$H NMR (400 MHz, CDCl$_3$) δ 7.80-7.78 (d, 2H), 7.65 (s, 1H), 7.46-7.41 (m, 3H), 7.31-7.23 (m, 2H), 7.21-7.19 (d, 1H), 7.15-7.13 (m, 2H), 3.82 (s, 2H), 3.16-3.10 (q, 2H), 2.58-2.56 (d, 2H), 1.96-1.89 (m, 1H), 1.31-1.26 (t, 3H), 0.95-0.94 (d, 6H). MS (ESI) m/z: 536.2 (M−1).

Example 30

N-(2-Chloro-4'-isobutyl-2'-(trifluoromethoxy)-[1,1'-biphenyl]-4-yl)-2-(4-(ethylsulfonyl)phenyl)acetamide

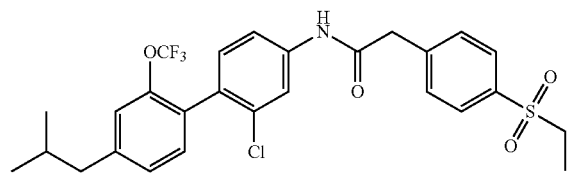 [SMILES: CCS(=O)(=O)c1ccc(CC(=O)Nc2ccc(-c3ccc(CC(C)C)cc3OC(F)(F)F)c(Cl)c2)cc1]

Step 1: Synthesis of 4-isobutyl-2-(trifluoromethoxy)aniline

To a mixture of 4-bromo-2-(trifluoromethoxy)aniline (1024 mg, 4 mmol), isobutylboronic acid (612 mg, 6 mmol), caesium carbonate (612 mg, 6 mmol) and toluene/water (10:1, 10 mL) in a microwave tube was added Pd(dppf)Cl$_2$ (146 mg, 5% eq) under argon atmosphere. The reaction mixture was reacted at 120° C. for 1 hour under microwave. After completion of the reaction, the mixture was filtered through Celite and washed with dichloromethane. The organic layer was concentrated in vacuo, and the residue was purified by a silica gel column to give 4-isobutyl-2-(trifluoromethoxy)aniline (662.8 mg), with a yield of 67.2%. MS (ESI) m/z: 255.9 (M+1).

Step 2: Synthesis of 1-bromo-4-isobutyl-2-(trifluoromethoxy)benzene

To a solution of 4-isobutyl-2-(trifluoromethoxy)aniline (585 mg, 2.5 mmol) in acetonitrile (10 mL) in an ice bath was added cuprous bromide (640 mg, 2.85 mmol) slowly, and the mixture was kept in an ice bath for 20 minutes. Then a solution of tert-butyl nitrite (375 mg, 3.65 mmol) in acetonitrile (10 mL) was added under nitrogen atmosphere, and the mixture was stirred at room temperature for 5 hours. After completion of the reaction, the reaction mixture was poured into saturated sodium bicarbonate solution (40 mL) and extracted with ethyl acetate (3*20 mL). The combined organic layers were concentrated in vacuo, and the residue was purified by a silica gel column to give 1-bromo-4-isobutyl-2-(trifluoromethoxy)benzene (475.6 mg), with a yield of 63.8%. MS (ESI) m/z: 297 (M+1).

Step 3: Synthesis of 3-chloro-4-(4,4,5,5-tetramethyl-1,3,2-dioxaborolan-2-yl)aniline To a mixture of 4-bromo-3-chloroaniline (413 mg, 2 mmol), bis(pinacolato)diboron (762 mg, 3 mmol), potassium acetate (762 mg, 3 mmol) and anhydrous 1,4-dioxane (10 mL) in a microwave tube was added Pd(dppf) Cl$_2$ (80 mg, 5% eq) under argon atmosphere. The mixture was heated to react at 100° C. under microwave for 1 hour. After completion of the reaction, the mixture was filtered through Celite and washed with dichloromethane. The organic layer was concentrated in vacuo, and the residue was purified by a silica gel column to give 3-chloro-4-(4,4,5,5-tetramethyl-1,3,2-dioxaborolan-2-yl)aniline (230 mg), with a yield of 46%. MS (ESI) m/z: 254 (M+1).

Step 4: Synthesis of 2-chloro-4'-isobutyl-2'-(trifluoromethoxy)-[1,1'-biphenyl]-4-amine To a mixture of 3-chloro-4-(4,4,5,5-tetramethyl-1,3,2-dioxaborolan-2-yl)aniline (127 mg, 0.5 mmol), 1-bromo-4-isobutyl-2-(trifluoromethyl)benzene (235.7 mg, 0.75 mmol), sodium carbonate (106 mg, 1 mmol) and anhydrous 1,4-dioxane/water (10:1, 8 mL) in a microwave tube was added Pd(PPh$_3$)$_4$ (5.8 mg, 1% eq) under argon atmosphere. The mixture was heated to react at 100° C. for 1 hour under microwave. After completion of the reaction, the mixture was filtered through Celite and washed with dichloromethane. The organic layer was concentrated in vacuo, and the residue was purified by a silica gel column to give 2-chloro-4'-isobutyl-2'-(trifluoromethyl)-[1,1'-biphenyl]-4-amine (80 mg), with a yield of 48%. MS (ESI) m/z: 328 (M+1).

Step 5: Synthesis of N-(2-Chloro-4'-isobutyl-2'-(trifluoromethoxy)-[1,1'-biphenyl]-4-yl)-2-(4-(ethylsulfonyl)phenyl)acetamide 2-(4-(Ethylsulfonyl)phenyl)acetic acid (61.3 mg, 0.27 mmol), HATU (140 mg, 0.37 mmol), DIPEA (47.3 mg, 0.37 mmol) and DCM (5 mL) were added in an pear-shaped flask, and the mixture was stirred for 10 minutes. Then 2-chloro-4'-isobutyl-2'-(trifluoromethoxy)-[1,1'-biphenyl]-4-aniline (84 mg, 0.24 mmol) was added, and the mixture was stirred at room temperature for 8 hours. After completion of the reaction, the reaction mixture was diluted with ethyl acetate (25 mL), and washed with water and then with saturated brine. The organic layer was concentrated in vacuo, and the residue was purified by a silica gel column to give N-(2-chloro-4'-isobutyl-2'-(trifluoromethoxy)-[1,1'-biphenyl]-4-yl)-2-(4-(ethylsulfonyl)phenyl)acetamide (93 mg), with a yield of 68.7%. $^1$H NMR (400 MHz, CDCl$_3$) δ 7.91-7.89 (d, 2H), 7.73 (s, 1H), 7.56-7.54 (d, 2H), 7.42-7.41 (d, 2H), 7.21-7.18 (m, 1H), 7.12-7.11 (d, 2H), 3.83 (s, 2H), 3.16-3.10 (q, 2H), 2.54-2.52 (d, 2H), 1.92-1.89 (m, 1H), 1.32-1.28 (t, 3H), 0.95-0.93 (d, 6H). MS (ESI) m/z: 552.1 (M+1).

Example 31

N-(2-Chloro-3'-cyano-4'-isobutyl-[1,1'-biphenyl]-4-yl)-2-(4-(ethylsulfonyl)phenyl)acetamide

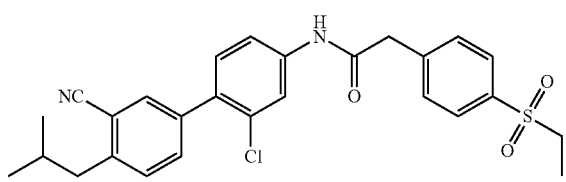 [SMILES: CCS(=O)(=O)c1ccc(CC(=O)Nc2ccc(-c3ccc(CC(C)C)c(C#N)c3)c(Cl)c2)cc1]

Synthesis of intermediate 31a: 3-chloro-4-(4,4,5,5-tetramethyl-1,3,2-dioxaborolan-2-yl)aniline To a mixture of 4-bromo-3-chloroaniline (1 g, 9.7 mmol), bis(pinacolato)diboron (1.85 g, 14.56 mmol), potassium acetate (2.8 g, 29 mmol) and 1,4-dioxane (10 mL) in a 20 mL microwave tube was added Pd(dppf)Cl$_2$ (196 mg, 0.27 mmol) under nitrogen atmosphere, and the mixture was reacted at 100° C. under microwave for 1 hour. After completion of the reaction, solvent was removed in vacuo, then saturated sodium chloride (20 mL) was added. The mixture was washed with ethyl acetate (8 mL) and dried over anhydrous sodium sulfate. The organic layers were combined and concentrated in vacuo, and the crude product was separated by a silica gel column (petroleum ether:ethyl acetate=5:1) to give a product (white solid, 1 g), with a yield of 54.3%. MS (ESI) m/z: 254.1 (M+1).

Synthesis of Intermediate 31b: 5-bromo-2-isobutylbenzonitrile

Step 1: Synthesis of 2-isobutyl-5-nitrobenzonitrile

To a mixture of 5-amino-2-bromobenzonitrile (1 g, 5.1 mmol), isobutylboronic acid (1.2 g, 11.8 mmol), caesium carbonate (2 g, 6.1 mmol), toluene (10 mL) and water (0.3 mL) in a 20 mL microwave tube was added Pd(dppf)Cl$_2$ (350 mg, 0.48 mmol) under nitrogen atmosphere, and the mixture was heated to react at 120° C. under microwave for 2 hours. After completion of the reaction, solvent was removed in vacuo, then saturated sodium chloride (20 mL) was added. The mixture was extracted with ethyl acetate (8 mL), dried over anhydrous sodium sulfate. The organic layers were combined and concentrated in vacuo, and the crude product was separated by a silica gel column (petroleum ether:ethyl acetate=10:1) to give a product (white solid, 0.5 g), with a yield of 56.3%. MS (ESI) m/z: 175.1 (M+1).

Step 2: Synthesis of 5-bromo-2-isobutylbenzonitrile

To a mixture of 2-isobutyl-5-nitrobenzonitrile (500 mg, 2.9 mmol), cuprous bromide (86 mg, 0.6 mmol), cupric bromide (1.3 g, 5.8 mmol), hydrobromic acid (364 μL, 6.7 mmol) and acetonitrile (20 mL) in a 100 mL single-neck flask cooled in an ice bath was added a solution of sodium nitrite (242 mg, 3.0 mmol) in acetonitrile slowly. After stirred in the ice bath for half an hour, the mixture was slowly warmed to room temperature and stirred overnight. After the materials had all reacted when being determined by TLC, solvent was removed in vacuo, and saturated sodium chloride (20 mL) was added. The mixture was extracted with ethyl acetate (8 mL) and dried over anhydrous sodium sulfate. The organic layers were combined and concentrated in vacuo, and the cruded product was separated by a silica gel column (eluent: 100% of petroleum ether) to give a product (white solid, 260 mg), with a yield of 37.8%. $^1$H NMR (400 MHz, CDCl$_3$) δ 7.72 (s, 1H), 7.61 (d, J=8.4 Hz, 1H), 7.16 (d, J=8.4 Hz, 1H), 2.66 (d, J=7.3 Hz, 2H), 2.01-1.88 (m, 1H), 0.94 (d, J=6.6 Hz, 6H).

Synthesis of N-(2-chloro-3'-cyano-4'-isobutyl-[1,1'-biphenyl]-4-yl)-2-(4-(ethylsulfonyl)phenyl)acetamide Step 1: Synthesis of 4'-amino-2'-chloro-4-isobutyl-[1,1'-biphenyl]-3-carbonitrile To a mixture of 5-bromo-2-isobutylbenzonitrile (180 mg, 0.76 mmol), 3-chloro-4-(4,4,5,5-tetramethyl-1,3,2-dioxaborolan-2-yl)aniline (280 mg, 1.11 mmol) and sodium carbonate (110 mg, 1.0 mmol) in a 20 mL microwave reaction tube were added Pd(dppf)Cl$_2$ (30 mg, 0.04 mmol), 1,4-dioxane (5 mL) and water (1.25 mL) under argon atmosphere. The mixture was heated to react at 100° C. under microwave for 2 hours. Then solvent was removed in vacuo, and saturated sodium chloride (20 mL) was added. The mixture was extracted with ethyl acetate (8 mL), and dried over anhydrous sodium sulfate. The organic layers were combined and concentrated in vacuo, and the crude product was separated by a silica gel column (petroleum ether:ethyl acetate=10:1) to give a product (white solid, 80 mg), with a yield of 37.0%. MS (ESI) m/z: 285.1 (M+1).

Step 2: Synthesis of N-(2-chloro-3'-cyano-4'-isobutyl-[1,1'-biphenyl]-4-yl)-2-(4-(ethylsulfonyl)phenyl)acetamide 4'-Amino-2'-chloro-4-isobutyl-[1,1'-biphenyl]-3-carbonitrile (80 mg, 0.28 mmol), 2-(4-(ethylsulfonyl)phenyl)acetic acid (75 mg, 0.28 mmol), HATU (114 mg, 0.30 mmol), N,N-diisopropylethylamine (96 μL, 0.6 mmol) and dichloromethane (20 mL) were added in a 25 mL single-neck flask, and the reaction mixture was stirred at room temperature overnight. The crude product was separated by a silica gel column (petroleum ether:ethyl acetate=1:2) to give a product (white solid, 70 mg), with a yield of 50.6%. $^1$H NMR (400 MHz, CDCl$_3$) δ 8.19 (s, 1H), 7.84 (d, J=8.1 Hz, 2H), 7.76 (s, 1H), 7.63 (s, 1H), 7.57-7.47 (m, 4H), 7.31 (d, J=8.1 Hz, 1H), 7.23 (d, J=8.4 Hz, 1H), 3.81 (s, 2H), 3.11 (q, J=7.4 Hz, 2H), 2.74 (d, J=7.2 Hz, 2H), 2.02-1.96 (m, 1H), 1.28 (t, J=7.4 Hz, 3H), 0.97 (d, J=6.6 Hz, 6H). MS (ESI) m/z: 493.1 (M−1).

Example 32

N-(2,6-Dichloro-3'-cyano-4'-isopropoxy-[1,1'-biphenyl]-4-yl)-2-(4-(ethylsulfonyl)phenyl)acetamide

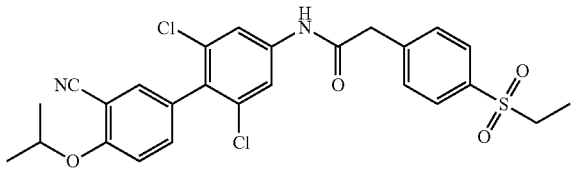 [SMILES: CCS(=O)(=O)c1ccc(CC(=O)Nc2cc(Cl)c(-c3ccc(OC(C)C)c(C#N)c3)c(Cl)c2)cc1]

Step 1: Synthesis of 2-isopropoxy-5-(4,4,5,5-tetramethyl-1,3,2-dioxaborolan-2-yl)benzonitrile 5-Bromo-2-isopropoxybenzonitrile (1 g, 4.17 mmol), bis(pinacolato)diboron (1.41 g, 6.25 mmol), potassium acetate (1.22 g, 12.5 mmol), PdCl$_2$(dppf) (153 mg, 0.21 mmol) and 1,4-dioxane (10 mL) were added in a microwave tube, and the mixture was reacted at 110° C. under microwave for 2 hours. After completion of the reaction, water (20 mL) was added, and the mixture was extracted with ethyl acetate (3*20 mL). The organic layers were combined and concentrated in vacuo, and the residue was separated by a silica gel column (petroleum ether:ethyl acetate=5:1-1:1) to give a product (yellow oil, 400 mg), with a yield of 33.3%.

Step 2: Synthesis of 2',6'-dichloro-4-isopropoxy-4'-nitro-[1,1'-biphenyl]-3-carbonitrile 2-Isopropoxy-5-(4,4,5,5-tetramethyl-1,3,2-dioxaborolan-2-yl)benzonitrile (400 mg, 1.39 mmol), 1,3-dichloro-2-iodo-5-nitrobenzene (531 mg, 1.67 mmol), potassium carbonate (567 mg, 4.17 mmol), PdCl$_2$(dtbpf) (45 mg, 0.07 mmol) and 2 wt % Tween 20 in water (10 mL) were added in a 20 mL single-neck flask. The mixture was heated to react at 80° C. for 2 hours, After completion of the reaction, the mixture was extracted with ethyl acetate (3*10 mL), and the combined organic layers were concentrated in vacuo to remove the solvent. The residue was separated by a silica gel column (petroleum ether:ethyl acetate=10:1-5:1) to give a product (orange solid, 120 mg), with a yield of 24.6%. $^1$H NMR (400 MHz, CDCl$_3$) δ 8.28 (s, 2H), 7.46 (d, J=2.0 Hz, 1H), 7.39 (dd, J=8.8, 2.2 Hz, 1H), 7.07 (d, J=8.8 Hz, 1H), 4.78-4.67 (m, 1H), 1.46 (d, J=6.1 Hz, 6H), 1.25 (t, J=7.2 Hz, 4H).

Step 3: Synthesis of 4'-amino-2',6'-dichloro-4-isopropoxy-[1,1'-biphenyl]-3-carbonitrile 2',6'-Dichloro-4-isopropoxy-4'-nitro-[1,1'-biphenyl]-3-carbonitrile (120 mg), methanol (2 mL) and platinum dioxide (12 mg) were added in a 25 mL single-neck flask with a hydrogen balloon equipped. The mixture was reacted at room temperature for 1 hour. After completion of the reaction according to TLC, the mixture was filtered through Celite, and the filtrate was concentrated in vacuo to afford a crude product (100 mg), which was used in the next step directly. MS (ESI) m/z: 321.0 (M+1).

Step 4: Synthesis of N-(2,6-dichloro-3'-cyano-4'-isopropoxy-[1,1'-biphenyl]-4-yl)-2-(4-(ethylsulfonyl)phenyl)acetamide The method is the same as in example 1. 4'-Amino-2',6'-dichloro-4-isopropoxy-[1,1'-biphenyl]-3-carbonitrile (100 mg, 0.31 mmol), 2-(4-(ethylsulfonyl)phenyl)acetic acid (93 mg, 0.41 mmol), HATU (156 mg, 0.41 mmol), N,N-diisopropylethylamine (120 mg, 0.93 mmol) and dichloromethane (5 mL) were reacted at room temperature for 3 hours, and the crude product was separated by a silica gel column (petroleum ether:ethyl acetate=2:1-1:1) to give a product (white solid, 90 mg), with a yield of 54.9%. $^1$H NMR (400 MHz, CDCl$_3$) δ 8.75 (s, 1H), 7.82 (d, J=8.1 Hz, 2H), 7.71 (s, 2H), 7.54 (d, J=8.1 Hz, 2H), 7.43 (d, J=2.0 Hz, 1H), 7.37 (dd, J=8.8, 2.1 Hz, 1H), 7.04 (d, J=8.9 Hz, 1H), 4.71 (dt, J=12.1, 6.1 Hz, 1H), 3.82 (s, 2H), 3.14 (q, J=7.4 Hz, 2H), 1.44 (d, J=6.0 Hz, 6H), 1.29 (t, J=7.4 Hz, 3H). MS (ESI) m/z: 528.8 (M+1).

Example 33

N-(2,6-Dichloro-3'-cyano-4'-((diethylamino)methyl)-[1,1'-biphenyl]-4-yl)-2-(4-(methylsulfonyl)phenyl)acetamide

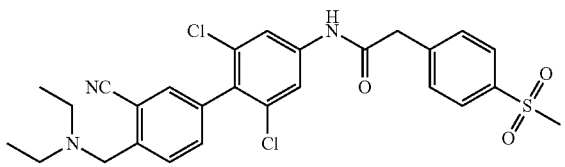 [SMILES: CCN(CC)Cc1ccc(-c2c(Cl)cc(NC(=O)Cc3ccc(S(C)(=O)=O)cc3)cc2Cl)cc1C#N]

Step 1: Synthesis of 2-methyl-5-(4,4,5,5-tetramethyl-1,3,2-dioxaborolan-2-yl)benzonitrile 5-Bromo-2-methylbenzonitrile (40 g, 204 mmol), bis(pinacolato)diboron (69.2 g, 306 mmol), potassium acetate (60 g, 612 mmol), PdCl$_2$(dppf) (7.6 g, 20.8 mmol) and 1,4-dioxane (500 mL) were added in a 1 L single-neck flask, and the reaction mixture was heated to react at 100° C. for 2 hours. After completion of the reaction, the mixture was cooled to room temperature, then water (250 mL) was added. The mixture was extracted with ethyl acetate (3*250 mL), and the organic layers were concentrated in vacuo to remove the solvent. The residue was separated by a silica gel column (petroleum ether:ethyl acetate=30:1) to give a product (white solid, 30 g), with a yield of 61.2%. $^1$H NMR (400 MHz, CDCl$_3$) δ 8.03 (s, 1H), 7.87 (d, J=7.7 Hz, 1H), 7.31 (d, J=7.7 Hz, 1H), 2.55 (s, 4H), 1.34 (s, 12H).

Step 2: Synthesis of 2',6'-dichloro-4-methyl-4'-nitro-[1,1'-biphenyl]-3-carbonitrile 2-Methyl-5-(4,4,5,5-tetramethyl-1,3,2-dioxaborolan-2-yl)benzonitrile (20 g, 82.4 mmol), 1,3-dichloro-2-iodo-5-nitrobenzene (28.5 g, 90.6 mmol), potassium carbonate (26.3 g, 247.2 mmol), PdCl$_2$(dtbpf) (1.34 g, 2.06 mmol) and 2 wt % Tween 20 in water (200 mL) were added in a 500 mL single-neck flask, and the reaction mixture was heated to react at 80° C. for 6 hours. After completion of the reaction, the mixture was extracted with ethyl acetate (3*100 mL), and the organic layers were combined and concentrated to remove the solvent. The residue was separated by a silica gel column (petroleum ether:ethyl acetate=10:1) to give a product (orange solid, 25 g), with a yield of 79.1%.

Step 3: Synthesis of 4-(bromomethyl)-2',6'-dichloro-4'-nitro-[1,1'-biphenyl]-3-carbonitrile 2',6'-Dichloro-4-methyl-4'-nitro-[1,1'-biphenyl]-3-carbonitrile (5.07 g, 16.5 mmol), NBS (3.42 g, 19.2 mmol), BPO (198 mg, 0.83 mmol) and carbon tetrachloride (70 mL) were added in a 100 mL single-flask mouth, and the mixture was heated to react at 90° C. overnight. After completion of the reaction, solvent was removed in vacuo, and the residue was separated by a silica gel column (petroleum ether:ethyl acetate=50:1-20:1) to give a product (3.1 g), with a yield of 49.6%. $^1$H NMR (400 MHz, CDCl$_3$) δ 8.31 (s, 2H), 7.72 (d, J=8.1 Hz, 1H), 7.58 (d, J=1.6 Hz, 1H), 7.49 (dd, J=8.1, 1.8 Hz, 1H), 4.71 (s, 2H).

Step 4: Synthesis of 2',6'-dichloro-4-((diethylamino)methyl)-4'-nitro-[1,1'-biphenyl]-3-carbonitrile 4-(Bromomethyl)-2',6'-dichloro-4'-nitro-[1,1'-biphenyl]-3-carbonitrile (150 mg, 0.39 mmol), diethylamine hydrochloride (85 mg, 0.78 mmol), potassium carbonate (265 mg, 1.95 mmol) and acetonitrile (5 mL) were added in a 25 mL single-neck flask, and the mixture was heated to react at 80° C. for 2 hours. After completion of the reaction, water was added (20 mL), and the mixture was extracted with ethyl acetate (3*10 mL). The organic layers were combined, washed with saturated sodium chloride, dried over anhydrous sodium sulfate, and concentrated in vacuo to remove the solvent to obtain a crude product (yellow solid, 170 mg), which was used for the next step directly.

$^1$H NMR (400 MHz, CDCl$_3$) δ 8.30 (s, 2H), 7.82 (d, J=7.3 Hz, 1H), 7.52 (s, 1H), 7.44 (d, J=8.1 Hz, 1H), 3.85 (s, 2H), 2.63 (q, J=6.8 Hz, 4H), 1.09 (t, J=7.0 Hz, 6H).

Step 5: Synthesis of 4'-amino-2',6'-dichloro-4-((diethylamino)methyl)-[1,1'-biphenyl]-3-carbonitrile 2',6'-Dichloro-4-((diethylamino)methyl)-4'-nitro-[1,1'-biphenyl]-3-carbonitrile (150 mg, 0.4 mmol), ammonium formate (252 mg, 4 mmol) and methanol/H$_2$O (5 mL/5 mL) were added in a 25 mL single-neck flask, then zinc powder (130 mg, 2 mmol) was added under stirring. The mixture was heated to react at 80° C. for 2 hours. After completion of the reaction, the mixture was cooled to room temperature and extracted with ethyl acetate (3*10 mL) to afford a product (yellow solid, 120 mg), which was used for the next step directly.

Step 6: N-(2,6-Dichloro-3'-cyano-4'-((diethylamino)methyl)-[1,1'-biphenyl]-4-yl)-2-(4-(methylsulfonyl)phenyl)acetamide The method is the same as in example 1. 4'-Amino-2',6'-dichloro-4-((diethylamino)methyl)-[1,1'-biphenyl]-3-carbonitrile (100 mg, 0.29 mmol), 2-(4-(methylsulfonyl)phenyl)acetic acid (74 mg, 0.34 mmol), HATU (129 mg, 0.34 mmol), N,N-diisopropylethylamine (112 mg, 0.87 mmol) and dichloromethane (3 mL) were reacted at room temperature for 2 hours, and the crude product was separated by a silica gel column (petroleum ether:ethyl acetate=1:1-1:2) to give a product (white solid, 157 mg), with a yield of 99.0%. $^1$H NMR (400 MHz, CDCl$_3$) δ 8.84 (d, J=8.9 Hz, 1H), 7.89 (d, J=8.2 Hz, 2H), 7.76-7.70 (m, 3H), 7.55 (d, J=8.2 Hz, 2H), 7.49 (s, 1H), 7.42 (dd, J=8.1, 1.5 Hz, 1H), 3.83 (s, 4H), 3.07 (s, 3H), 2.63 (q, J=7.1 Hz, 4H), 1.09 (t, J=7.1 Hz, 6H). MS (ESI) m/z: 543.8 (M+1).

Example 34

N-(2,6-Dichloro-3'-cyano-4'-((dimethylamino)methyl)-[1,1'-biphenyl]-4-yl)-2-(4-(methylsulfonyl)phenyl)acetamide

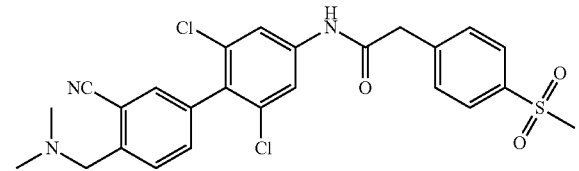

Step 1: Synthesis of 2',6'-dichloro-4-((dimethylamino)methyl)-4'-nitro-[1,1'-biphenyl]-3-carbonitrile 4-(Bromomethyl)-2',6'-dichloro-4'-nitro-[1,1'-biphenyl]-3-carbonitrile (1.2 g, 3.1 mmol), a solution of dimethylamine in tetrahydrofuran (4.5 mL, 9.3 mmol), potassium carbonate (1.27 g, 9.3 mmol) and acetonitrile (10 mL) were added in a 25 mL single-neck flask, and the mixture was reacted at room temperature for 2 hours. After completion of the reaction, water (20 mL) was added, and the mixture was extracted with ethyl acetate (3*10 mL). The organic layers were combined, washed with saturated sodium chloride, dried over anhydrous sodium sulfate, and concentrated in vacuo to remove the solvent. The crude was separated by a silica gel column (petroleum ether:acetic acid ester=10:1-5:1) to give a product (yellow oil, 800 mg), with a yield 73.4%. $^1$H NMR (400 MHz, CDCl$_3$) δ 8.33 (s, 2H), 7.76 (d, J=8.0 Hz, 1H), 7.58 (s, 1H), 7.49 (d, J=7.9 Hz, 1H), 3.75 (s, 2H), 2.39 (s, 6H).

Step 2: Synthesis of 4'-amino-2',6'-dichloro-4-((dimethylamino)methyl)-[1,1'-biphenyl]-3-carbonitrile 2',6'-Dichloro-4-((dimethylamino)methyl)-4'-nitro-[1,1'-biphenyl]-3-carbonitrile (800 mg, 2.29 mmol), ammonium formate (1.56 g, 22.9 mmol) and methanol/H₂O (10 mL/10 mL) were added in a 25 mL single-neck flask, then zinc powder (813 mg, 11.4 mmol) was added under stirring, and the reaction mixture was heated to react at 80° C. for 2 hours. After completion of the reaction, the mixture was cooled to room temperature and extracted with ethyl acetate (3*20 mL), to afford a product (yellow solid, 450 mg), with a yield of 61.6%.

Step 3: Synthesis of N-(2,6-dichloro-3'-cyano-4'-((dimethylamino)methyl)-[1,1'-biphenyl]-4-yl)-2-(4-(methyl sulfonyl)phenyl)acetamide The method is the same as in example 1. 4'-Amino-2',6'-dichloro-4-((dimethylamino)methyl)-[1,1'-biphenyl]-3-carbonitrile (200 mg, 0.63 mmol), 2-(4-(methylsulfonyl)phenyl)acetic acid (161 mg, 0.75 mmol), HATU (285 mg, 0.75 mmol), N,N-diisopropylethylamine (244 mg, 1.89 mmol) and dichloromethane (5 mL) were reacted at room temperature for 2 hours. The crude product was separated by a silica gel column (dichloromethane:methanol=50:1) to give a product (white solid, 310 mg), with a yield of 96.3%. ¹H NMR (400 MHz, CDCl₃) δ 7.95 (s, 1H), 7.72 (d, J=8.1 Hz, 2H), 7.54 (s, 2H), 7.41 (t, J=8.5 Hz, 4H), 7.32 (s, 1H), 7.24 (d, J=8.0 Hz, 1H), 3.66 (s, 2H), 3.51 (s, 2H), 2.87 (s, 3H), 2.16 (s, 6H). MS (ESI) m/z: 515.9 (M+1).

Example 35

N-(2,6-Dichloro-3'-cyano-4'-((dimethylamino) methyl)-[1,1'-biphenyl]-4-yl)-2-(4-(ethylsulfonyl) phenyl)acetamide

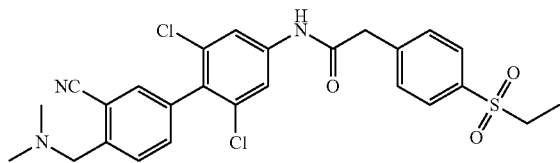 [SMILES: CCS(=O)(=O)c1ccc(CC(=O)Nc2cc(Cl)c(-c3ccc(CN(C)C)c(C#N)c3)c(Cl)c2)cc1]

4'-Amino-2',6'-dichloro-4-((dimethylamino)methyl)-[1,1'-biphenyl]-3-carbonitrile (70 mg, 0.22 mmol), 2-(4-(ethylsulfonyl)phenyl)acetic acid (52 mg, 0.23 mmol), HATU (105 mg, 0.28 mmol), N,N-diisopropylethylamine (77 μL, 0.56 mmol) and dichloromethane (2 mL) were added in a 10 mL microwave tube. The mixture was reacted at 80° C. under microwave for 1 hour. After completion of the reaction according to TLC, dichloromethane (20 mL) was added, and the mixture was washed with saturated ammonium chloride (30 mL). The organic layer was concentrated in vacuo to remove the solvent, and the resulting crude product was separated by a silica gel column (petroleum ether:ethyl acetate=1:1) to give a product (yellow solid, 120 mg), with a yield of 100%. ¹H NMR (400 MHz, CDCl₃) δ 7.90 (s, 1H), 7.89 (d, J=7.9 Hz, 2H), 7.69 (s, 2H), 7.54 (d, 2H), 7.53 (s, 1H), 7.44 (d, J=7.9 Hz, 1H), 3.84 (s, 2H), 3.75 (s, 2H), 3.13 (q, J=7.2 Hz, 2H), 2.38 (s, 6H), 1.30 (t, J=7.5 Hz, 3H). MS (ESI) m/z: 530.1 (M+1).

Example 36

N-(2,6-Dichloro-3'-cyano-4'-((ethyl(methyl)amino) methyl)-[1,1'-biphenyl]-4-yl)-2-(4-(ethylsulfonyl) phenyl)acetamide

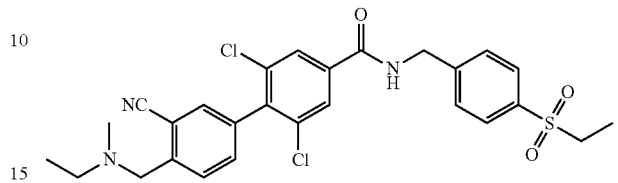

Step 1: Synthesis of 2',6'-dichloro-4-((ethyl(methyl) amino)methyl)-4'-nitro-[1,1'-biphenyl]-3-carbonitrile 4-(Bromomethyl)-2',6'-dichloro-4'-nitro-[1,1'-biphenyl]-3-carbonitrile (629 mg, 1.6 mmol), N-ethylmethylamine (280μ, 3.3 mmol), potassium carbonate (675 mg, 4.9 mmol) and acetonitrile (5 mL) were added in a 15 mL microwave tube, and the mixture was heated to react at 80° C. for 2 hours under microwave. After completion of the reaction, solvent was removed in vacuo, then water (20 mL) was added, and the mixture was extracted with ethyl acetate (3*10 mL). The organic layers were combined, washed with saturated sodium chloride, dried over anhydrous sodium sulfate, and concentrated in vacuo to remove the solvent. The residue was separated by a silica gel column (petroleum ether:acetic acid ester=10:1) to give a product (yellow solid, 230 mg), with a yield 39.5%. MS (ESI) m/z: 364.1 (M+1).

Step 2: Synthesis of 4'-amino-2',6'-dichloro-4-((ethyl(methyl)amino)methyl)-[1,1'-biphenyl]-3-carbonitrile 2',6'-Dichloro-4-((ethyl(methyl)amino)methyl)-4'-nitro-[1,1'-biphenyl]-3-carbonitrile (230 mg, 0.63 mmol), platinum dioxide (50 mg) and methanol (20 mL) were added in a 50 mL single-neck flask, and the mixture was stirred at room temperature for 1 hour under hydrogen atmosphere. After completion of the reaction, the mixture was filtered through Celite, and concentrated in vacuo to remove the solvent to afford a product (yellow solid, 130 mg), with a yield of 62.0%.

Step 3: Synthesis of N-(2,6-dichloro-3'-cyano-4'-((ethyl(methyl)amino)methyl)-[1,1'-biphenyl]-4-yl)-2-(4-(ethylsulfonyl)phenyl)acetamide 4'-Amino-2',6'-dichloro-4-((ethyl(methyl)amino)methyl)-[1,1'-biphenyl]-3-carbonitrile (130 mg, 0.39 mmol), 2-(4-(ethylsulfonyl)phenyl)acetic acid (220 mg, 0.82 mmol), HATU (312 mg, 0.82 mmol), N,N-diisopropylethylamine (244 mg, 1.89 mmol) and dichloromethane (20 mL) were added in a 50 mL single-neck flask, and the reaction mixture was stirred at room temperature overnight. The crude product was separated by a silica gel column (dichloromethane:methanol=200:3) to give a product (white solid, 70 mg), with a yield of 33.0%. ¹H NMR (400 MHz, CDCl₃) δ 8.15 (s, 1H), 7.85 (d, J=6.4 Hz, 2H), 7.71 (s, 2H), 7.65 (d, J=6.9 Hz, 1H), 7.56 (d, J=6.4 Hz, 2H), 7.50 (s, 1H), 7.42 (d, J=4.5 Hz, 1H), 3.83 (s, 2H), 3.77 (s, 2H), 3.74-3.60 (m, 2H), 3.19-3.10 (m, 3H), 2.61 (d, J=6.8 Hz, 2H), 2.29 (s, 3H), 1.30-1.27 (m, 3H), 1.19-1.12 (m, 3H). MS (ESI) m/z: 544.1 (M+1).

Example 37

N-(2,6-Dichloro-3'-cyano-4'-((diethylamino)methyl)-[1,1'-biphenyl]-4-yl)-2-(4-(ethylsulfonyl)phenyl)acetamide

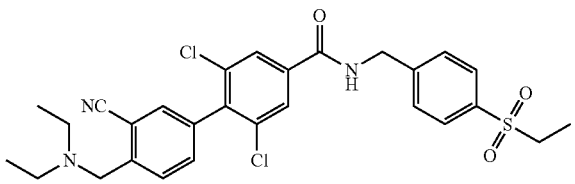 [SMILES: CCN(CC)Cc1ccc(-c2c(Cl)cc(C(=O)NCc3ccc(S(=O)(=O)CC)cc3)cc2Cl)cc1C#N]

The method is the same as in example 1. 4'-Amino-2',6'-dichloro-4-((diethylamino)methyl)-[1,1'-biphenyl]-3-carbonitrile (80 mg, 0.23 mmol), 2-(4-(ethylsulfonyl)phenyl)acetic acid (63 mg, 0.27 mmol), HATU (103 mg, 0.27 mmol), N,N-diisopropylethylamine (89 mg, 0.69 mmol) and dichloromethane (5 mL) were reacted at room temperature for 1 hour, and the crude product was separated by a silica gel column (petroleum ether:ethyl acetate=1:1-1:2) to give a product (white solid, 60 mg), with a yield of 46.8%. $^1$H NMR (400 MHz, CDCl$_3$) δ 9.14 (s, 1H), 7.82 (d, J=8.0 Hz, 2H), 7.74 (s, 2H), 7.71 (d, J=8.1 Hz, 1H), 7.54 (d, J=8.0 Hz, 2H), 7.49 (s, 1H), 7.41 (d, J=8.1 Hz, 1H), 3.82 (s, 2H), 3.16-3.11 (m, 2H), 2.84 (s, 2H), 2.61 (q, J=7.0 Hz, 4H), 1.28 (s, 3H), 1.08 (t, J=7.1 Hz, 6H). MS (ESI) m/z: 558.2 (M+1).

Example 38

N-(4'-(Azetidin-1-ylmethyl)-2,6-dichloro-3'-cyano-[1,1'-biphenyl]-4-yl)-2-(4-(ethylsulfonyl)phenyl)acetamide

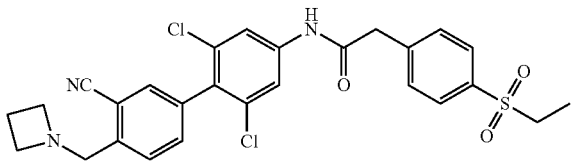 [SMILES: CCS(=O)(=O)c1ccc(CC(=O)Nc2cc(Cl)c(-c3ccc(CN4CCC4)c(C#N)c3)c(Cl)c2)cc1]

Step 1: Synthesis of 4-(azetidin-1-ylmethyl)-2',6'-dichloro-4'-nitro-[1,1'-biphenyl]-3-carbonitrile 4-(Bromomethyl)-2',6'-dichloro-4'-nitro-[1,1'-biphenyl]-3-carbonitrile (200 mg, 0.52 mmol), azetidine (61 mg, 1.04 mmol), potassium carbonate (212 mg, 1.56 mmol), acetonitrile (5 mL) were added in a 25 mL single-neck flask, and the mixture was reacted at room temperature for 1 hour. After completion of the reaction, water (20 mL) was added, and the mixture was extracted with ethyl acetate (3*10 mL). The organic layers were combined, washed with saturated sodium chloride, dried over anhydrous sodium sulfate, and concentrated in vacuo to remove the solvent to obtain a crude product (yellow oil, 160 mg), with a yield of 85.1%. $^1$H NMR (400 MHz, CDCl$_3$) δ 8.29 (s, 2H), 7.69 (d, J=8.1 Hz, 1H), 7.52 (s, 1H), 7.44 (dd, J=8.0, 1.4 Hz, 1H), 3.87 (s, 2H), 3.37 (t, J=7.0 Hz, 4H), 2.21-2.11 (m, 2H).

Step 2: Synthesis of 4'-amino-4-(azetidin-1-ylmethyl)-2',6'-dichloro-[1,1'-biphenyl]-3-carbonitrile 4-(Azetidin-1-ylmethyl)-2',6'-dichloro-4'-nitro-[1,1'-biphenyl]-3-carbonitrile (160 mg, 0.44 mmol), methanol (2 mL) and platinum dioxide (16 mg) were added in a 25 mL single-neck flask with a hydrogen balloon equipped, and the mixture was reacted at room temperature for 20 minutes under hydrogen atmosphere. The mixture was filtered through Celite, and concentrated to remove the solvent to afford a product (yellow oil, 150 mg). $^1$H NMR (400 MHz, CDCl$_3$) δ 7.62-7.50 (m, 2H), 7.44 (d, J=8.1 Hz, 1H), 6.71 (s, 2H), 3.90 (s, 2H), 3.84 (s, 2H), 3.36 (t, J=7.0 Hz, 4H), 2.20-2.10 (m, 2H). MS (ESI) m/z: 332.0 (M+1).

Step 3: Synthesis of N-(4'-(azetidin-1-ylmethyl)-2,6-dichloro-3'-cyano-[1,1'-biphenyl]-4-yl)-2-(4-(ethylsulfonyl)phenyl)acetamide The method is the same as in example 1. 4'-Amino-4-(azetidin-1-ylmethyl)-2',6'-dichloro-[1,1'-biphenyl]-3-carbonitrile (80 mg, 0.24 mmol), 2-(4-(ethylsulfonyl)phenyl)acetic acid (66 mg, 0.28 mmol), HATU (106 mg, 0.28 mmol), N,N-diisopropylethylamine (93 mg, 0.72 mmol) and dichloromethane (5 mL) were reacted at room temperature for 3 hours, and the crude product was separated by a silica gel column (dichloromethane:methanol=20:1) to give a product (white solid, 54 mg), with a yield of 41.8%. MS (ESI) m/z: 542.0 (M+1).

Example 39

N-(2,6-Dichloro-3'-cyano-4'-(pyrrolidin-1-ylmethyl)-[1,1'-biphenyl]-4-yl)-2-(4-(ethylsulfonyl)phenyl)acetamide

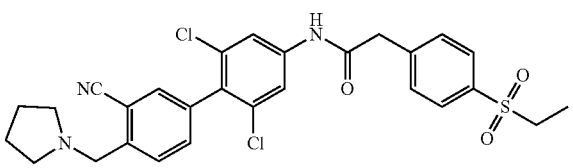 [SMILES: CCS(=O)(=O)c1ccc(CC(=O)Nc2cc(Cl)c(-c3ccc(CN4CCCC4)c(C#N)c3)c(Cl)c2)cc1]

Step 1: Synthesis of 2',6'-dichloro-4'-nitro-4-(pyrrolidin-1-ylmethyl)-[1,1'-biphenyl]-3-carbonitrile 4-(Bromomethyl)-2',6'-dichloro-4'-nitro-[1,1'-biphenyl]-3-carbonitrile (200 mg, 0.52 mmol), pyrrolidine (74 mg, 1.04 mmol), potassium carbonate (212 mg, 1.56 mmol) and acetonitrile (5 mL) were added in a 25 mL single-neck flask, and the mixture was stirred at room temperature for 3 hours. After completion of the reaction, water (20 mL) was added, and the mixture was extracted with ethyl acetate (3*10 mL). The organic layers were combined, washed with saturated sodium chloride, dried over anhydrous sodium sulfate, and concentrated in vacuo to remove the solvent to obtain a crude product (yellow oil, 150 mg), with a yield 76.5%. $^1$H NMR (400 MHz, CDCl$_3$) δ 8.31 (s, 1H), 7.80 (d, J=7.9 Hz, 1H), 7.54 (s, 1H), 7.46 (d, J=7.9 Hz, 1H), 3.95 (s, 2H), 2.67 (s, 4H), 1.86 (s, 4H).

Step 2: Synthesis of 4'-amino-4-(pyrrolidin-1-ylmethyl)-2',6'-dichloro-[1,1'-biphenyl]-3-carbonitrile 2',6'-Dichloro-4'-nitro-4-(pyrrolidin-1-ylmethyl)-[1,1'-biphenyl]-3-carbonitrile (150 mg, 0.40 mmol), methanol (2 mL) and platinum dioxide (15 mg) were added in a 25 mL single-neck flask with a hydrogen balloon equipped, and the mixture was reacted at room temperature for 2 hours under hydrogen atmosphere. Then the mixture was filtered through Celite, and solvent was removed to afford a product (yellow oil, 120 mg). $^1$H NMR (400 MHz, CDCl$_3$) δ 7.64 (d, J=8.0 Hz, 1H), 7.53 (s, 1H), 7.44 (d, J=8.0 Hz, 1H), 6.71 (s, 2H), 3.90 (s, 4H), 2.64 (s, 4H), 1.83 (s, 4H). MS (ESI) m/z: 346.0 (M+1).

Step 3: Synthesis of N-(2,6-dichloro-3'-cyano-4'-(pyrrolidin-1-ylmethyl)-[1,1'-biphenyl]-4-yl)-2-(4-(ethylsulfonyl)phenyl)acetamide The method is the same as in example 1. 4'-Amino-4-(pyrrolidin-1-ylmethyl)-2',6'-dichloro-[1,1'-biphenyl]-3-carbonitrile (100 mg, 0.29 mmol), 2-(4-(ethylsulfonyl)phenyl) acetic acid (80 mg, 0.35 mmol), HATU (133 mg, 0.35 mmol), N,N-diisopropylethylamine (112 mg, 0.87 mmol) and dichloromethane (5 mL) were reacted at room temperature for 3 hours, and the crude product was separated by a silica gel column (petroleum ether:ethyl acetate=1:2) to give a product (white solid, 96 mg), with a yield of 75.0%. $^1$H NMR (400 MHz, CDCl$_3$) δ 9.40 (s, 1H), 7.80 (d, J=7.7 Hz, 2H), 7.72 (s, 2H), 7.63 (d, J=8.0 Hz, 1H), 7.53 (d, J=7.8 Hz, 2H), 7.48 (s, 1H), 7.40 (d, J=8.0 Hz, 1H), 3.86 (s, 2H), 3.80 (s, 2H), 3.10 (q, J=7.3 Hz, 2H), 2.60 (s, 4H), 1.79 (s, 4H), 1.25 (t, J=7.4 Hz, 3H). MS (ESI) m/z: 556.0 (M+1).

Example 40

N-(2,6-Dichloro-3'-cyano-4'-(2-methylprop-1-en-1-yl)-[1,1'-biphenyl]-4-yl)-2-(4-(ethylsulfonyl)phenyl)acetamide

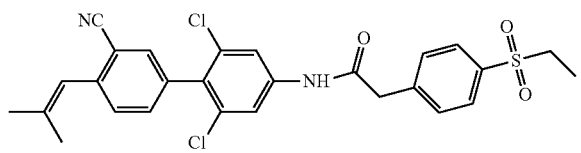

Step 1: Synthesis of 4'-amino-2',6'-dichloro-4-(2-methylprop-1-en-1-yl)-[1,1'-biphenyl]-3-carbonitrile 2',6'-Dichloro-4-(2-methylprop-1-en-1-yl)-4'-nitro-[1,1'-biphenyl]-3-carbonitrile (200 mg, 0.58 mmol), tin(II) chloride dihydrate (550 mg, 1.73 mmol), ethanol (10 mL) and concentrated hydrochloric acid (0.25 mL) were added in a 100 mL single-neck flask, then the mixture was heated to react at 60° C. for 1 hour. After the materials had all reacted when being determined by TLC, the mixture was concentrated in vacuo to remove ethanol, and the mixture was adjusted to pH 9 with saturated sodium carbonate solution and extracted with ethyl acetate (3*20 mL). The combined organic layers were washed with saturated sodium chloride, dried over anhydrous sodium sulfate, and filtered. The filtrate was concentrated in vacuo to remove the solvent to give a product (yellow solid, 120 mg), which was used for the next reaction directly.

Step 2: Synthesis of N-(2,6-dichloro-3'-cyano-4'-(2-methylprop-1-en-1-yl)-[1,1'-biphenyl]-4-yl)-2-(4-(ethylsulfonyl)phenyl)acetamide 4'-Amino-2',6'-dichloro-4-(2-methylprop-1-en-1-yl)-[1,1'-biphenyl]-3-carbonitrile (110 mg, 0.35 mmol), 2-(4-(ethylsulfonyl)phenyl)acetic acid (95 mg, 0.42 mmol), HATU (160 mg, 0.42 mmol), N,N-diisopropylethylamine (135 mg, 1.05 mmol) and dichloromethane (5 mL) were added in a 25 mL single-neck flask, and the mixture was reacted at room temperature for 3 hours. After the materials had all reacted when being determined by TLC, dichloromethane (20 mL) was added, and the mixture was washed with saturated ammonium chloride (30 mL). The organic layer was concentrated in vacuo to remove the solvent, and the resulting crude product was separated by a silica gel column (petroleum ether:ethyl acetate=2:1-1:1) to give a product (white solid, 140 mg), with a yield of 76.5%. $^1$H NMR (400 MHz, CDCl$_3$) δ 7.84 (t, J=10.8 Hz, 3H), 7.68 (s, 2H), 7.56-7.49 (m, 3H), 7.44 2H), 1.99 (s, 3H), 1.88 (s, 3H), 1.30 (t, J=7.4 Hz, 3H). MS(ESI) m/z: 524.8 (M−1).

Example 41

N-(2,6-Dichloro-3'-cyano-4'-(2-methylbutyl)-[1,1'-biphenyl]-4-yl)-2-(4-(ethylsulfonyl)phenyl)acetamide

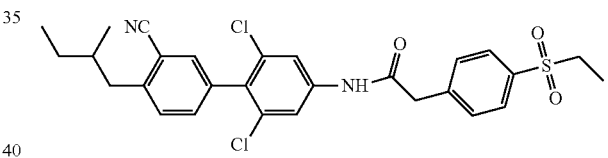

Step 1: Synthesis of (E)-5-bromo-2-(2-methylbut-1-en-1-yl)benzonitrile and (Z)-5-bromo-2-(2-methylbut-1-en-1-yl)benzonitrile Diethyl (4-bromo-2-cyanobenzyl)phosphonate (8 g, 24 mmol) and anhydrous tetrahydrofuran (80 mL) were added in a 250 mL single-neck flask, and the mixture was stirred and cooled in an ice bath for 5 minutes. NaH (1.15 g, 28.6 mmol) was added in portions and the reaction was continued in the ice bath for 30 minutes. Then a solution of butan-2-one (3.45 g, 48 mmol) diluted with anhydrous tetrahydrofuran (5 mL) was added dropwise to the reaction mixture. The ice bath was removed and the mixture was stirred at room temperature overnight. Water was added to quench the reaction, and the mixture was extracted with ethyl acetate (3*30 mL). The organic layers were concentrated in vacuo to remove the solvent, and separated by a silica gel column (petroleum ether:ethyl acetate=100:1) to give a mixture of cis-trans isomers at a ratio of 3:1 (colorless oil, 3.5 g), with a yield of 58.3%. $^1$H NMR (400 MHz, CDCl$_3$) δ 7.74 (d, J=2.0 Hz, 1H), 7.63 (dd, J=8.5, 1.8 Hz, 1H), 7.23 (d, J=8.4 Hz, 0.8H), 7.19 (d, J=8.4 Hz, 0.27H), 6.34 (s, 0.8H), 6.31 (s, 0.21H), 2.23 (t, J=7.4 Hz, 1.84H), 2.15 (d, J=7.6 Hz, 0.68H), 1.93 (d, J=1.4 Hz, 0.9H), 1.79 (d, J=1.1 Hz, 2.68H), 1.14 (t, J=7.5 Hz, 2.7H), 1.07 (t, J=7.6 Hz, 0.9H).

Step 2: Synthesis of (E)-2-(2-methylbut-1-en-1-yl)-5-(4,4,5,5-tetramethyl-1,3,2-dioxaborolan-2-yl)benzonitrile and (Z)-2-(2-methylbut-1-en-1-yl)-5-(4,4,5,5-tetramethyl-1,3,2-dioxaborolan-2-yl)benzonitrile A mixture of (E)-5-bromo-2-(2-methylbut-1-en-1-yl)benzonitrile and (Z)-5-bromo-2-(2-methylbut-1-en-1-yl)benzonitrile (2.5 g, 9.5 mmol), bis(pinacolato)diboron (2.59 g, 11.4 mmol), Pd(dppf)Cl$_2$ (347 mg, 0.48 mmol), potassium acetate (2.79 g, 28.5 mmol) and 1,4-dioxane (40 mL) were added in a microwave tube, and the mixture was heated to react at 120° C. under microwave for 3 hours. After completion of the reaction, the mixture was cooled to room temperature, extracted with ethyl acetate (3*20 mL), and washed with saturated sodium chloride. The organic layers were concentrated in vacuo to remove the solvent, and the residue was separated by a silica gel column (petroleum ether:ethyl acetate=100:1) to give a product (white solid, 2.8 g), with a yield of 95.2%. $^1$H NMR (400 MHz, CDCl$_3$) δ 8.05 (s, 1H), 7.90 (d, J=7.8 Hz, 1H), 7.35 (d, J=7.8 Hz, 0.74H), 7.31 (d, J=7.8 Hz, 0.26H), 6.43 (s, 0.74H), 6.41 (s, 0.26H), 2.24 (q, J=7.4 Hz, 1.48H), 2.16 (q, J=7.7 Hz, 0.52H), 1.94 (s, 0.78H), 1.80 (s, 2.22H), 1.34 (s, 12H), 1.14 (t, J=7.5 Hz, 2.22H), 1.05 (t, J=7.5 Hz, 0.78H).

Step 3: Synthesis of (E)-2',6'-dichloro-4-(2-methylbut-1-en-1-yl)-4'-nitro-[1l'-biphenyl]-3-carbonitrile and (Z)-2',6'-dichloro-4-(2-methylbut-1-en-1-yl)-4'-nitro-[1,1'-biphenyl]-3-carbonitrile A mixture of (E)-2-(2-methylbut-1-en-1-yl)-5-(4,4,5,5-tetramethyl-1,3,2-dioxaborolan-2-yl)benzonitrile and (Z)-2-(2-methylbut-1-en-1-yl)-5-(4,4,5,5-tetramethyl-1,3,2-dioxaborolan-2-yl)benzonitrile (4.5 g, 15.2 mmol), 1,3-dichloro-2-iodo-5-nitrobenzene (5.78 g, 18.2 mmol), sodium carbonate (4.8 g, 45.6 mmol), PdCl$_2$(dtbpf) (495 mg, 0.76 mmol) and 2 wt % Tween 20 in water (50 mL) were added in a 100 mL single-neck flask, and the mixture was heated to react at 80° C. for 30 minutes. After completion of the reaction, the mixture was extracted with ethyl acetate (5*20 mL). The organic layers were combined, washed with saturated sodium chloride, and concentrated in vacuo to remove the solvent. The residue was separated by a silica gel column (petroleum ether:ethyl acetate=10:1) to give a product (yellow oil, 3.9 g), with a yield of 91.7%. $^1$H NMR (400 MHz, CDCl$_3$) δ 8.30 (s, 2H), 7.53 (d, J=8.4 Hz, 1.74H), 7.47 (s, 0.24H), 7.41 (dd, J=8.2, 1.7 Hz, 1H), 6.50 (s, 0.74H), 6.46 (s, 0.26H), 2.36-2.20 (m, 2H), 1.99 (s, 0.78H), 1.90 (s, 2.22), 1.18 (t, J=7.5 Hz, 2.22H), 1.14 (t, J=7.6 Hz, 0.78H).

Step 4: Synthesis of 4'-amino-2',6'-dichloro-4-(2-methylbutyl)-[1,1'-biphenyl]-3-carbonitrile A mixture of (E)-2',6'-dichloro-4-(2-methylbut-1-en-1-yl)-4'-nitro-[1,1'-biphenyl]-3-carbonitrile and (Z)-2',6'-dichloro-4-(2-methylbut-1-en-1-yl)-4'-nitro-[1,1'-biphenyl]-3-carbonitrile (600 mg, 1.66 mmol), platinum dioxide (50 mg) and methanol (10 mL) were added in a 50 mL single-neck flask, and the mixture was reacted at room temperature for 30 minutes under hydrogen atmosphere, then additional platinum dioxide (50 mg) was added. The reaction was monitored by LC-MS, and was stopped immediately after completion. The mixture was filtered through Celite, and the filtrate was concentrated in vacuo. The residue was separated by a silica gel column (petroleum ether:ethyl acetate=50:1-10:1) to give a product (white solid, 280 mg), with a yield of 50.6%. $^1$H NMR (400 MHz, CDCl$_3$) δ 7.49 (d, J=1.3 Hz, 1H), 7.37 (dd, J=8.0, 1.7 Hz, 1H), 7.30 (d, J=8.1 Hz, 1H), 6.73 (s, 2H), 2.98 (d, J=7.6 Hz, 3H), 2.70 (dt, J=15.4, 7.8 Hz, 1H), 2.13-2.06 (m, 2H), 1.89-1.78 (m, 4H). MS (ESI) m/z: 333.1 (MH+).

Step 5: Synthesis of N-(2,6-dichloro-3'-cyano-4'-(2-methylbutyl)-[1,1'-biphenyl]-4-yl)-2-(4-(ethylsulfonyl)phenyl)acetamide 4'-Amino-2',6'-dichloro-4-(2-methylbutyl)-[1,1'-biphenyl]-3-carbonitrile (80 mg, 0.24 mmol), 2-(4-(ethylsulfonyl)phenyl)acetic acid (65 mg, 0.28 mmol), HATU (106 mg, 0.28 mmol), N,N-diisopropylethylamine (93 mg, 0.72 mmol) and dichloromethane (5 mL) were added in a 25 mL single-neck flask, the mixture was reacted at room temperature overnight. After the materials had all reacted when being determined by TLC, dichloromethane (20 mL) was added, and the mixture was washed with saturated ammonium chloride (30 mL) and concentrated in vacuo to afford a crude product, which was separated by preparative thin layer chromatography (petroleum ether:ethyl acetate=2:1-1:1) to give a product (white solid, 110 mg), with a yield of 84.6%. $^1$H NMR (400 MHz, CD$_3$OD) δ 7.86 (d, J=8.2 Hz, 2H), 7.76 (s, 2H), 7.61 (d, J=8.1 Hz, 2H), 7.51 (s, 1H), 7.45 (d, J=8.0 Hz, 1H), 7.41 (d, J=8.0 Hz, 1H), 3.84 (s, 2H), 3.18 (q, J=7.4 Hz, 2H), 2.92 (dd, J=13.4, 6.0 Hz, 1H), 2.62 (dd, J=13.3, 8.6 Hz, 1H), 1.79 (dq, J=13.8, 6.9 Hz, 1H), 1.49-1.39 (m, 1H), 1.33-1.27 (m, 1H), 1.19 (t, J=7.4 Hz, 3H), 0.95 (t, J=7.4 Hz, 3H), 0.90 (d, J=6.6 Hz, 3H). MS (ESI) m/z: 540.8 (M−1).

Example 42

N-(2,6-Dichloro-3'-cyano-4'-(2-methylbut-1-en-1-yl)-[1,1'-biphenyl]-4-yl)-2-(4-(ethylsulfonyl)phenyl)acetamide)

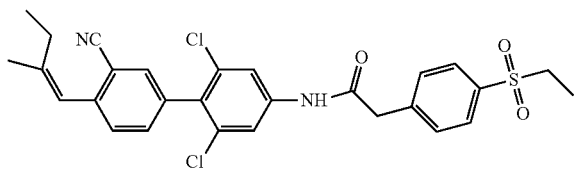 [SMILES: CC/C(C)=C\c1ccc(-c2c(Cl)cc(NC(=O)Cc3ccc(S(=O)(=O)CC)cc3)cc2Cl)cc1C#N]

Step 1: Synthesis of 4'-amino-2',6'-dichloro-4-(2-methylbut-1-en-1-yl)-[1,1'-biphenyl]-3-carbonitrile 2',6'-Dichloro-4-(2-methylbut-1-en-1-yl)-4'-nitro-[1,1'-biphenyl]-3-carbonitrile (200 mg, 0.55 mmol), tin(II) chloride dihydrate (375 mg, 1.66 mmol), ethanol (5 mL) and concentrated hydrochloric acid (0.20 mL) were added in a 100 mL single-neck flask, and the mixture was heated to react at 60° C. for 1 hour. After the materials had all reacted when being determined by TLC, the mixture was concentrated in vacuo to remove ethanol, then the mixture was adjusted to pH 9 with saturated sodium carbonate solution and extracted with ethyl acetate (3*20 mL). The organic layers were combined, washed with saturated sodium chloride, dried over anhydrous sodium sulfate, filtered, and concentrated in vacuo to remove the solvent to give a product (white solid, 120 mg), with a yield of 65.2%.

Step 2: Synthesis of N-(2,6-dichloro-3'-cyano-4'-(2-methylbut-1-en-1-yl)-[1,1'-biphenyl]-4-yl)-2-(4-(ethylsulfonyl)phenyl)acetamide 4'-Amino-2',6'-dichloro-4-(2-methylbut-1-en-1-yl)-[1,1'-biphenyl]-3-carbonitrile (80 mg, 0.24 mmol), 2-(4-(ethylsulfonyl)phenyl)acetic acid (66 mg, 0.29 mmol), HATU (110 mg, 0.29 mmol), N,N-diisopropylethylamine (93 mg, 0.72 mmol) and dichloromethane (5 mL) were added in a 25 mL single-neck flask, and the mixture was reacted at room temperature for 3 hours. After the materials had all reacted when being determined by TLC, dichloromethane (20 mL) was added, and the mixture was washed with saturated ammonium chloride (30 mL). The organic layer was concentrated to remove the solvent, and the resulting crude product was separated by a silica gel column (petroleum ether:ethyl acetate=1:1-1:2) to give a product (white solid, 95 mg), with a yield of 87.7%. $^1$H NMR (400 MHz, CDCl$_3$) δ 7.86 (d, J=8.2 Hz, 2H), 7.68 (s, 2H), 7.52 (dd, J=7.2, 4.9 Hz, 3H), 7.45 (d, J=8.1 Hz, 1H), 7.39 (dd, J=7.9, 1.8 Hz, 1H), 6.46 (d, J=12.8 Hz, 1H), 3.83 (s, 2H), 3.14 (q, J=7.4 Hz, 2H), 2.28 (q, J=7.3 Hz, 2H), 1.92 (s, 3H), 1.30 (t, J=7.4 Hz, 3H), 1.20-1.08 (t, J=7.3 Hz, 3H). MS (ESI) m/z: 538.8 (M−1).

Example 43

(N-(2,6-Dichloro-3'-cyano-4'-(cyclobutylmethyl)-[1,1'-biphenyl]-4-yl)-2-(4-(ethylsulfonyl)phenyl)acetamide)

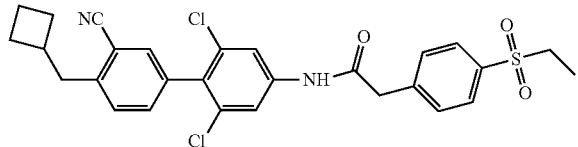 [SMILES: CCS(=O)(=O)c1ccc(CC(=O)Nc2cc(Cl)c(-c3ccc(CC4CCC4)c(C#N)c3)c(Cl)c2)cc1]

Step 1: Synthesis of 5-bromo-2-(cyclobutylidenemethyl)benzonitrile

Diethyl (4-bromo-2-cyanobenzyl)phosphonate (6 g, 18 mmol) and anhydrous tetrahydrofuran (60 mL) were added in a 150 mL single-neck flask, and the mixture was cooled in an ice bath under stirring for 5 minutes. NaH (434 mg, 10.8 mmol) was added in portions, and the reaction was continued in the ice bath for 30 minutes. Then cyclobutanone (1.26 g, 18 mmol) diluted in anhydrous tetrahydrofuran (5 mL) was added to the reaction mixture dropwise, then the ice bath was removed and the mixture was stirred at room temperature overnight. Water was added to quench the reaction, and the mixture was extracted with ethyl acetate (3*30 mL) and the organic layers were concentrated in vacuo to remove the solvent. The residue was separated by a silica gel column (petroleum ether:ethyl acetate=100:1) to give a product (white solid, 3.3 g), with a yield of 49.1%. $^1$H NMR (400 MHz, CDCl$_3$) δ 7.70 (d, J=2.0 Hz, 1H), 7.59 (dd, J=8.6, 2.0 Hz, 1H), 7.23 (d, J=8.6 Hz, 1H), 6.45-6.38 (m, 1H), 3.00 (t, J=7.8 Hz, 2H), 2.93 (dd, J=12.2, 4.7 Hz, 2H), 2.21-2.09 (m, 2H).

Step 2: Synthesis of 2-(cyclobutylidenemethyl)-5-(4,4,5,5-tetramethyl-1,3,2-dioxaborolan-2-yl)benzonitrile 5-Bromo-2-(cyclobutylidenemethyl)benzonitrile (3 g, 12.1 mmol), bis(pinacolato)diboron (4.2 g, 18.1 mmol), Pd(dppf)Cl$_2$ (438 mg, 0.6 mmol), potassium acetate (3.56 g, 36.3 mmol) and N,N-dimethylformamide (20 mL) were added in a microwave tube, then nitrogen gas was bubbled through the mixture for 5 minutes, and the mixture was reacted at 120° C. under microwave for 1 hour. After completion of the reaction, the mixture was cooled, diluted with ethyl acetate (20 mL), and washed with water for five times and then with saturated sodium chloride once. The organic layers were combined and concentrated in vacuo to remove the solvent. The residue was separated by a silica gel column (petroleum ether: ethyl acetate=10:1) to give a product (white solid, 3.7 g), with a yield of 94.4%. $^1$H NMR (400 MHz, CDCl$_3$) δ 8.03 (s, 1H), 7.87 (d, J=8.0 Hz, 1H), 7.35 (d, J=8.0 Hz, 1H), 6.53-6.46 (m, 1H), 3.05 (t, J=7.4 Hz, 2H), 2.95 (t, J=7.6 Hz, 2H), 2.14 (p, J=7.9 Hz, 2H), 1.34 (s, 13H).

Step 3: Synthesis of 2',6'-dichloro-4-(cyclobutylidenemethyl)-4'-nitro-[1,1'-biphenyl]-3-carbonitrile 2-(Cyclobutylidenemethyl)-5-(4,4,5,5-tetramethyl-1,3,2-dioxaborolan-2-yl)benzonitrile (3 g, 10.1 mmol), 1,3-dichloro-2-iodo-5-nitrobenzene (2.68 g, 8.4 mmol), sodium carbonate (2.67 g, 25.2 mmol), PdCl$_2$(dtbpf) (273 mg, 0.42 mmol) and 2 wt % Tween 20 in water (30 mL) were added in a 100 mL single-neck flask, and the mixture was heated to react at 80° C. under microwave for 2 hours. After completion of the reaction, the mixture was extracted with ethyl acetate (5*20 mL). The organic layers were combined and washed with saturated sodium chloride, and concentrated in vacuo to remove the solvent. The residue was separated by a silica gel column (petroleum ether:ethyl acetate=10:1) to give a product (yellow solid, 2.4 g), with a yield of 82.3%. $^1$H NMR (400 MHz, CDCl$_3$) δ 8.30 (s, 2H), 7.52 (d, J=8.3 Hz, 2H), 7.38 (dd, J=8.2, 1.7 Hz, 1H), 6.56 (s, 1H), 3.10 (d, J=7.9 Hz, 2H), 2.99 (d, J=7.9 Hz, 2H), 2.24-2.14 (m, 3H).

Step 4: Synthesis of 4'-amino-2',6'-dichloro-4-(cyclobutylmethyl)-[1,1'-biphenyl]-3-carbonitrile 2',6'-Dichloro-4-(cyclobutylidenemethyl)-4'-nitro-[1,1'-biphenyl]-3-carbonitrile (500 mg, 1.39 mmol), platinum dioxide (50 mg) and methanol (10 mL) were added in a 50 mL single-neck flask, and the mixture was reacted at room temperature for 30 minutes under hydrogen atmosphere, then additional platinum dioxide (50 mg) was added. The reaction was monitored by LC-MS, and was stopped immediately after completion. The mixture was filtered through Celite, and the filtrate was concentrated in vacuo and separated by a silica gel column (petroleum ether:ethyl acetate=10:1) to give a product (white solid, 202 mg), with a yield of 21.7%. $^1$H NMR (400 MHz, CDCl$_3$) δ 7.49 (d, J=1.3 Hz, 1H), 7.37 (dd, J=8.0, 1.7 Hz, 1H), 7.30 (d, J=8.1 Hz, 1H), 6.73 (s, 2H), 2.98 (d, J=7.6 Hz, 3H), 2.70 (dt, J=15.4, 7.8 Hz, 1H), 2.13-2.06 (m, 2H), 1.89-1.78 (m, 4H). MS (ESI) m/z: 331.1 (MH+).

Step 5: Synthesis of N-(2,6-dichloro-3'-cyano-4'-(cyclobutylmethyl)-[1,1'-biphenyl]-4-yl)-2-(4-(ethylsulfonyl)phenyl)acetamide 4'-Amino-2',6'-dichloro-4-(cyclobutylmethyl)-[1,1'-biphenyl]-3-carbonitrile (45 mg, 0.13 mmol), 2-(4-(ethylsulfonyl)phenyl)acetic acid (37 mg, 0.16 mmol), HATU (61 mg, 0.16 mmol), N,N-diisopropylethylamine (50 mg, 0.39 mmol) and dichloromethane (2 mL) were added in a 25 mL single-neck flask, and the mixture was reacted at room temperature overnight. After the materials had all reacted when being determined by TLC, dichloromethane (20 mL) was added, and the mixture was washed with saturated ammonium chloride (30 mL). The organic layer was concentrated in vacuo to remove the solvent, and the resulting crude product was separated by preparative thin layer chromotography (petroleum ether:ethyl acetate=1:1) to give a product (white solid, 50 mg), with a yield of 67.6%. $^1$H NMR (400 MHz, CDCl$_3$) δ 8.59 (s, 1H), 7.80 (d, J=8.0 Hz, 2H), 7.70 (s, 2H), 7.50 (d, J=8.0 Hz, 2H), 7.46 (s, 1H), 7.34 (s, 2H), 3.80 (s, 2H), 3.13 (q, J=7.4 Hz, 2H), 2.97 (d, J=7.5 Hz, 2H), 2.75-2.63 (m, 1H), 2.07 (dd, J=7.7, 2.9 Hz, 2H), 1.90-1.76 (m, 4H), 1.28 (t, J=7.4 Hz, 3H). MS (ESI) m/z: 538.8 (M−1).

Example 44

N-(2,6-Dichloro-3'-cyano-4'-(cyclobutylidenemethyl)-[1,1'-biphenyl]-4-yl)-2-(4-(ethylsulfonyl)phenyl)acetamide

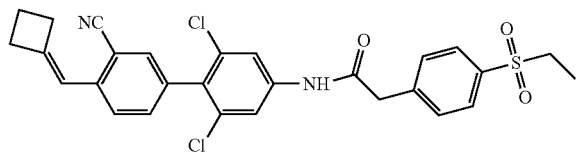

Step 1: Synthesis of 4'-amino-2',6'-dichloro-4-(cyclobutylidenemethyl)-[1,1'-biphenyl]-3-carbonitrile 2',6'-Dichloro-4-(cyclobutylidenemethyl)-4'-nitro-[1,1'-biphenyl]-3-carbonitrile (200 mg, 0.56 mmol), tin(II) chloride dihydrate (381 mg, 1.68 mmol), ethanol (5 mL) and concentrated hydrochloric acid (0.20 mL) were added in a 100 mL single-neck flask, and the mixture was heated to react at 60° C. for 1 hour. After the materials had all reacted when being determined by TLC, the mixture was concentrated in vacuo to remove ethanol, then the mixture was adjusted to pH 9 with saturated sodium carbonate solution and extracted with ethyl acetate (3*20 mL). The organic layers were combined, washed once with saturated sodium chloride, dried over anhydrous sodium sulfate, filtered, and concentrated in vacuo to remove the solvent to give a product (white solid, 160 mg), with a yield of 87.4%.

Step 2: Synthesis of N-(2,6-dichloro-3'-cyano-4'-(cyclobutylidenemethyl)-[1,1'-biphenyl]-4-yl)-2-(4-(ethylsulfonyl)phenyl)acetamide 4'-Amino-2',6'-dichloro-4-(cyclobutylidenemethyl)-[1,1'-biphenyl]-3-carbonitrile (80 mg, 0.24 mmol), 2-(4-(ethylsulfonyl)phenyl)acetic acid (67 mg, 0.29 mmol), HATU (148 mg, 0.39 mmol), N,N-diisopropylethylamine (93 mg, 0.72 mmol) and dichloromethane (5 mL) were added in a 25 mL single-neck flask, and the mixture was reacted at room temperature for 3 hours. After the materials had all reacted when being determined by TLC, dichloromethane (20 mL) was added, and the mixture was washed with saturated ammonium chloride (30 mL). The organic layer was concentrated in vacuo to remove the solvent, and the resulting crude product was separated by a silica gel column (petroleum ether:ethyl acetate=1:1-1:2) to give a product (white solid, 114 mg), with a yield of 87.0%. $^1$H NMR (400 MHz, CDCl$_3$) δ 8.23 (s, 1H), 7.82 (d, J=8.0 Hz, 2H), 7.69 (s, 2H), 7.51 (d, J=8.0 Hz, 2H), 7.46 (d, J=3.1 Hz, 1H), 7.45 (d, J=8.5 Hz, 1H), 7.35 (d, J=8.2 Hz, 1H), 6.52 (s, 1H), 3.81 (s, 2H), 3.17-3.11 (q, J=7.4 Hz, 2H), 3.11-3.05 (m, 2H), 2.97 (t, J=7.3 Hz, 2H), 2.22-2.10 (m, 2H), 1.29 (t, J=7.4 Hz, 3H). MS (ESI) m/z: 536.8 (M−1).

Example 45

N-(2,6-Dichloro-3'-cyano-4'-(cyclopentylmethyl)-[1,1'-biphenyl]-4-yl)-2-(4-(ethylsulfonyl)phenyl)acetamide

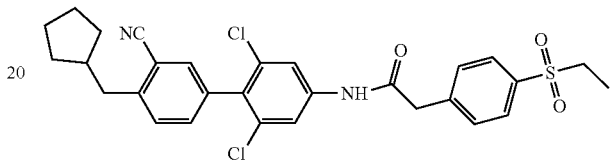

Step 1: Synthesis of 5-bromo-2-(cyclopentylidenemethyl)benzonitrile

Diethyl (4-bromo-2-cyanobenzyl)phosphonate (7 g, 21 mmol) and anhydrous tetrahydrofuran (70 mL) were added in a 150 mL single-neck flask, and the mixture was cooled in an ice bath under stirring for 5 minutes. NaH (1 g, 25 mmol) was added in portions, and the mixture was stirred in the ice bath for 30 minutes. Then cyclopentanone (3.53 g, 21 mmol) diluted in anhydrous tetrahydrofuran (5 mL) was added to the reaction mixture dropwise, then the ice bath was removed and the mixture was reacted at room temperature overnight. Water was added to quench the reaction, and the mixture was extracted with ethyl acetate (3*30 mL). The organic layers were concentrated in vacuo to remove the solvent, and the residue was separated by a silica gel column (petroleum ether:ethyl acetate=100:1) to give a product (colorless oil, 2.5 g), with a yield of 45.5%. $^1$H NMR (400 MHz, CDCl$_3$) δ 7.71 (d, J=2.1 Hz, 1H), 7.61 (dd, J=8.6, 2.0 Hz, 1H), 7.38 (d, J=8.6 Hz, 1H), 6.63-6.58 (m, 1H), 2.54 (t, J=7.2 Hz, 2H), 2.46 (t, J=7.1 Hz, 2H), 1.83-1.75 (m, 2H), 1.74-1.66 (m, 2H).

Step 2: Synthesis of 2-(cyclopentylidenemethyl)-5-(4,4,5,5-tetramethyl-1,3,2-dioxaborolan-2-yl)benzonitrile 5-Bromo-2-(cyclopentylidenemethyl)benzonitrile (2.5 g, 9.5 mmol), bis(pinacolato)diboron (2.59 g, 11.4 mmol), Pd(dppf)Cl$_2$ (347 mg, 0.48 mmol), potassium acetate (2.79 g, 28.5 mmol) and 1,4-dioxane (40 mL) were added in a microwave tube, and the mixture was heated to react at 120° C. under microwave for 3 hours. After completion of the reaction, the mixture was cooled, extracted with ethyl acetate (3*20 mL), and washed once with saturated sodium chloride. The organic layer was concentrated in vacuo to remove the solvent, and the residue was separated by a silica gel column (petroleum ether:ethyl acetate=100:1) to give a product (white solid, 2.8 g), with a yield of 95.2%. $^1$H NMR (400 MHz, CDCl$_3$) δ 8.04 (s, 1H), 7.90 (d, J=8.0 Hz, 1H), 7.51 (d, J=8.0 Hz, 1H), 6.70 (s, 1H), 2.57 (t, J=7.1 Hz, 2H), 2.52 (t, J=7.1 Hz, 2H), 1.83-1.74 (m, 2H), 1.74-1.66 (m, 2H), 1.34 (s, 12H).

Step 3: Synthesis of 2',6'-dichloro-4-(cyclopentylidenemethyl)-4'-nitro-[1,1'-biphenyl]-3-carbonitrile 2-(Cyclopentylidenemethyl)-5-(4,4,5,5-tetramethyl-1,3,2-dioxaborolan-2-yl)benzonitrile (2.8 g, 9.1 mmol), 1,3-dichloro-2-iodo-5-nitrobenzene (3.46 g, 10.9 mmol), sodium carbonate (2.89 g, 27.3 mmol), PdCl$_2$(dtbpf) (297 mg, 0.46 mmol) and 2 wt % Tween 20 in water (30 mL) were added in a 100 mL single-neck flask, and the mixture was heated to react at 80° C. for 30 minutes. After completion of the reaction, the mixture was extracted with ethyl acetate (5*30 mL). The organic layers were combined, washed with saturated sodium chloride, and concentrated in vacuo to remove the solvent. The residue was separated by a silica gel column (petroleum ether:ethyl acetate=10:1) to give a product (white solid, 1.1 g), with a yield of 76.5%. $^1$H NMR (400 MHz, CDCl$_3$) δ 8.30 (s, 2H), 7.68 (d, J=8.3 Hz, 1H), 7.52 (d, J=1.4 Hz, 1H), 7.41 (d, J=8.3 Hz, 1H), 6.77 (s, 1H), 2.61 (dd, J=16.4, 8.0 Hz, 5H), 1.90-1.79 (m, 2H), 1.78-1.67 (m, 2H).

Step 4: Synthesis of 4'-amino-2',6'-dichloro-4-(cyclopentylmethyl)-[1,1'-biphenyl]-3-carbo nitrile 2',6'-Dichloro-4-(cyclopentylidenemethyl)-4'-nitro-[1,1'-biphenyl]-3-carbonitrile (400 mg, 1.07 mmol), platinum dioxide (100 mg) and methanol (10 mL) were added in a 50 mL single-neck flask, and the mixture was reacted at room temperature for 30 minutes under hydrogen atmosphere, then additional platinum dioxide (50 mg) was added. The reaction was monitored by LC-MS, and was stopped immediately after completion. The mixture was filtered through Celite, and the filtrate was concentrated in vacuo and separated by a silica gel column (petroleum ether:ethyl acetate=50:1-10:1) to give a product (white solid, 170 mg), with a yield of 45.9%. MS (ESI) m/z: 345.1 (MH+).

Step 5: Synthesis of N-(2,6-dichloro-3'-cyano-4'-(cyclopentylmethyl)-[1,1'-biphenyl]-4-yl)-2-(4-(ethylsulfonyl)phenyl)acetamide 4'-Amino-2',6'-dichloro-4-(cyclopentylmethyl)-[1,1'-biphenyl]-3-carbonitrile (70 mg, 0.2 mmol), 2-(4-(ethylsulfonyl)phenyl)acetic acid (56 mg, 0.24 mmol), HATU (91 mg, 0.24 mmol), N,N-diisopropylethylamine (77 mg, 0.6 mmol) and dichloromethane (5 mL) were added in a 25 mL single-neck flask, and the mixture was reacted at room temperature for 1 hour. After the materials had all reacted when being determined by TLC, dichloromethane (20 mL) was added, and the mixture was washed with saturated ammonium chloride (30 mL). The organic layer was concentrated in vacuo to remove the solvent, and the resulting crude product was separated by a silica gel column (petroleum ether:ethyl acetate=2:1-1:1) to give a product (white solid, 90 mg), with a yield of 79.6%. $^1$H NMR (400 MHz, CD$_3$OD) δ 7.88 (d, J=8.3 Hz, 2H), 7.78 (s, 2H), 7.62 (d, J=8.3 Hz, 2H), 7.53 (d, J=1.3 Hz, 1H), 7.50 (d, J=8.1 Hz, 1H), 7.43 (dd, J=8.1, 1.6 Hz, 1H), 3.85 (s, 2H), 3.19 (q, J=7.4 Hz, 2H), 2.89 (d, J=7.5 Hz, 2H), 2.22 (dq, J=15.2, 7.5 Hz, 1H), 1.80-1.64 (m, 4H), 1.63-1.51 (m, 2H), 1.35-1.28 (m, 2H), 1.21 (t, J=11.7, 4.1 Hz, 3H). MS (ESI) m/z: 552.8 (M−1).

Example 46

N-(2,6-Dichloro-3'-cyano-4'-(cyclopentylidenemethyl)-[1,1'-biphenyl]-4-yl)-2-(4-(ethylsulfonyl)phenyl)acetamide

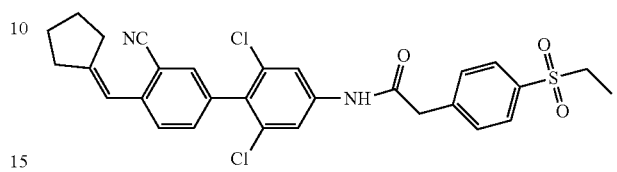

Step 1: Synthesis of 4'-amino-2',6'-dichloro-4-(cyclopentylidenemethyl)-[1,1'-biphenyl]-3-carbonitrile 2',6'-Dichloro-4-(cyclopentylidenemethyl)-4'-nitro-[1,1'-biphenyl]-3-carbonitrile (200 mg, 0.56 mmol), tin(II) chloride dihydrate (381 mg, 1.68 mmol), ethanol (5 mL) and concentrated hydrochloric acid (0.20 mL) were added in a 100 mL single-neck flask, and the mixture was heated to react at 60° C. for 1 hour. After the materials had all reacted when being determined by TLC, the mixture was concentrated in vacuo to remove ethanol, then the mixture was adjusted to pH 9 with saturated sodium carbonate solution and extracted with ethyl acetate (3*20 mL). The organic layers were combined, washed once with saturated sodium chloride, dried over anhydrous sodium sulfate, filtered, and concentrated in vacuo to remove the solvent to give a product (white solid, 120 mg), with a yield of 87.0%.

Step 2: Synthesis of N-(2,6-dichloro-3'-cyano-4'-(cyclopentylidenemethyl)-[1,1'-biphenyl]-4-yl)-2-(4-(ethylsulfonyl)phenyl)acetamide 4'-Amino-2',6'-dichloro-4-(cyclopentylidenemethyl)-[1,1'-biphenyl]-3-carbonitrile (120 mg, 0.35 mmol), 2-(4-(ethylsulfonyl)phenyl)acetic acid (95 mg, 0.42 mmol), HATU (160 mg, 0.42 mmol), N,N-diisopropylethylamine (135 mg, 1.05 mmol) and dichloromethane (5 mL) were added in a 25 mL single-neck flask, and the mixture was reacted at room temperature for 3 hours. After the materials had all reacted when being determined by TLC, dichloromethane (20 mL) was added, and the mixture was washed with saturated ammonium chloride (30 mL). The organic layer was concentrated to afford a crude product, which was separated by a silica gel column (petroleum ether:ethyl acetate=1:1-1:2) to give a product (white solid, 114 mg), with a yield of 59.1%. $^1$H NMR (400 MHz, CDCl$_3$) δ 8.00 (s, 1H), 7.86 (d, J=8.2 Hz, 2H), 7.69 (s, 2H), 7.61 (d, J=8.3 Hz, 1H), 7.53 (d, J=8.2 Hz, 2H), 7.49 (d, J=1.5 Hz, 1H), 7.39 (dd, J=8.2, 1.5 Hz, 1H), 6.74 (s, 1H), 3.83 (s, 2H), 3.13 (q, J=7.4 Hz, 2H), 2.58 (q, J=8.0 Hz, 4H), 1.86-1.77 (m, 2H), 1.76-1.71 (m, 3H), 1.30 (t, J=7.4 Hz, 3H). MS (ESI) m/z: 550.7 (M−1).

Example 47

(2,6-Dichloro-3'-cyano-N-(4-(ethylsulfonyl)benzyl)-4'-isobutyl-[1,1'-biphenyl]-4-carboxamide

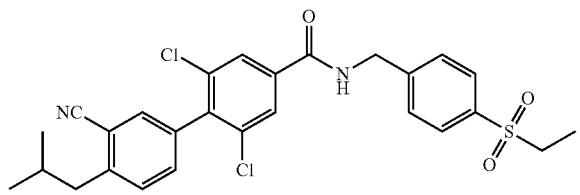 [SMILES: CCS(=O)(=O)c1ccc(CNC(=O)c2cc(Cl)c(-c3ccc(CC(C)C)c(C#N)c3)c(Cl)c2)cc1]

Intermediate 47A: 2,6-dichloro-3'-cyano-4'-isobutyl-[1,1'-biphenyl]-4-carboxylic acid Step 1: Synthesis of 3,5-dichloro-4-iodobenzonitrile 4-Amino-3,5-dichlorobenzonitrile (3 g, 16 mmol), acetic acid (20 mL) and concentrated sulfuric acid (8 mL) were added in a 100 mL single-neck flask A. The mixture was stirred in an ice bath for 10 minutes, then a solution of sodium nitrite (1.55 g, 22 mmol) in $H_2O$ (5 mL) was added dropwise into flask A. After the addition, the reaction was continued in the ice bath for 30 minutes. To a 250 mL single-neck flask B were added ice, urea (0.5 g) and potassium iodide (2.66 g, 16 mmol). The solution in flask A was added into flask B slowly. After the addition, the mixture was reacted at room temperature for 3 hours. After completion of the reaction, the mixture was filtered and the filtrate was discarded. While the resulting solid was dissolved in ethyl acetate, and the solution was washed once with saturated sodium chloride, dried over anhydrous sodium sulfate, and concentrated in vacuo to remove the solvent to give a product (yellow solid, 4.5 g), with a yield of 95.7%.

Step 2: Synthesis of 3,5-dichloro-4-iodobenzoic acid 3,5-Dichloro-4-iodobenzonitrile (1.5 g, 5 mmol), potassium hydroxide (846 mg, 15 mmol), and ethanol/$H_2O$ (15 mL/3 mL) were added in a 25 mL single-neck flask, and the mixture was reacted at 80° C. overnight. After completion of the reaction, the mixture was concentrated in vacuo to remove ethanol, then water (5 mL) was added. The mixture was adjusted to pH 2-3 with 2N hydrochloric acid, and a large amount of white solid precipitated, which was filtered and dried in vacuo to afford a product (1.5 g), with a yield of 93.8%. $^1$H NMR (400 MHz, DMSO) δ 13.71 (s, 1H), 7.86 (t, J=7.4 Hz, 2H).

Step 3: Synthesis of methyl 3,5-dichloro-4-iodobenzoate 3,5-Dichloro-4-iodobenzoic acid (1.5 g, 4.7 mmol), methanol (10 mL) and thionyl chloride (0.5 mL) were added in a 25 mL single-neck flask, and the mixture was heated to react at 60° C. overnight. After completion of the reaction, the mixture was concentrated in vacuo to remove methanol, and water (20 mL) was added. The mixture was extracted with ethyl acetate (3*30 mL), dried over anhydrous sodium sulfate, and concentrated in vacuo to remove the solvent to give a product (orange solid, 1.53 g), with a yield of 98.1%. $^1$H NMR (400 MHz, CDCl$_3$) δ 7.94 (s, 2H), 3.92 (s, 3H).

Step 4: Synthesis of methyl 2,6-dichloro-3'-cyano-4'-(2-methylprop-1-en-1-yl)-[1,1'-biphenyl]-4-carboxylate 2-(2-Methylprop-1-en-1-yl)-5-(4,4,5,5-tetramethyl-1,3,2-dioxaborolan-2-yl)benzonitrile (1.53 g, 5.4 mmol, example 1, step 4), methyl 3,5-dichloro-4-iodobenzoate (1.5 g, 4.5 mmol), potassium carbonate (1.84 g, 13.5 mmol), PdCl$_2$(dtbpf) (147 mg, 0.23 mmol) and 2 wt % Tween 20/$H_2O$ (20 mL) were added in a 100 mL single-neck flask, and the mixture was heated to react at 80° C. for 1 hour under microwave. After completion of the reaction, the mixture was extracted with ethyl acetate (5*20 mL). The organic layers were combined, washed with saturated sodium chloride, and concentrated in vacuo to remove the solvent. The residue was separated by a silica gel column (petroleum ether:ethyl acetate=20:1-5:1) to give a product (white solid, 1 g), with a yield of 60.2%. $^1$H NMR (400 MHz, CDCl$_3$) δ 8.07 (s, 2H), 7.55 (s, 1H), 7.48 (d, J=8.1 Hz, 1H), 7.42 (d, J=7.9 Hz, 1H), 6.49 (s, 1H), 3.97 (s, 3H), 2.01 (s, 3H), 1.90 (s, 3H).

Step 5: Synthesis of methyl 2,6-dichloro-3'-cyano-4'-isobutyl-[1,1'-biphenyl]-4-carboxylate Methyl 2,6-dichloro-3'-cyano-4'-(2-methylprop-1-en-1-yl)-[1,1'-biphenyl]-4-carboxylate (500 mg), methanol (5 mL) and platinum dioxide (15 mg) were added in a 25 mL single-neck flask with a hydrogen balloon equipped, and the mixture was reacted at room temperature for 2 hours under hydrogen atmosphere. The mixture was filtered through Celite, and the crude product was separated by a silica gel column (petroleum ether:ethyl acetate=100:1) to give a product (white solid, 340 mg), with a yield of 37.8%. $^1$H NMR (400 MHz, CDCl$_3$) δ 8.08 (d, J=1.1 Hz, 2H), 7.53 (s, 1H), 7.40 (s, 3H), 3.97 (s, 3H), 2.80 (d, J=7.1 Hz, 2H), 2.08 (td, J=13.3, 6.8 Hz, 1H), 1.01 (d, J=6.6 Hz, 6H).

Step 6: Synthesis of 2,6-dichloro-3'-cyano-4'-isobutyl-[1,1'-biphenyl]-4-carboxylic acid Methyl 2,6-dichloro-3'-cyano-4'-isobutyl-[1,1'-biphenyl]-4-carboxylate (190 mg, 0.52 mmol), lithium hydroxide monohydrate (66 mg, 1.56 mmol) and ethanol/$H_2O$ (2 mL/0.5 mL) were added in a 25 mL single-neck flask, and the mixture was heated to react at 50° C. for 20 minutes. After completion of the reaction, the mixture was concentrated in vacuo to remove ethanol, then water (5 mL) was added. The mixture was adjusted to acidic pH with 2N hydrochloric acid, and extracted with ethyl acetate (3*10 mL). The organic layers were combined, dried over anhydrous sodium sulfate, and concentrated in vacuo to remove the solvent to give a product (white solid, 165 mg), with a yield of 90.6%. $^1$H NMR (400 MHz, DMSO) δ 8.02 (s, 2H), 7.84 (s, 1H), 7.60 (s, 2H), 2.75 (d, J=7.3 Hz, 2H), 1.99 (t, J=6.7 Hz, 1H), 0.94 (d, J=6.6 Hz, 6H). MS (ESI) m/z: 348.0 (M+1).

Synthesis of Intermediate 47B: (4-(ethylsulfonyl)phenyl)methanamine

Step 1: 4-(Ethylsulfonyl)benzonitrile

4-Cyanobenzenesulfonyl chloride (1 g, 4.97 mmol), water (15 mL), sodium bicarbonate (835 mg, 9.94 mmol) and sodium sulfite (689 mg, 5.47 mmol) were added to a 100 mL single-neck flask, and the mixture was stirred at 70° C. for 4 hours. The mixture was concentrated in vacuo to remove the solvent, and the residue was dissolved in N,N-dimethylformamide (20 mL), then iodoethane (1.2 mL) was added, and the mixture was stirred at 70° C. for another 4 hours. The mixture was cooled to room temperature, then water (30 mL) was added, and the mixture was extracted with ethyl acetate (30 mL*3). The organic layers were combined, washed with saturated sodium chloride, dried over anhydrous sodium sulfate, and filtered. The filtrate was concentrated in vacuo to remove the solvent to afford a crude product, which was separated by a silica gel column (ethyl acetate:petroleum ether=1:4-1:2) to give a product (yellow solid, 630 mg), with a yield of 65.0%. $^1$H NMR (400 MHz, CDCl$_3$) δ 8.04 (d, J=8.5 Hz, 2H), 7.89 (d, J=8.6 Hz, 2H), 3.16 (q, J=7.4 Hz, 2H), 1.30 (t, J=7.4 Hz, 3H).

Step 2: (4-(Ethyl sulfonyl)phenyl)methanamine 4-(Ethylsulfonyl)benzonitrile (630 mg, 3.23 mmol), methanol (10 mL) and Pd/C (100 mg, 10%) were added in a 25 mL single-neck flask, and the mixture was stirred at room temperature for 1 hour. The mixture was filtered through Celite, and concentrated in vacuo to remove the solvent to afford a product (white solid, 500 mg), with a yield of 77.9%. $^1$H NMR (400 MHz, CDCl$_3$) δ 7.86 (d, J=8.3 Hz, 2H), 7.53 (d, J=8.2 Hz, 2H), 3.99 (s, 2H), 3.10 (d, J=7.4 Hz, 2H), 1.27 (t, J=7.4 Hz, 3H).

Synthesis of 2,6-dichloro-3'-cyano-N-(4-(ethylsulfonyl)benzyl)-4'-isobutyl-[1,1'-biphenyl]-4-carboxamide (4-(Ethylsulfonyl)phenyl)methanamine (27 mg, 0.14 mmol), 2,6-dichloro-3'-cyano-4'-isobutyl-[1,1'-biphenyl]-4-carboxylic acid (40 mg, 0.11 mmol), HATU (53 mg, 0.14 mmol), N,N-diisopropylethylamine (43 mg, 0.33 mmol) and dichloromethane (3 mL) were added in a 25 mL single-neck flask, and the mixture was reacted at room temperature for 3 hours. After the materials had all reacted when being determined by TLC, dichloromethane (20 mL) was added, and the mixture was washed with saturated ammonium chloride (30 mL). The organic layer was concentrated in vacuo to afford a crude product, which was separated by a silica gel column (petroleum ether:ethyl acetate=1:1-1:2) to give a product (white solid, 60 mg), with a yield of 98.7%. $^1$H NMR (400 MHz, CDCl$_3$) δ 7.97 (s, 2H), 7.69 (d, J=5.8 Hz, 1H), 7.66 (d, J=8.0 Hz, 2H), 7.50 (s, 1H), 7.43 (d, J=8.0 Hz, 2H), 7.39 (s, 2H), 4.72 (d, J=5.7 Hz, 2H), 3.07 (q, J=7.4 Hz, 2H), 2.79 (s, 2H), 2.13-2.00 (m, 1H), 1.23 (t, J=7.4 Hz, 3H), 0.99 (d, J=6.6 Hz, 6H). MS (ESI) m/z: 529.0 (M+1).

Example 48

2,6-Dichloro-3'-cyano-4'-isobutyl-N-(4-(methylsulfonyl)benzyl)-[1,1'-biphenyl]-4-carboxamide

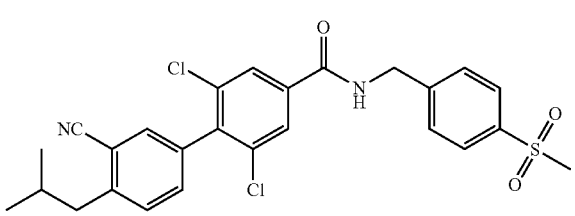 [SMILES: CC(C)Cc1ccc(-c2c(Cl)cc(C(=O)NCc3ccc(S(C)(=O)=O)cc3)cc2Cl)cc1C#N]

(4-(Methyl sulfonyl)phenyl)methanamine hydrochloride (31 mg, 0.14 mmol), 2,6-dichloro-3'-cyano-4'-isobutyl-[1, 1'-biphenyl]-4-carboxylic acid (40 mg, 0.11 mmol), HATU (53 mg, 0.14 mmol), N,N-diisopropylethylamine (43 mg, 0.33 mmol) and dichloromethane (3 mL) were added in a 25 mL single-neck flask, and the mixture was reacted at room temperature for 3 hours. After the materials had all reacted when being determined by TLC, dichloromethane (20 mL) was added, and the mixture was washed with saturated ammonium chloride (30 mL). The organic layer was concentrated in vacuo to afford a crude product, which was separated by a silica gel column (petroleum ether:ethyl acetate=1:1-1:2) to give a product (white solid, 50 mg), with a yield of 87.7%. $^1$H NMR (400 MHz, CDCl$_3$) δ 7.89 (d, J=8.7 Hz, 4H), 7.55 (s, 1H), 7.52 (d, J=6.6 Hz, 2H), 7.40 (s, 2H), 6.81 (s, 1H), 4.76 (d, J=5.5 Hz, 2H), 3.05 (s, 3H), 2.79 (d, J=7.3 Hz, 2H), 2.06 (td, J=13.2, 6.3 Hz, 1H), 1.00 (d, J=6.6 Hz, 6H). MS (ESI) m/z: 515.0 (M+1).

Example 49

2,6-Dichloro-3'-cyano-N-((5-(ethylsulfonyl)pyridin-2-yl)methyl)-4'-isobutyl-[1,1'-biphenyl]-4-carboxamide

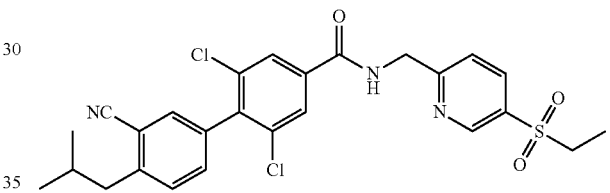

Intermediate 49a:
(5-(Ethylsulfonyl)pyridin-2-yl)methanamine

Step 1: Synthesis of 5-(ethylthio)picolinonitrile

5-Bromo-2-picolinonitrile (940 mg, 5.14 mmol), ethyl mercaptan (505 mg, 6.01 mmol), potassium carbonate (981 mg, 7.11 mmol) and NMP (10 mL) were added in a 50 mL single-neck flask, and the mixture was stirred at room temperature overnight. Water (20 mL) was added, then the mixture was extracted with ethyl acetate (3*30 mL). The organic layers were concentrated in vacuo to afford a product 5-(ethylthio)picolinonitrile (900 mg), with a yield of 100%. MS (ESI) m/z: 165.1 (MH+).

Step 2: Synthesis of 5-(ethylsulfonyl)-2-picolinonitrile 5-(Ethylthio)picolinonitrile (800 mg, 4.88 mmol) and dichloromethane (20 mL) were added in a 25 mL single-neck flask and stirred in an ice bath for 10 minutes. mCPBA (1.84 g, 10.7 mmol) was added in portions into the reaction mixture, and then the mixture was reacted at room temperature overnight. The mixture was washed with 2N sodium carbonate aqueous solution, and the organic layer was concentrated in vacuo to remove the solvent. The residue was separated by a silica gel column (petroleum ether:ethyl acetate=2:1-1:1) to give a product (900 mg), with a yield of 90.0%. $^1$H NMR (400 MHz, CDCl$_3$) δ 9.18 (d, J=1.2 Hz, 1H), 8.37 (dd, J=8.0, 1.8 Hz, 1H), 7.93 (d, J=8.0 Hz, 1H), 3.21 (q, J=7.4 Hz, 2H), 1.34 (t, J=7.4 Hz, 3H). MS (ESI) m/z: 197.1 (M+1).

Step 3: Synthesis of (5-(ethylsulfonyl)pyridin-2-yl)methanamine 5-(Ethylsulfonyl)-2-picolinonitrile (200 mg, 1 mmol), methanol (10 mL) and Pd/C (100 mg, 10%) were added in a 25 mL single-neck flask, and the reaction mixture was stirred at room temperature for 30 minutes under hydrogen atmosphere. The mixture was filtered through Celite, and the filtrate was concentrated in vacuo to afford a product (white solid, 110 mg), with a yield of 53.9%. MS (ESI) m/z: 201.1 (M+1).

Synthesis of 2,6-dichloro-3'-cyano-N-((5-(ethylsulfonyl)pyridin-2-yl)methyl)-4'-isobutyl-[1'-biphenyl]-4-carboxamide (5-(Ethylsulfonyl)pyridin-2-yl)methanamine (28 mg, 0.14 mmol), 2,6-dichloro-3'-cyano-4'-isobutyl-[1,1'-biphenyl]-4-carboxylic acid (40 mg, 0.11 mmol), HATU (53 mg, 0.14 mmol), N,N-diisopropylethylamine (43 mg, 0.33 mmol) and dichloromethane (3 mL) were added in a 25 mL single-neck flask, and the mixture was reacted at room temperature for 3 hours. After the materials had all reacted when being determined by TLC, dichloromethane (20 mL) was added, and the mixture was washed with saturated ammonium chloride (30 mL). The organic layer was concentrated in vacuo to afford a crude product, which was separated by a silica gel column (petroleum ether:ethyl acetate=1:1) to give a product (white solid, 55 mg), with a yield of 90.2%. $^1$H NMR (400 MHz, CDCl$_3$) δ 9.05 (s, 1H), 8.18 (d, J=8.1 Hz, 1H), 7.93 (s, 2H), 7.74 (s, 1H), 7.56 (d, J=8.2 Hz, 1H), 7.53 (s, 1H), 7.41 (s, 2H), 4.89 (d, J=4.8 Hz, 2H), 3.18 (q, J=7.3 Hz, 2H), 2.79 (s, 2H), 2.07 (dt, J=13.5, 6.7 Hz, 1H), 1.33 (t, J=7.3 Hz, 3H), 1.01 (d, J=6.5 Hz, 6H). MS (ESI) m/z: 530.0 (M+1).

Example 50

2,6-Dichloro-3'-cyano-4'-isobutyl-N-((5-(methylsulfonyl)pyridin-2-yl)methyl)-[1,1'-biphenyl]-4-carboxamide

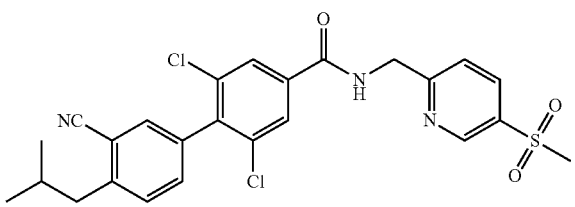 [SMILES: CC(C)Cc1ccc(-c2c(Cl)cc(C(=O)NCc3ccc(S(C)(=O)=O)cn3)cc2Cl)cc1C#N]

(5-(Methylsulfonyl)-pyridin-2-yl)methylamine (26 mg, 0.14 mmol), 2,6-dichloro-3'-cyano-4'-isobutyl-[1,1'-biphenyl]-4-carboxylic acid (40 mg, 0.11 mmol), HATU (53 mg, 0.14 mmol), N,N-diisopropylethylamine (43 mg, 0.33 mmol) and dichloromethane (3 mL) were added in a 25 mL single-neck flask, and the mixture was reacted at room temperature for 3 hours. After the materials had all reacted when being determined by TLC, dichloromethane (20 mL) was added, and the mixture was washed with saturated ammonium chloride (30 mL). The organic layer was concentrated in vacuo to afford a crude product, which was separated by a silica gel column (petroleum ether:ethyl acetate=1:1-1:2) to give a product (white solid, 44 mg), with a yield of 74.6%. $^1$H NMR (400 MHz, CDCl$_3$) δ 9.05 (s, 1H), 8.19 (d, J=8.2 Hz, 1H), 7.96-7.89 (m, 2H), 7.80 (s, 1H), 7.55 (d, J=8.2 Hz, 1H), 7.50 (s, 1H), 7.39 (s, 2H), 4.85 (d, J=4.7 Hz, 2H), 3.15-3.06 (m, 3H), 2.77 (d, J=7.1 Hz, 2H), 2.12-1.98 (m, 1H), 0.98 (d, J=6.5 Hz, 6H). MS (ESI) m/z: 516.0 (M+1).

Example 51

2,6-Dichloro-3'-cyano-4'-((dimethylamino)methyl)-N-(4-(ethylsulfonyl)benzyl)-[1,1'-biphenyl]-4-carboxamide

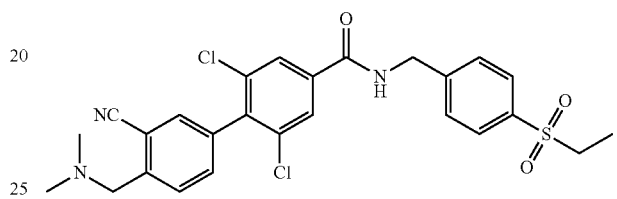

Step 1: Synthesis of 5-bromo-2-(bromomethyl)benzonitrile

5-Bromo-2-methylbenzonitrile (10 g, 5.1 mmol), NBS (9.99 g, 5.6 mmol), BPO (0.63 g, 0.26 mmol) and carbon tetrachloride (100 mL) were added in a 250 mL single-neck flask, and the mixture was heated to react at 90° C. overnight. After completion of the reaction, the mixture was cooled to room temperature and filtered. The filtrate was concentrated in vacuo to remove the solvent, and the residue was separated by a silica gel column (petroleum ether:ethyl acetate=30:1) to give a product (white solid, 8.5 g), with a yield of 60.7%.

Step 2: Synthesis of 5-bromo-2-((dimethylamino)methyl)benzonitrile

5-Bromo-2-(bromomethyl)benzonitrile (2 g, 7.3 mmol), a solution of dimethylamine in tetrahydrofuran (11 mL, 21.9 mmol), potassium carbonate (2.97 g, 21.9 mmol) and acetonitrile (20 mL) were added in a 25 mL single-neck flask, and the mixture was reacted at 90° C. overnight. After completion of the reaction, water (20 mL) was added, and the mixture was extracted with ethyl acetate (3*10 mL). The organic layers were combined, washed with saturated sodium chloride, dried over anhydrous sodium sulfate, and concentrated in vacuo to remove the solvent. The residue was separated by a silica gel column (petroleum ether:ethyl acetate=10:1) to give a product (yellow oil, 1.5 g), with a yield of 88.3%. $^1$H NMR (400 MHz, CDCl$_3$) δ 7.77 (s, 1H), 7.69 (d, J=8.4 Hz, 1H), 7.45 (d, J=8.3 Hz, 1H), 3.59 (s, 2H), 2.29 (s, 7H).

Step 3: Synthesis of 2-((dimethylamino)methyl)-5-(4,4,5,5-tetramethyl-1,3,2-dioxaborolan-2-yl)benzonitrile 5-Bromo-2-((dimethylamino)methyl)benzonitrile (1.2 g, 5 mmol), bis(pinacolato)diboron (1.7 g, 7.5 mmol), potassium acetate (1.48 g, 15 mmol), PdCl$_2$(dppf) (182 mg, 0.25 mmol) and 1,4-dioxane (10 mL) were added in a microwave tube, and the mixture was reacted at 120° C. under microwave for 1 hour. After completion of the reaction, water (20 mL) was added, and the mixture was extracted with ethyl acetate (3*20 mL). The organic layer was concentrated in vacuo, and the residue was separated by a silica gel column (petroleum ether:ethyl acetate=5:1-1:1) to give a product (yellow oil, 720 mg), with a yield of 55.6%. $^1$H NMR (400 MHz, CDCl$_3$) δ 8.08 (s, 1H), 7.97 (d, J=7.7 Hz, 1H), 7.57 (d, J=7.7 Hz, 1H), 3.66 (s, 2H), 2.29 (s, 6H), 1.35 (s, 12H).

Step 4: Synthesis of methyl 2,6-dichloro-3'-cyano-4'-((dimethylamino)methyl)-[1,1'-biphenyl]-4-carboxylate 2-((Dimethylamino)methyl)-5-(4,4,5,5-tetramethyl-1,3,2-dioxaborolan-2-yl)benzonitrile (367 mg, 1.28 mmol), methyl 3,5-dichloro-4-iodobenzoate (340 mg, 1.07 mmol), potassium carbonate (437 mg, 3.21 mmol)), PdCl$_2$(dtbpf) (33 mg, 0.05 mmol) and 2 wt % Tween 20/H$_2$O (10 mL) were added in a 50 mL single-neck flask, and the mixture was heated to react at 80° C. for 1 hour under microwave. After completion of the reaction, the mixture was extracted with ethyl acetate (3*20 mL). The organic layers were combined, washed with saturated sodium chloride, and concentrated in vacuo to remove the solvent. The residue was separated by a silica gel column (petroleum ether:ethyl acetate=10:1) to give a product (yellow oil, 150 mg), with a yield of 40.3%. $^1$H NMR (400 MHz, CDCl$_3$) δ 8.08 (s, 2H), 7.71 (d, J=7.9 Hz, 1H), 7.56 (s, 1H), 7.47 (d, J=8.0 Hz, 1H), 3.97 (s, 3H), 3.73 (s, 2H), 2.37 (s, 6H).

Step 5: Synthesis of 2,6-dichloro-3'-cyano-4'-((dimethylamino)methyl)-[1,1'-biphenyl]-4-carboxylic acid Methyl 2,6-dichloro-3'-cyano-4'-((dimethylamino)methyl)-[1,1'-biphenyl]-4-carboxylate (150 mg, 0.41 mmol), lithium hydroxide monohydrate (52 mg, 1.23 mmol) and ethanol/H$_2$O (5 mL/1 mL) were added in a 25 mL single-neck flask, and the mixture was heated to react at 50° C. for 20 minutes. After completion of the reaction according to TLC, the mixture was concentrated to remove ethanol, and pH of the mixture was adjusted by 1N hydrochloric acid. A large amount of yellow solid was precipitated, filtered, and dried in vacuo to give a product (yellow solid, 120 mg), with a yield of 83.3%. $^1$H NMR (400 MHz, DMSO) δ 7.95 (s, 2H), 7.83 (s, 1H), 7.69 (d, J=7.8 Hz, 1H), 7.62 (d, J=7.5 Hz, 1H), 3.63 (s, 2H), 2.23 (s, 6H).

Step 6: 2,6-Dichloro-3'-cyano-4'-((dimethylamino)methyl)-N-(4-(ethylsulfonyl)benzyl)-[1,1'-biphenyl]-4-carboxamide 2,6-Dichloro-3'-cyano-4'-((dimethylamino)methyl)-[1,1'-biphenyl]-4-carboxylic acid (55 mg, 0.16 mmol), (4-(ethylsulfonyl)phenyl)methanamine (38 mg, 0.19 mmol), HATU (72 mg, 0.19 mmol), N,N-diisopropylethylamine (62 mg, 0.48 mmol) and dichloromethane (5 mL) were added in a 25 mL single-neck flask, and the mixture was reacted at room temperature for 3 hours. After the materials had all reacted when being determined by TLC, dichloromethane (5 mL) was added, and the mixture was washed with saturated ammonium chloride (30 mL). The organic layer was concentrated in vacuo to afford a crude product, which was separated by a silica gel column (petroleum ether:ethyl acetate=1:1-1:2) to give a product (white solid, 35 mg), with a yield of 83.5%. $^1$H NMR (400 MHz, CDCl$_3$) δ 7.98 (s, 2H), 7.73-7.63 (m, 3H), 7.55 (s, 2H), 7.47 (d, J=7.8 Hz, 1H), 7.43 (d, J=8.0 Hz, 2H), 4.74 (d, J=5.7 Hz, 2H), 3.72 (s, 2H), 3.08 (q, J=7.3 Hz, 2H), 2.36 (s, 6H), 1.25 (t, J=7.4 Hz, 3H). MS (ESI) m/z: 530.0 (M+1).

Example 52

2,6-Dichloro-3'-cyano-4'-((dimethylamino)methyl)-N-(4-(methylsulfonyl)benzyl)-[1,1'-biphenyl]-4-carboxamide

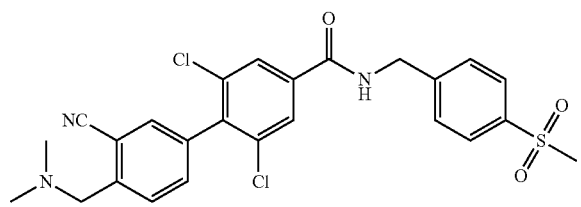

2,6-Dichloro-3'-cyano-4'-((dimethylamino)methyl)-[1,1'-biphenyl]-4-carboxylic acid (55 mg, 0.16 mmol), (4-(methylsulfonyl)phenyl)methanamine (43 mg, 0.19 mmol), HATU (72 mg, 0.19 mmol), N,N-diisopropylethylamine (62 mg, 0.48 mmol) and dichloromethane (3 mL) were added in a 25 mL single-neck flask, and the mixture was reacted at room temperature for 3 hours. After the materials had all reacted when being determined by TLC, dichloromethane (5 mL) was added, and the mixture was washed with saturated ammonium chloride (10 mL). The organic layer was concentrated in vacuo to remove the solvent to afford a crude product, which was separated by a silica gel column (petroleum ether:ethyl acetate=1:1-1:2) to give a product (white solid, 35 mg), with a yield of 43.2%. $^1$H NMR (400 MHz, DMSO) δ 9.46 (s, 1H), 8.08 (s, 2H), 7.96-7.84 (m, 3H), 7.69 (d, J=8.1 Hz, 1H), 7.66-7.53 (m, 3H), 4.58 (s, 2H), 3.61 (s, 2H), 3.18 (s, 3H), 2.21 (s, 6H). MS (ESI) m/z: 516.0 (M+1).

Example 53

1-(2,6-Dichloro-3'-cyano-4'-isobutyl-[1,1'-biphenyl]-4-yl)-3-(4-(ethylsulfonyl)benzyl)urea

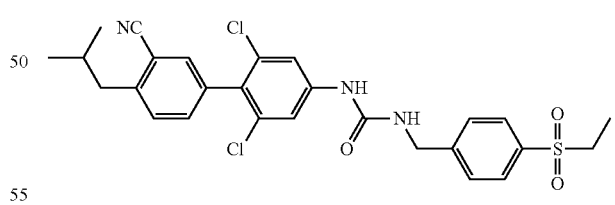

4'-Amino-2',6'-dichloro-4-isobutyl-[1,1'-biphenyl]-3-carbonitrile (50 mg, 0.16 mmol), dichloromethane (2 mL) and DIEA (62 mg, 0.48 mmol) were added in a 25 mL single-neck flask and stirred in an ice bath for 5 minutes. Then triphosgene (19 mg, 0.064 mmol) was added and the mixture was stirred in the ice bath for 30 minutes. And then (4-(ethylsulfonyl)phenyl)methanamine (37 mg, 0.19 mmol) was added, and the mixture was stirred at room temperature for 30 minutes. Water (10 mL) was added, and the mixture was extracted with dichloromethane (3*10 mL). The organic layers were combined, washed with saturated sodium chloride (10 mL), dried over anhydrous sodium sulfate, and filtered. The filtrate was concentrated in vacuo to obtain a crude product, which was separated by a silica gel column (petroleum ether:ethyl acetate=1:1-1:2) to give a product (white solid, 82 mg), with a yield of 96.4%. ¹H NMR (400 MHz, CDCl₃) δ 7.85 (s, 1H), 7.69 (d, J=7.6 Hz, 2H), 7.51 (s, 2H), 7.45 (d, J=13.7 Hz, 1H), 7.39 (d, J=7.7 Hz, 2H), 7.35 (s, 2H), 6.23 (s, 1H), 4.48 (d, J=4.8 Hz, 2H), 3.14 (q, J=7.0 Hz, 2H), 2.76 (d, J=6.9 Hz, 2H), 2.01 (m, 1H), 1.28 (t, J=7.0 Hz, 3H), 0.99 (d, J=6.2 Hz, 6H). MS (ESI) m/z: 544.0 (M+1).

Example 54

1-(2,6-Dichloro-3'-cyano-4'-isobutyl-[1,1'-biphenyl]-4-yl)-3-(4-(methylsulfonyl)benzyl)urea

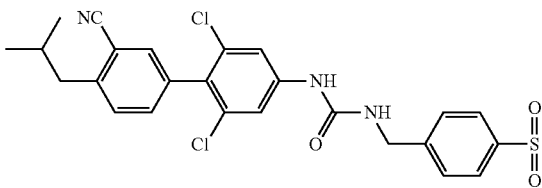

4'-Amino-2',6'-dichloro-4-isobutyl-[1,1'-biphenyl]-3-carbonitrile (50 mg, 0.16 mmol), dichloromethane (2 mL) and DIEA (62 mg, 0.48 mmol) were added in a 25 mL single-neck flask, and stirred in an ice bath for 5 minutes. Then triphosgene (19 mg, 0.064 mmol) was added, and the mixture was stirred in the ice bath for 10 minutes. And then (4-(methylsulfonyl)phenyl)methanamine (43 mg, 0.19 mmol) was added, and the mixture was stirred at room temperature for 30 minutes. Water (10 mL) was added, and the mixture was extracted with dichloromethane (3*10 mL) The organic layers were combined, washed with saturated sodium chloride (10 mL), dried over anhydrous sodium sulfate, and filtered. The filtrate was concentrated in vacuo to obtain a crude product, which was separated by a silica gel column (dichloromethane:methanol=100:1-50:1) to give a product (white solid, 43 mg), with a yield of 51.8%. ¹H NMR (400 MHz, CD₃OD) δ 7.89 (d, J=7.9 Hz, 2H), 7.57 (d, J=6.9 Hz, 4H), 7.51 (s, 1H), 7.48-7.38 (m, 2H), 4.49 (s, 2H), 3.08 (s, 3H), 2.74 (d, J=7.2 Hz, 2H), 2.11-1.90 (m, 1H), 0.97 (d, J=6.6 Hz, 6H). MS (ESI) m/z: 530.0 (M+1).

Example 55

1-(2,6-Dichloro-3'-cyano-4'-isobutyl-[1,1'-biphenyl]-4-yl)-3-((5-(ethylsulfonyl)pyridin-2-yl)methyl)urea

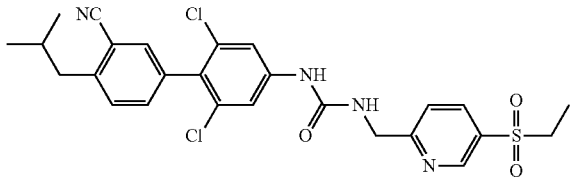 [SMILES: CCS(=O)(=O)c1ccc(CNC(=O)Nc2cc(Cl)c(-c3ccc(CC(C)C)c(C#N)c3)c(Cl)c2)nc1]

4'-Amino-2',6'-dichloro-4-isobutyl-[1,1'-biphenyl]-3-carbonitrile (50 mg, 0.16 mmol), dichloromethane (2 mL) and DIEA (62 mg, 0.48 mmol) were added in a 25 mL single-neck flask, and was stirred in an ice bath for 5 minutes. Then triphosgene (19 mg, 0.064 mmol) was added, and the mixture was stirred in the ice bath for 10 minutes. And then (5-(ethylsulfonyl)pyridin-2-yl)methanamine (43 mg, 0.19 mmol) was added, and the mixture was stirred at room temperature for 30 minutes. Water (10 mL) was added, and the mixture was extracted with dichloromethane (3*10 mL). The organic layers were combined, washed with saturated sodium chloride (10 mL), dried over anhydrous sodium sulfate, and filtered. The filtrate was concentrated in vacuo to obtain a crude product, which was separated by a silica gel column (dichloromethane:methanol=100:1) to give a product (white solid, 48 mg), with a yield of 56.5%. ¹H NMR (400 MHz, CD₃OD) δ 9.00 (s, 1H), 8.29 (d, J=8.1 Hz, 1H), 7.69 (d, J=8.0 Hz, 1H), 7.63 (s, 2H), 7.56 (s, 1H), 7.53-7.41 (m, 2H), 4.65 (s, 3H), 3.30 (q, J=7.4 Hz, 2H), 2.79 (d, J=7.3 Hz, 2H), 2.05 (m, 1H), 1.27 (t, J=7.4 Hz, 3H), 1.01 (d, J=6.5 Hz, 6H). MS (ESI) m/z: 544.8 (M+1).

Example 56

1-(2,6-Dichloro-3'-cyano-4'-isobutyl-[1,1'-biphenyl]-4-yl)-3-((5-(methylsulfonyl)pyridin-2-yl)methyl)urea

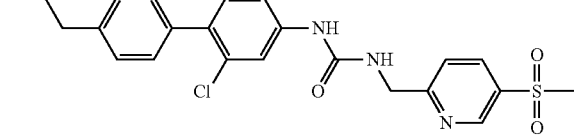

4'-Amino-2',6'-dichloro-4-isobutyl-[1,1'-biphenyl]-3-carbonitrile (50 mg, 0.16 mmol), dichloromethane (2 mL) and DIEA (62 mg, 0.48 mmol) were added in a 25 mL single-neck flask, and was stirred in an ice bath for 5 minutes. Then triphosgene (17 mg, 0.056 mmol) was added, and the mixture was stirred in the ice bath for 10 minutes. And then (5-(methylsulfonyl)pyridin-2-yl)methanamine (36 mg, 0.19 mmol) was added, and the mixture was stirred at room temperature for 30 minutes. Water (10 mL) was added, and the mixture was extracted with dichloromethane (3*10 mL). The organic layers were combined, washed with saturated sodium chloride (10 mL), dried over anhydrous sodium sulfate, and filtered. The filtrate was concentrated in vacuo to obtain a crude product, which was separated by a silica gel column (dichloromethane:methanol=100:1) to give a product (white solid, 45 mg), with a yield of 54.2%. ¹H NMR (400 MHz, CD₃OD) δ 9.00 (s, 1H), 8.28 (d, J=8.3 Hz, 1H), 7.64 (d, J=8.3 Hz, 1H), 7.57 (s, 2H), 7.51 (s, 1H), 7.42 (q, J=8.2 Hz, 2H), 4.61 (s, 2H), 3.18 (s, 3H), 2.75 (d, J=7.2 Hz, 2H), 2.11-1.94 (m, 1H), 0.97 (d, J=6.6 Hz, 6H). MS (ESI) m/z: 528.8 (M−1).

Example 57

2-(4-((3-(2,6-Dichloro-3'-cyano-4'-isobutyl-[1,1'-biphenyl]-4-yl)ureido)methyl)phenyl)acetic acid

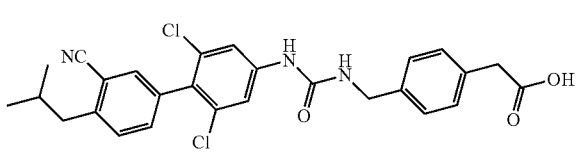 [SMILES: CC(C)Cc1ccc(-c2c(Cl)cc(NC(=O)NCc3ccc(CC(=O)O)cc3)cc2Cl)cc1C#N]

Step 1: Methyl 2-(4-(aminomethyl)phenyl)acetate

Methyl 2-(4-cyanophenyl)acetate (200 mg, 1.14 mmol), methanol (2 mL), Pd/C (a small amount) and 2 drops of concentrated hydrochloric acid were added in a 25 mL single-neck flask with a hydrogen balloon equipped, and the mixture was stirred at room temperature for 3 hours under hydrogen atmosphere. After completion of the reaction according to TLC, the mixture was filtered and the filtrate was concentrated to afford a product methyl 2-(4-(aminomethyl)phenyl)acetate (white solid, 178 mg), with a yield of 74.2%. $^1$H NMR (400 MHz, DMSO) δ 8.22 (s, 2H), 7.44 (d, J=8.1 Hz, 2H), 7.30 (d, J=8.1 Hz, 2H), 3.98 (s, 2H), 3.71 (s, 2H), 3.61 (s, 3H). MS (ESI) m/z: 180.1 (M+1).

Step 2: Methyl 2-(4-((3-(2,6-dichloro-3'-cyano-4'-isobutyl-[1,1'-biphenyl]-4-yl)ureido)methyl)phenyl)acetate 4'-Amino-2',6'-dichloro-4-isobutyl-[1,1'-biphenyl]-3-carbonitrile (50 mg, 0.16 mmol), dichloromethane (2 mL) and DIEA (62 mg, 0.48 mmol) were added in a 25 mL single-neck flask, and the mixture was stirred in an ice bath for 5 minutes. Then triphosgene (19 mg, 0.064 mmol) was added, and the mixture was stirred in the ice bath for 10 minutes. And then methyl 2-(4-(aminomethyl)phenyl)acetate (34 mg, 0.19 mmol) was added, and the mixture was stirred at room temperature for 30 minutes. Water (10 mL) was added, and the mixture was extracted with dichloromethane (3*10 mL). The organic layers were combined, washed with saturated sodium chloride (10 mL), dried over anhydrous sodium sulfate, and filtered. The filtrate was concentrated in vacuo to obtain a crude product, which was separated by a silica gel column (petroleum ether:ethyl acetate=5:1-3:1) to give a product (white solid, 70 mg), with a yield of 83.3%. MS (ESI) m/z: 524.2 (M+1).

Step 3: 2-(4-((3-(2,6-Dichloro-3'-cyano-4'-isobutyl-[1,1'-biphenyl]-4-yl)ureido)methyl)phenyl)acetic acid Methyl 2-(4-((3-(2,6-dichloro-3'-cyano-4'-isobutyl-[1,1'-biphenyl]-4-yl)ureido)methyl)phenyl)-acetate (65 mg, 0.13 mmol), lithium hydroxide monohydrate (17 mg, 0.39 mmol) and ethanol/H$_2$O (2 mL/0.5 mL) were added in a 25 mL single-neck flask, and the mixture was stirred at room temperature for 3 hours. After completion of the reaction, ethanol was removed, water (5 mL) was added and pH of the mixture was adjusted to acidic with 2N hydrochloric acid. The mixture was extracted with ethyl acetate (3*10 mL), the organic layers were dried over anhydrous sodium sulfate, and concentrated in vacuo to give a product (yellow solid, 65 mg), with a yield of 98.5%. $^1$H NMR (400 MHz, DMSO) δ 9.20 (s, 1H), 7.72 (s, 1H), 7.66 (s, 2H), 7.53 (s, 1H), 7.27-7.20 (m, 4H), 6.96 (s, 1H), 4.29 (d, J=5.7 Hz, 2H), 3.54 (s, 2H), 2.73 (d, J=7.3 Hz, 2H), 1.98 (m, 1H), 0.93 (d, J=6.5 Hz, 6H). MS (ESI) m/z: 510.0 (M+1).

Example 58

1-(2,6-Dichloro-3'-cyano-4'-((dimethylamino)methyl)-[1,1'-biphenyl]-4-yl)-3-(4-(ethylsulfonyl)benzyl)urea

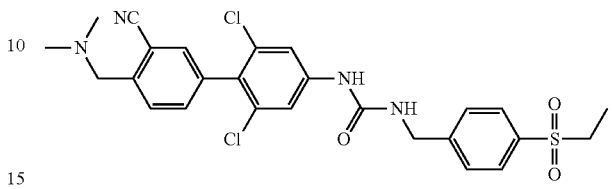

4'-Amino-2',6'-dichloro-4-((dimethylamino)methyl)-[1,1'-biphenyl]-3-carbonitrile (100 mg, 0.31 mmol), dichloromethane (5 mL) and DIEA (120 mg, 0.93 mmol) were added in a 25 mL single-neck flask, and the mixture was stirred in an ice bath for 5 minutes. Then triphosgene (32 mg, 0.11 mmol) was added and the mixture was stirred in the ice bath for 10 minutes. And then (4-(ethylsulfonyl)phenyl)methanamine (75 mg, 0.38 mmol) was added, and the mixture was stirred at room temperature for 1 hour. Water (10 mL) was added, and the mixture was extracted with dichloromethane (3*10 mL). The organic layers were combined, washed with saturated sodium chloride (10 mL), dried over anhydrous sodium sulfate, and filtered. The filtrate was concentrated in vacuo to obtain a crude product, which was separated by a silica gel column (dichloromethane:methanol=50:1) to give a product (white solid, 87 mg), with a yield of 51.2%. $^1$H NMR (400 MHz, CDCl$_3$) δ 7.70 (d, J=8.1 Hz, 2H), 7.66 (d, J=8.3 Hz, 2H), 7.58 (s, 2H), 7.54 (s, 1H), 7.45 (d, J=7.9 Hz, 1H), 7.40 (d, J=8.0 Hz, 2H), 6.10 (t, J=6.0 Hz, 1H), 4.53 (d, J=5.2 Hz, 2H), 3.74 (s, 2H), 3.17 (d, J=7.4 Hz, 2H), 2.39 (s, 6H), 1.31 (t, J=7.4 Hz, 3H). MS (ESI) m/z: 545.0 (M+1).

Example 59

1-(2,6-Dichloro-3'-cyano-4'-((dimethylamino)methyl)-[1,1'-biphenyl]-4-yl)-3-(4-(methyl sulfonyl)benzyl)urea

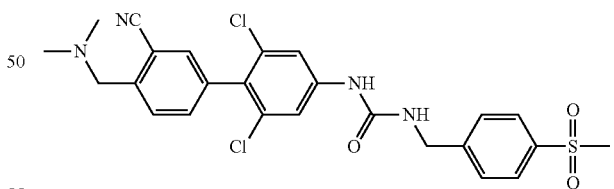

4'-Amino-2',6'-dichloro-4-((dimethylamino)methyl)-[1,1'-biphenyl]-3-carbonitrile (50 mg, 0.16 mmol), dichloromethane (2 mL) and DIEA (62 mg, 0.48 mmol) were added in a 25 mL single-neck flask, and the mixture was stirred in an ice bath for 5 minutes. Then triphosgene (17 mg, 0.056 mmol) was added and the mixture was stirred in the ice bath for 10 minutes. And then (4-(methylsulfonyl)phenyl)methanamine (43 mg, 0.19 mmol) was added, and the mixture was stirred at room temperature for 1 hours. Water (10 mL) was added, and the mixture was extracted with dichloromethane (3*10 mL). The organic layers were combined, washed with saturated sodium chloride (10 mL), dried over anhydrous sodium sulfate, and filtered. The filtrate was concentrated in vacuo to obtain a crude product, which was separated by a silica gel column (dichloromethane:methanol=50:1) to give a product (white solid, 44 mg), with a yield of 53.1%. $^1$H NMR (400 MHz, CD$_3$OD) δ 7.89 (d, J=8.0 Hz, 2H), 7.67-7.63 (m, 1H), 7.57 (d, J=9.0 Hz, 5H), 7.50 (d, J=7.9 Hz, 1H), 4.49 (s, 2H), 3.70 (s, 2H), 3.08 (s, 3H), 2.32 (s, 6H). MS (ESI) m/z: 531.0 (M+1).

Example 60

2',6'-Dichloro-4'-((4-(ethylsulfonyl)phenethyl)amino)-4-isobutyl-[1,1'-biphenyl]-3-carbonitrile

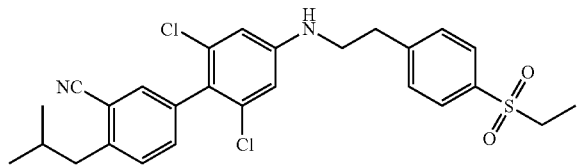 [SMILES: CCS(=O)(=O)c1ccc(CCNc2cc(Cl)c(-c3ccc(CC(C)C)c(C#N)c3)c(Cl)c2)cc1]

N-(2,6-Dichloro-3'-cyano-4'-isobutyl-[1,1'-biphenyl]-4-yl)-2-(4-(ethylsulfonyl)phenyl)acetamide (65 mg, 0.12 mmol) and tetrahydrofuran (1 mL) were added in a 25 mL single-neck flask, then a solution of borane in tetrahydrofuran (0.36 mL, 1M) was added under stirring, and the mixture was stirred at room temperature for 1 hour. Then additional solution of borane in tetrahydrofuran (0.2 mL, 1M) was added, and the mixture was stirred at room temperature for another 1 hour. After completion of the reaction, methanol (10 mL) was added, and the mixture was heated to react at 70° C. for 30 minutes. The mixture was concentrated in vacuo to remove the solvent, and the residue was separated by preparative thin layer chromatography to give a product (white solid, 28 mg), with a yield of 45.1%. $^1$H NMR (400 MHz, CDCl$_3$) δ 7.84 (d, J=6.1 Hz, 2H), 7.47 (s, 1H), 7.45-7.33 (m, 3H), 7.30 (s, 1H), 6.59 (s, 2H), 3.43 (s, 2H), 3.10 (d, J=6.0 Hz, 2H), 3.01 (s, 2H), 2.73 (d, J=5.0 Hz, 2H), 2.02 (s, 1H), 1.66 (s, 1H), 1.26 (s, 3H), 0.96 (d, J=4.1 Hz, 6H). MS (ESI) m/z: 514.8 (M+1).

Example 61

2',6'-Dichloro-4-isobutyl-4'-((4-(methylsulfonyl)phenethyl)amino)-[1,1'-biphenyl]-3-carbonitrile

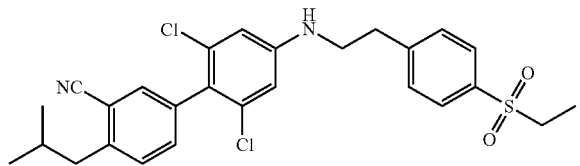 [SMILES: CCS(=O)(=O)c1ccc(CCNc2cc(Cl)c(-c3ccc(CC(C)C)c(C#N)c3)c(Cl)c2)cc1]

N-(2,6-Dichloro-3'-cyano-4'-isobutyl-[1,1'-biphenyl]-4-yl)-2-(4-(methylsulfonyl)phenyl)acetamide (50 mg, 0.10 mmol) and tetrahydrofuran (1 mL) were added in a 25 mL single-neck flask, then a solution of borane in tetrahydrofuran (0.36 mL, 1M) was added under stirring, and the mixture was stirred at room temperature for 1 hour. Then methanol (10 mL) was added, and the mixture was heated to react at 70° C. for 30 minutes. The mixture was concentrated in vacuo to remove the solvent, and the residue was separated by preparative thin layer chromatography (petroleum ether:ethyl acetate=10:1) to give a product (white solid, 15 mg), with a yield of 30.0%. $^1$H NMR (400 MHz, CDCl$_3$) δ 7.94 (d, J=8.1 Hz, 2H), 7.52 (s, 1H), 7.46 (d, J=8.1 Hz, 2H), 7.40 (d, J=8.2 Hz, 1H), 7.34 (d, J=8.0 Hz, 1H), 6.64 (s, 2H), 3.48 (t, J=6.8 Hz, 2H), 3.09 (s, 3H), 3.06 (t, J=6.8 Hz, 2H), 2.78 (d, J=7.3 Hz, 2H), 2.07 (dt, J=13.3, 6.6 Hz, 1H), 1.01 (d, J=6.6 Hz, 6H). MS (ESI) m/z: 500.8 (M+1).

Example 62

2',6'-Dichloro-4-((dimethylamino)methyl)-4'((4-(ethylsulfonyl)phenethyl)amino)-[1,1'-biphenyl]-3-carbonitrile

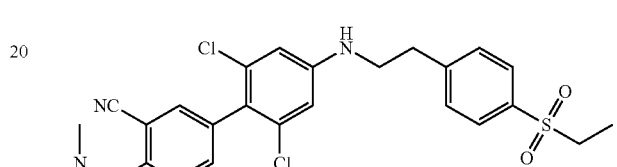

N-(2,6-Dichloro-3'-cyano-4'-((dimethylamino)methyl)-[1,1'-biphenyl]-4-yl)-2-(4-(ethylsulfonyl)phenyl)acetamide (30 mg, 0.057 mmol) and tetrahydrofuran (1 mL) were added in a 25 mL single-neck flask, then a solution of borane in tetrahydrofuran (0.17 mL, 1M) was added under stirring, and the mixture was stirred at room temperature for 1 hour. Then methanol (10 mL) was added, and the mixture was heated to react at 70° C. for 30 minutes. The mixture was concentrated in vacuo to remove the solvent, and the residue was separated by preparative thin layer chromatography (petroleum ether:ethyl acetate=1:2) to give a product (white solid, 20 mg), with a yield of 69.0%. $^1$H NMR (400 MHz, CDCl$_3$) δ 7.86 (d, J=7.8 Hz, 2H), 7.61 (d, J=7.6 Hz, 1H), 7.54 (s, 1H), 7.44 (t, J=9.0 Hz, 3H), 6.62 (s, 2H), 3.70 (s, 2H), 3.46 (d, J=5.7 Hz, 2H), 3.12 (dd, J=14.6, 7.3 Hz, 2H), 3.03 (t, J=6.3 Hz, 2H), 2.35 (s, 6H), 1.29 (t, J=7.1 Hz, 5H). MS (ESI) m/z: 516.0 (M+1).

Example 63

2',6'-Dichloro-4-((dimethylamino)methyl)-4'-((4-(methyl sulfonyl)phenethyl)amino)-[1,1'-biphenyl]-3-carbonitrile

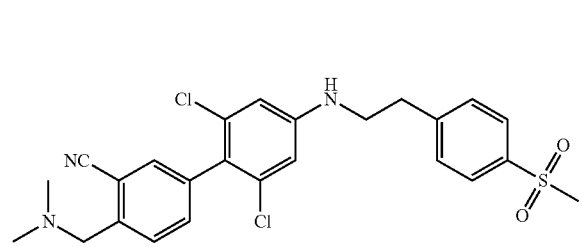

N-(2,6-Dichloro-3'-cyano-4'-((dimethylamino)methyl)-[1,1'-biphenyl]-4-yl)-2-(4-(methylsulfonyl)phenyl)acetamide (52 mg, 0.1 mmol), and tetrahydrofuran (1 mL) were added in a 25 mL single-neck flask, then a solution of borane in tetrahydrofuran (0.17 mL, 1M) was added under stirring, and the mixture was stirred at room temperature for 2 hours. Then methanol (10 mL) was added, and the mixture was heated to react at 70° C. for 30 minutes. The mixture was concentrated in vacuo to remove the solvent, and the residue was separated by preparative thin layer chromatography (petroleum ether:ethyl acetate=1:1) to give a product (white solid, 20 mg), with a yield of 20.6%. $^1$H NMR (400 MHz, CDCl$_3$) δ 7.92 (d, J=7.5 Hz, 2H), 7.62 (s, 1H), 7.55 (s, 1H), 7.45 (t, J=8.9 Hz, 3H), 6.62 (s, 2H), 3.72 (s, 2H), 3.47 (d, J=5.8 Hz, 2H), 3.09-3.01 (m, 5H), 2.37 (s, 6H). MS (ESI) m/z: 502.0 (M+1).

Example 64

Determination of Agonistic Activities of Compounds on RORγ Receptors In Vitro

The agonistic activities of compounds described herein on RORγ receptor were determined by dual fluorescence resonance energy transfer (dual FRET) experiments. The agonistic activity was expressed by half maximum effect concentration (EC$_{50}$).

Experiments:
1) Preparation of RORγ Assay Buffer
100 mL of buffer solution was well mixed with 10 L DTT for use.
2) Preparation of Solutions of Compounds
The concentrations of compound solutions started from 7.5 mM, which were gradually diluted to form ten concentrations in total with a ration of 1:3 for every dilution.
3) Preparation of protein mixtures
  a) 40 nM B-RORγ LBD solution was mixed well with 20 nM SA-APC solution and incubated for 15 minutes at room temperature. Then the resulting mixture was further mixed well with 400 nM Biotin and incubated for another 10 minutes at room temperature.
  b) 40 nM Bioin-SRC1 solution was mixed well with 10 nM SA-eu solution and was incubated for 15 minutes at room temperature. Then the resulting mixture was further mixed well with 200 nM Biotin and was incubated for another 10 minutes at room temperature.
  c) The above-described two pre-mixes (mixtures from steps a) and b)) were gently mixed together with a ratio of 1:1, and incubated for 5 minutes at room temperature.
  d) A mixture (25 μL) of B-RORγ LBD/SA-APC and Bioin-SRC1/SA-eu together with a test compound was added to one of the wells of a 384-well plate, and then the plate was centrifuged for one minute at 1000 rpm, and incubated at room temperature for one hour. The data were read on an Envision microplate detector and EC$_{50}$ values were calculated. The results showed that the compounds of the present invention had good agonistic activities on RORγ protein receptor (see Table 1).

TABLE 1

Determination of the RORγ agonistic activity of some example compounds prepared above

| Example No. | EC$_{50}$ |
| --- | --- |
| 1 | ***** |
| 2 | ***** |
| 3 | **** |
| 4 | ***** |
| 5 | ***** |
| 6 | ***** |
| 7 | ***** |
| 8 | ***** |
| 9A | ***** |
| 9B | ***** |
| 10 | ***** |

TABLE 1-continued

Determination of the RORγ agonistic activity of some example compounds prepared above

| Example No. | EC$_{50}$ |
| --- | --- |
| 11 | ***** |
| 12 | ***** |
| 13 | ***** |
| 14 | ***** |
| 15 | ***** |
| 16 | ***** |
| 17 | ***** |
| 18 | ***** |
| 19 | ***** |
| 20 | ***** |
| 21 | ****** |
| 22 | ***** |
| 23 | ***** |
| 24 | ****** |
| 25 | ****** |
| 26 | ***** |
| 27 | ***** |
| 28 | ***** |
| 29 | ***** |
| 30 | ***** |
| 31 | ****** |
| 32 | ***** |
| 33 | ***** |
| 34 | ***** |
| 35 | ***** |
| 36 | ***** |
| 37 | ***** |
| 38 | * |
| 39 | ***** |
| 40 | ***** |
| 41 | ***** |
| 42 | ***** |
| 43 | ***** |
| 44 | ***** |
| 45 | ***** |
| 46 | ***** |
| 47 | **** |
| 48 | **** |
| 49 | **** |
| 50 | **** |
| 51 | *** |
| 52 | ** |
| 53 | ***** |
| 54 | ***** |
| 55 | ***** |
| 56 | ***** |
| 57 | ***** |
| 58 | ***** |
| 59 | ***** |
| 60 | ***** |
| 61 | ***** |
| 62 | ****** |
| 63 | ****** |

EC$_{50}$ value is an average of at least two independent experiments.
****** means EC$_{50}$ < 10 nM;
***** means 10 nM ≤ EC$_{50}$ < 50 nM;
**** means 50 nM ≤ EC$_{50}$ < 100 nM;
*** means 100 nM ≤ EC$_{50}$ < 500 nM;
** means 500 nM ≤ EC$_{50}$ < 1000 nM;
* means EC$_{50}$ ≥ 1000 nM.

Example 65

Determination of the Activation Rate on Mouse Lymphoma EL4

Mouse lymphoma EL4 cells transfected with RORγt plasmid were cultured at 37° C. under an atmosphere with 5% CO$_2$, with a test compound added simultaneously. After 24 hours, the generation efficiency of IL-17A was analyzed. Before collection of cells, PMA at 50 ng/mL and ionomycin at 500 ng/mL were added for stimulation for 4 hours. The proportion of IL-17 was detected by intracellular staining and flow cytometry. Meanwhile, Live/Dead Cell Dye (Invitrogen) staining was used to analyze the cell survival rate and to judge whether the drug had toxicity to cells. The activation rate of IL-17 generated by EL4 cells for the compound was measured at a concentration of 2 μM. The results showed that the compounds of the present invention had good abilities to increase IL-17 generation (see Table 2).

TABLE 2

Determination of the activation of IL-17 generated by EL4 cells

| Example No. | $_+$act % |
| --- | --- |
| 2 | ** |
| 5 | * |
| 6 | ** |
| 9A | * |
| 11 | * |
| 13 | * |
| 16 | *** |
| 17 | *** |
| 19 | ** |
| 20 | *** |
| 21 | ** |
| 24 | * |
| 26 | * |
| 32 | ** |
| 33 | ** |
| 34 | *** |
| 35 | *** |
| 36 | *** |
| 37 | ** |
| 40 | *** |
| 41 | *** |
| 47 | * |
| 49 | * |
| 53 | ** |
| 55 | ** |
| 58 | ** |
| 60 | ** |
| 62 | ** |

*** means $_+$act %@ 2 μM > 50%;
** means $_+$act %@ 2 μM between 20%-50%;
* means $_+$act %@ 2 μM < 20%.

Example 66

Determination of the Half-Maximal Effect Concentration of Mouse Th17 Cell Differentiation Experimental methods: Mouse spleen CD4$^+$T cells were separated and differentiated into Th17 cells. CD4$^+$T cells were cultured in the environment containing anti-CD3 (0.25 μg/mL), anti-CD28 (1 μg/mL), anti-IL4 (2 μg/mL), anti-IFN-γ (2 μg/mL), TGF-β (5 ng/mL), and IL6 (20 ng/mL), with a test compound added at the same time. After 96 hours, the differentiation efficiency of Th17 was analyzed. Before collection of cells, PMA at 50 ng/mL and ionomycin at 500 ng/mL were added for stimulation for 4 hours, and the proportion of IL-17 was detected by intracellular staining and flow cytometry. Meanwhile, we used Live/Dead Cell Dye (Invitrogen) staining method to analyze the cell survival rate and to judge whether the drug had toxicity to cells, and determined the half-maximal effect concentration $EC_{50}$ of the compounds. The results showed that the compounds of the present invention had good abilities to induce Th17 differentiation and increase IL-17 production (see Table 3).

TABLE 3

$EC_{50}$ results of mouse Th17 cell differentiation experiments

| Example No. | $EC_{50}$ |
| --- | --- |
| 16 | *** |
| 17 | *** |
| 19 | ** |
| 20 | * |
| 21 | *** |
| 32 | *** |
| 36 | * |
| 41 | * |
| 43 | ** |

*** means $EC_{50}$ value < 50 nM;
** means $EC_{50}$ value between 50 nM to 150 nM;
* means $EC_{50}$ value > 150 nM.

Example 67

Determination of the Inhibition on B16F10 Mouse Melanoma Cell

Experimental methods: B16F10 mouse melanoma cells (ATCC) were subcutaneously injected on both flanks of C57/BL6 mice ($2*10^5$ cells/flank). Eight days after injection, the mice were dosed intraperitoneally with drugs at 50 mg/kg daily or vehicle (solvent control). Starting from the 8$^{th}$ day after tumor injection, tumor sizes were measured every two days using caliper, and the tumor volumes were calculated by the formula 0.5*length*width$^2$. Mice were sacrificed when tumor volume reached 1500 mm$^3$, which is the ethical end point of experiment.

Figure 2:
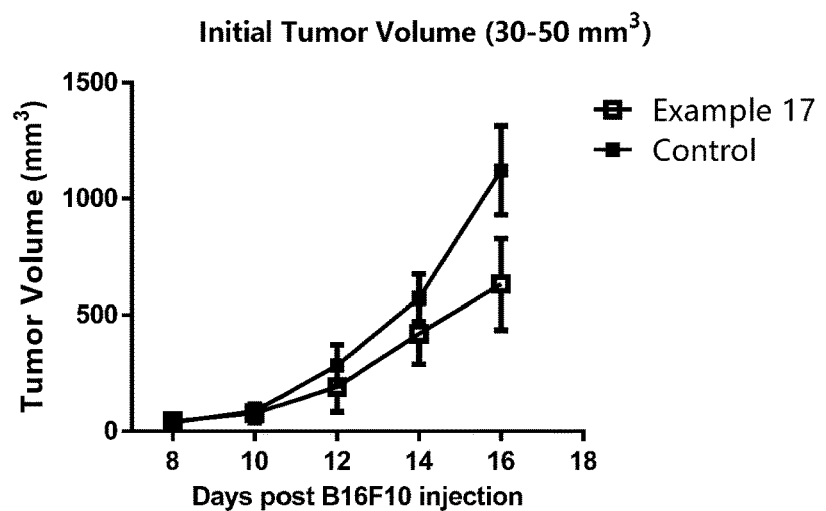
FIG. 2 shows an experimental curve of the compound prepared in example 17 in inhibiting B16F10 murine melanoma cells.
Figure 3:
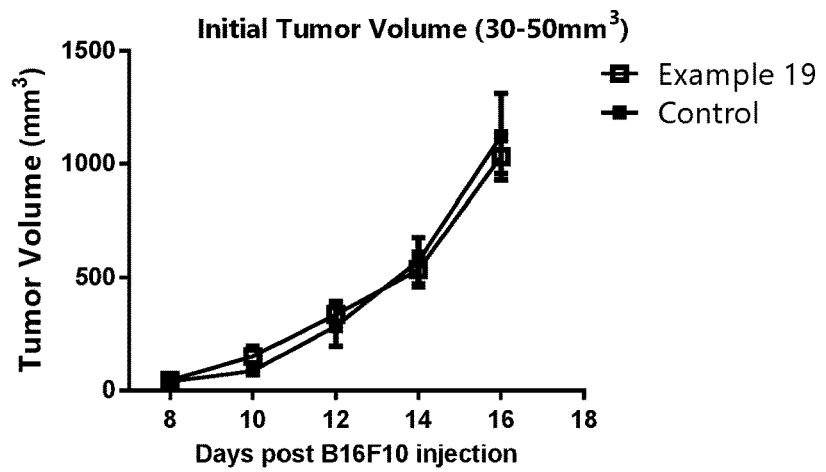
FIG. 3 shows an experimental curve of the compound prepared in example 19 in inhibiting B16F10 murine melanoma cells.
Figure 4:
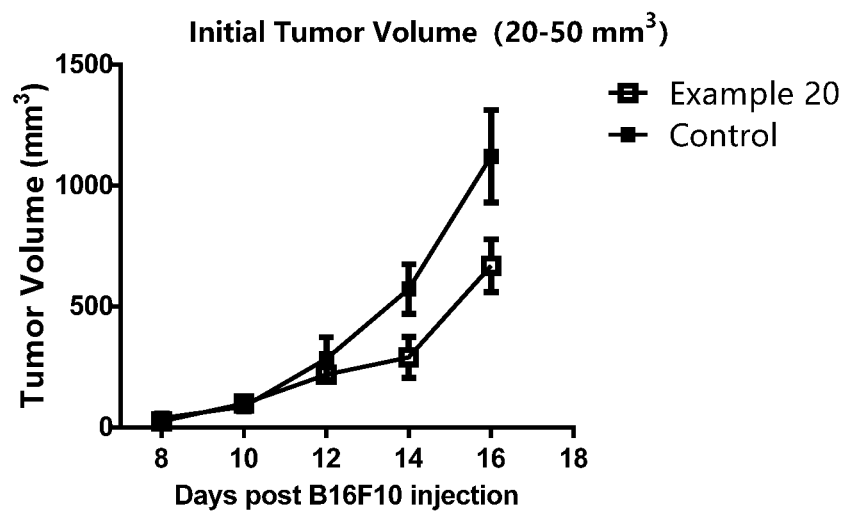
FIG. 4 shows an experimental curve of the compound prepared in example 20 in inhibiting B16F10 murine melanoma cells.
Figure 5:
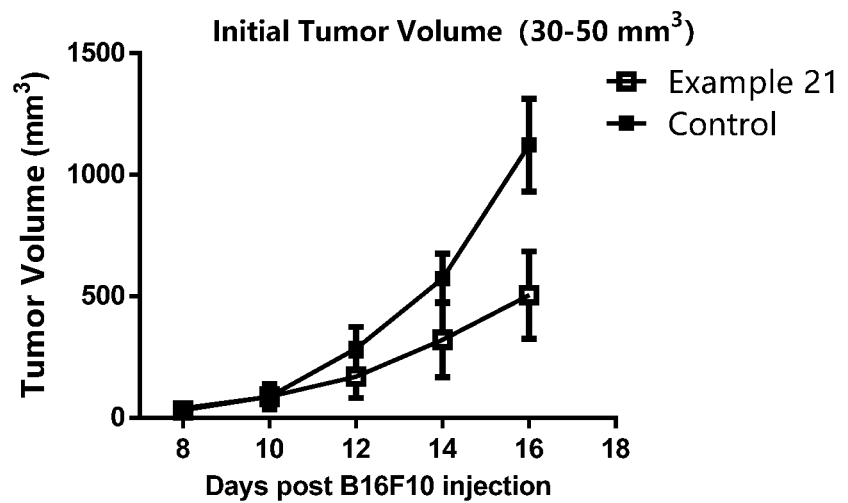
FIG. 5 shows an experimental curve of the compound prepared in embodiment 21 in inhibiting B16F10 murine melanoma cells.

An experimental curve of the compound prepared in example 16 in inhibiting B16F10 mouse melanoma cells is shown in FIG. 1. An experimental curve of the compound prepared in example 17 in inhibiting B16F10 mouse melanoma cells is shown in FIG. 2. An experimental curve of the compound prepared in example 19 in inhibiting B16F10 mouse melanoma cells is shown in FIG. 3. An experimental curve of the compound prepared in example 20 in inhibiting B16F10 mouse melanoma cells is shown in FIG. 4. An experimental curve of the compound prepared in example 21 in inhibiting B16F10 mouse melanoma cells is shown in FIG. 5. The results showed that the compounds of the present invention had good abilities in inhibiting B16F10 mouse melanoma cell growth.

The present invention describes a series of biaryl derivatives having particular structural type as RORγt agonists for cancer immunotherapy. The structures of the biaryl derivatives are characterized by a para-substitution of $(R_1R_2R_3)$C— or $R_1$'O— on the outer aromatic ring, and only if the substituent $(R_1R_2R_3)$C— or $R_1$'O— is on the para position of the outer aryl ring of the biaryl group and the substituent $(R_1R_2R_3)$C— or $R_1$'O— is of the right property and size, can the compound exhibit RORγt agonist activities. If the substituent $(R_1R_2R_3)$C— or $R_1$'O— is too large or too small or inappropriate in property, the compound will loss the RORγt agonist activity.

The invention claimed is:

1. A compound of formula (I) or (II) or a pharmaceutically acceptable salt thereof:

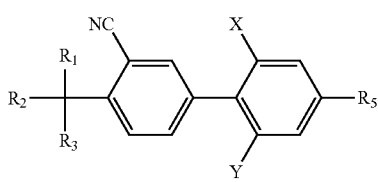

(I)

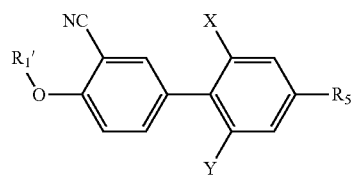

(II)

wherein:

R$_1$ is selected from the group consisting of R$_{11}$-substituted C$_3$-C$_5$ alkyl, R$_{11}$-substituted C$_3$-C$_6$ cycloalkyl, R$_{11}$-substituted C$_3$-C$_6$ heterocycloalkyl, and —NR$_9$R$_{10}$, wherein R$_2$ and R$_3$ are both hydrogens; or R$_1$ and R$_2$ form C$_2$-C$_6$ alkyl alkenyl or C$_3$-C$_7$ cycloalkyl alkenyl wherein R$_3$ is hydrogen;

R$_1$' is selected from the group consisting of C$_1$-C$_6$ alkyl, C$_3$-C$_6$ cycloalkyl, and C$_3$-C$_6$ heterocycloalkyl;

X is hydrogen or a halogen, and Y is a halogen;

R$_5$ is selected from

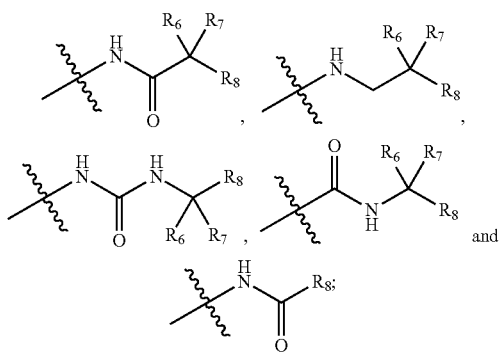

R$_6$ and R$_7$ are both hydrogens;

R$_8$ is selected from the group consisting of phenyl substituted with one or more R$_{31}$, pyridyl substituted with one or more R$_{31}$, and pyrimidinyl substituted with one or more R$_{31}$;

R$_9$ and R$_{10}$ are each independently selected from the group consisting of hydrogen, C$_1$-C$_6$ alkyl and C$_3$-C$_6$ cycloalkyl; or R$_9$ and R$_{10}$ form a cyclic group having four to seven ring members together with the nitrogen atom to which they attach;

R$_{11}$ is selected from the group consisting of halogen and hydrogen;

R$_{31}$ is selected from the group consisting of hydrogen, C$_1$-C$_6$ alkyl sulfonyl, —SO$_2$NR$_9$R$_{10}$, —P(O)R$_9$R$_{10}$, —C(O)OR$_9$, —C(O)R$_9$, and —CH$_2$COOH.

2. The compound of Formula (I) or the pharmaceutically acceptable salt thereof according to claim 1, wherein:

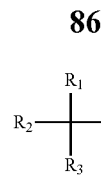

is selected from the group consisting of

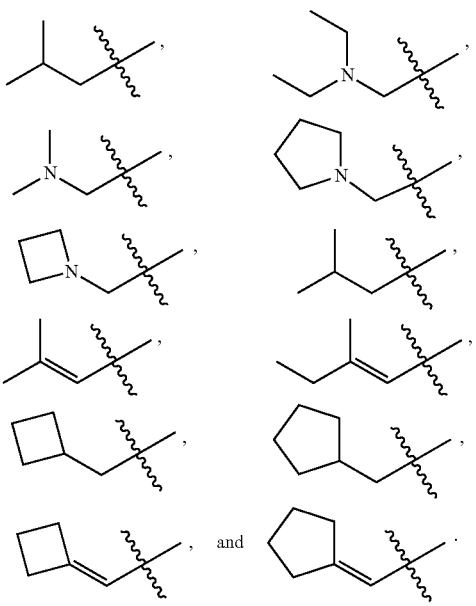

3. The compound of Formula (I) or (II) or the pharmaceutically acceptable salt thereof according to claim 1, wherein the compound is selected from the following structures:

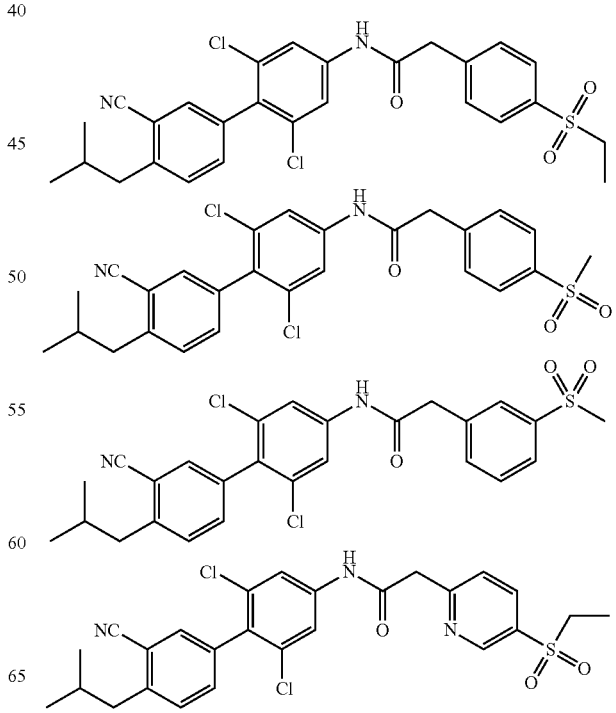

-continued
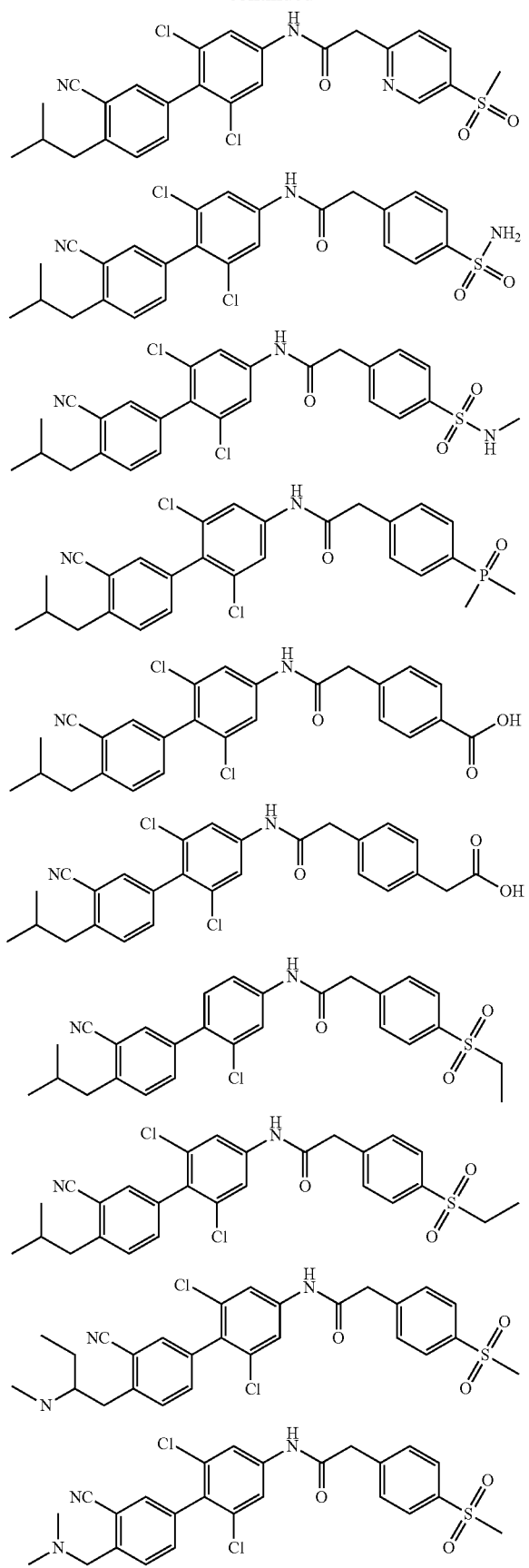
-continued
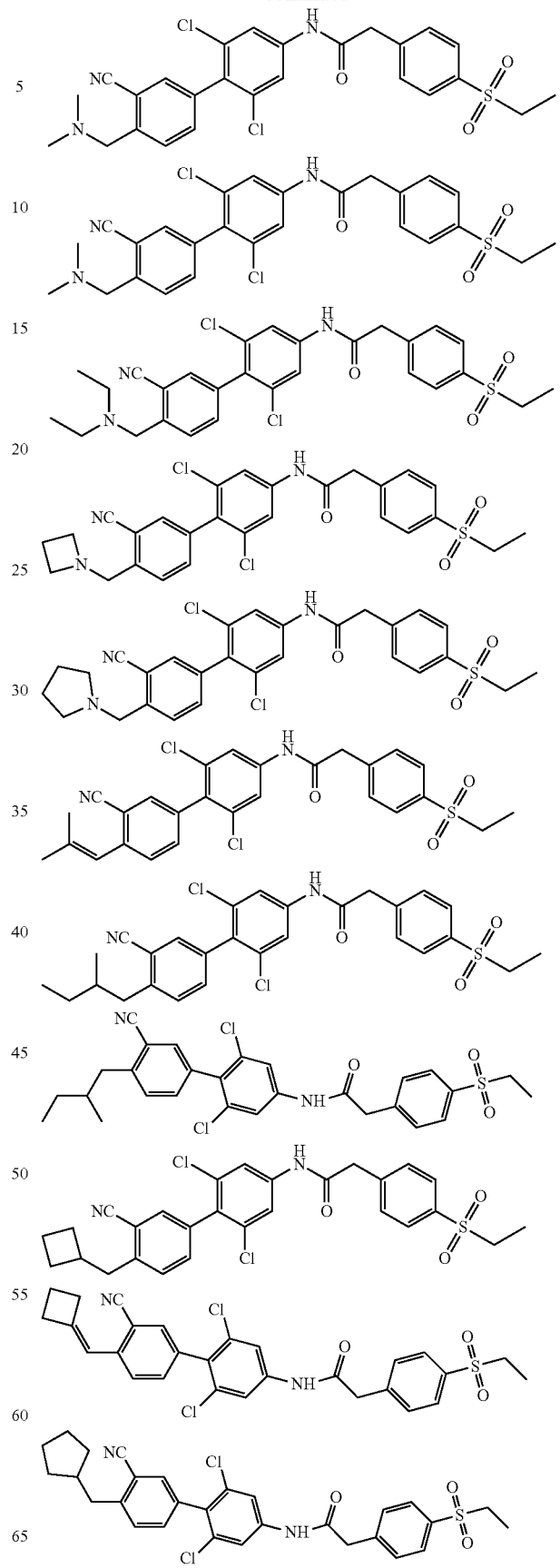

89
-continued
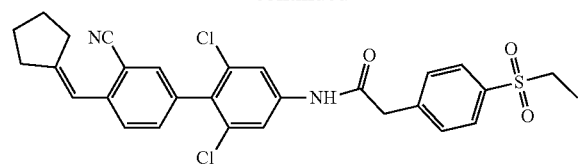
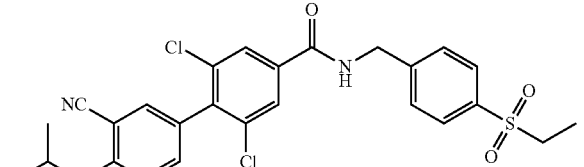
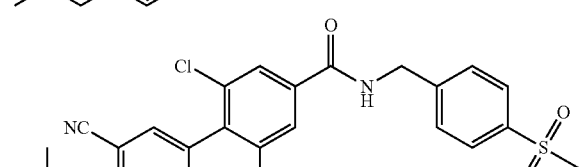
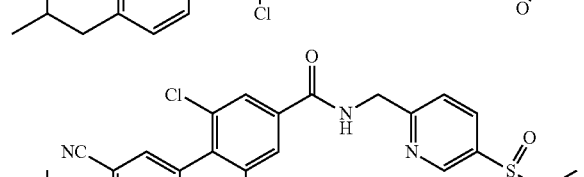
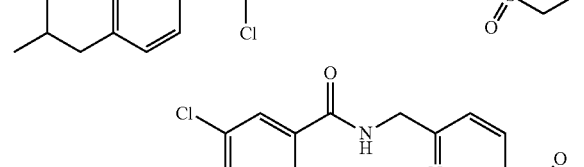
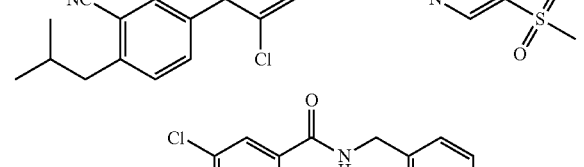
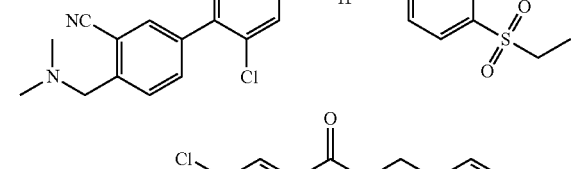
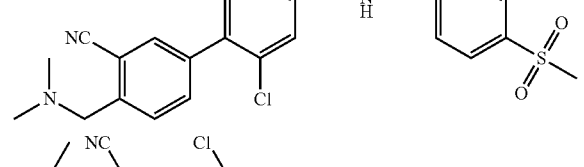
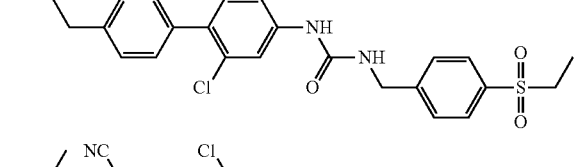
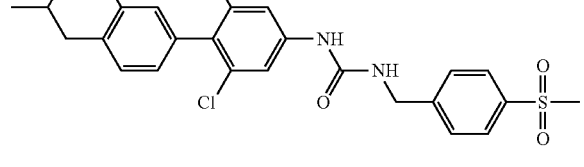
90
-continued
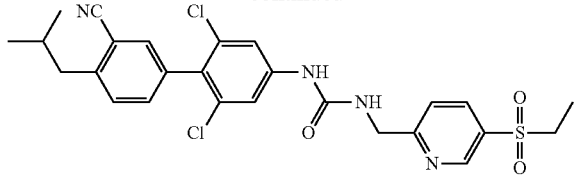
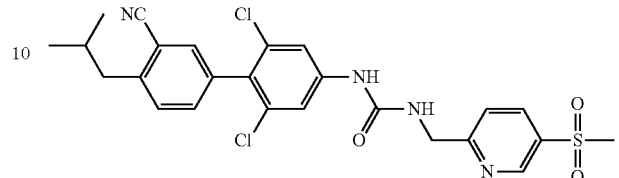
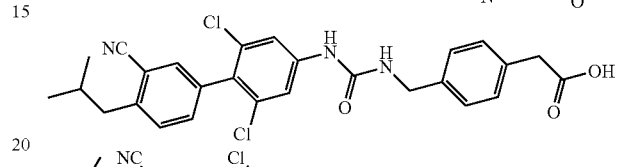
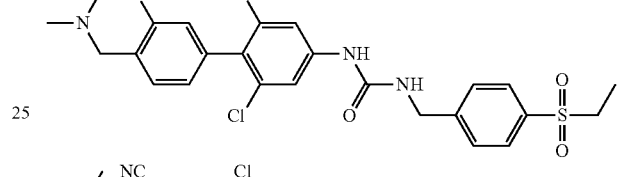
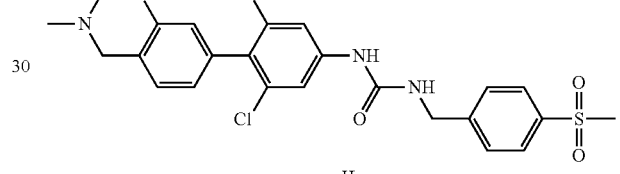
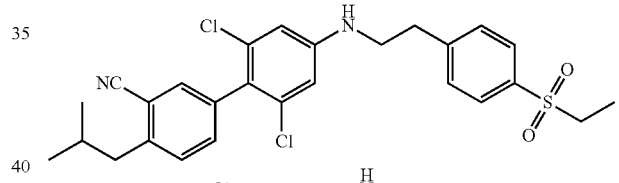
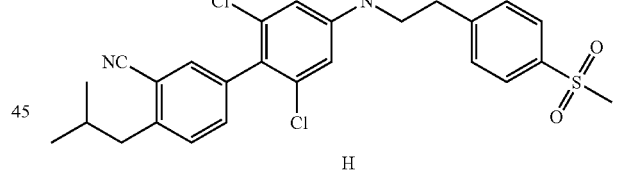
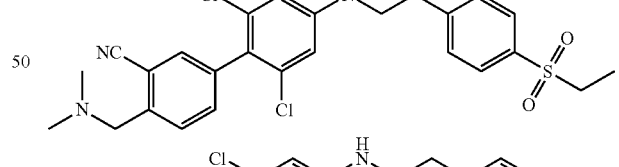
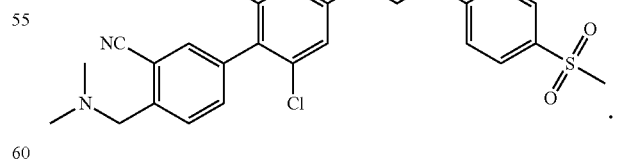
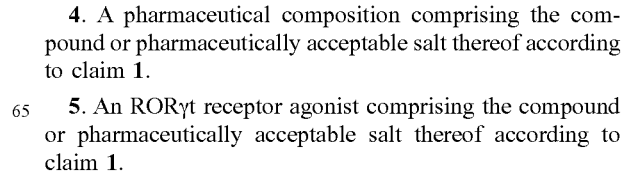
4. A pharmaceutical composition comprising the compound or pharmaceutically acceptable salt thereof according to claim 1.
5. An RORγt receptor agonist comprising the compound or pharmaceutically acceptable salt thereof according to claim 1.

6. A method for treating or preventing RORγt receptor related diseases, comprising administering the compound or pharmaceutically acceptable salt thereof according to claim 1.

7. The method according to claim 6, wherein the diseases are viral infections or cancers.

* * * * *